United States Patent
Bergman et al.

[11] Patent Number: 6,127,414
[45] Date of Patent: Oct. 3, 2000

[54] NPY ANTAGONISTS

[75] Inventors: Nils-Åke Bergman, Västra Frölunda, Sweden; Thomas D'Ambra, Rexford; Garry M Pilling, East Nassau, both of N.Y.

[73] Assignee: Astra Aktiebolag, Sodertalje, Sweden

[21] Appl. No.: 09/171,779

[22] PCT Filed: Sep. 21, 1998

[86] PCT No.: PCT/SE98/01686

§ 371 Date: Oct. 26, 1998

§ 102(e) Date: Oct. 26, 1998

[87] PCT Pub. No.: WO99/15498

PCT Pub. Date: Apr. 1, 1999

[30] Foreign Application Priority Data

Sep. 23, 1997 [SE] Sweden ................................. 9703414

[51] Int. Cl.[7] .................. A01N 37/10; A01N 37/12; A01N 37/44; A61K 31/235; A61K 31/24

[52] U.S. Cl. .................. 514/533; 514/539; 514/586; 514/595; 514/616; 514/618; 514/619; 514/620; 560/25; 560/27; 560/28; 560/34; 562/439; 564/47; 564/56; 564/147; 564/153; 564/154; 564/157

[58] Field of Search .................. 560/34, 25, 27, 560/28; 592/439; 594/47, 56, 147, 153, 154, 157; 514/533, 539, 586, 595, 616, 618, 619, 620

[56] References Cited

U.S. PATENT DOCUMENTS

| | | |
|---|---|---|
| 5,779,631 | 7/1998 | Chance . |
| 5,889,016 | 3/1999 | Bruce et al. . |
| 5,962,455 | 10/1999 | Blum et al. . |

FOREIGN PATENT DOCUMENTS

| | | | |
|---|---|---|---|
| WO 9417035 | 8/1994 | WIPO | ................ C07C 279/14 |
| 97/19911 | 6/1997 | WIPO . | |
| 97/19914 | 6/1997 | WIPO . | |
| 97/25041 | 7/1997 | WIPO . | |
| 97/34873 | 9/1997 | WIPO . | |
| 97/46250 | 12/1997 | WIPO . | |
| 98/03493 | 1/1998 | WIPO . | |
| 98/03494 | 1/1998 | WIPO . | |
| WO 98/03492 | 1/1998 | WIPO | ................ C07D 295/18 |
| 98/07420 | 2/1998 | WIPO . | |
| 98/24768 | 6/1998 | WIPO . | |
| 98/25907 | 6/1998 | WIPO . | |
| 98/25908 | 6/1998 | WIPO . | |
| 98/27063 | 6/1998 | WIPO . | |
| 98/35941 | 8/1998 | WIPO . | |
| 98/35944 | 8/1998 | WIPO . | |
| WO 98/33791 | 8/1998 | WIPO | ................ C07D 401/12 |
| 98/40356 | 9/1998 | WIPO . | |

*Primary Examiner*—Johann Richter
*Assistant Examiner*—Brian J. Davis
*Attorney, Agent, or Firm*—Nixon & Vanderhye

[57] ABSTRACT

There is provided pharmaceutically useful compounds of formula I,

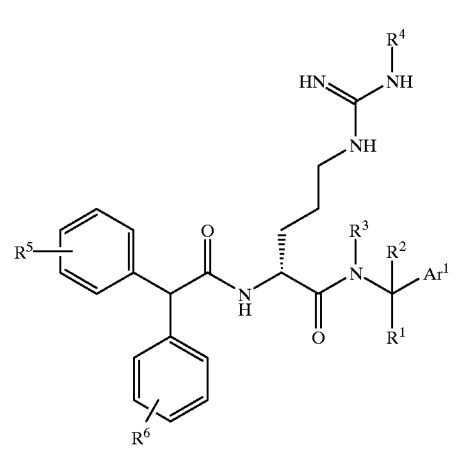

wherein $Ar^1$, $R^1$, $R^2$, $R^3$, $R^4$, $R^5$ and $R^6$ have meanings given in the description, which are useful as antagonists of neuropeptide Y and in particular in the treatment of cardiovascular diseases, for example vasoconstriction.

24 Claims, No Drawings

NPY ANTAGONISTS

This application is a 371 of PCT/SE98/01686 filed Sep. 21, 1998.

FIELD OF THE INVENTION

This invention relates to new pharmaceutically-useful compounds, in particular antagonists of neuropeptide Y, the use of such compounds as medicaments, pharmaceutical compositions containing them and synthetic routes to their production.

BACKGROUND

Neuropeptide Y (NPY) is a peptide consisting of 36 amino acids. In recent years it has been established that NPY is an important co-transmitter in the peripheral sympathetic nervous system.

It has been postulated (see Pharmacological Reviews (1996) 48, 113) that the effects of sympathetic nerve activation are not only due to the neuronal release of noradrenaline but may also be the result of a simultaneous release of NPY from the sympathetic nerve terminal.

Released NPY is known to elicit marked constriction of blood vessels in both the heart (coronary arteries) and in most peripheral organs. This vasoconstrictive effect of NPY is believed to be mediated by a receptor sub-type known as $Y_1$.

Released NPY may also act on autonomic nerve endings to inhibit the release of neurotransmitters and, in doing so, reduce the cardiac vagal tone as a result of decreased acetylcholine release. This effect of NPY is believed to be mediated by a receptor sub-type known as Y2.

Other NPY-receptor sub-types, including the $Y_3$, $Y_4$, $Y_5$ and Y6 sub-receptors, have been identified. The precise functions of these sub-receptors have not been identified in any detail, but the $Y_5$ sub-receptor is thought to be involved in feeding and eating regulation (see Exp. Opin. Invest. Drugs, 6, 437 (1997)).

Increased plasma concentrations of NPY have been found in several cardiovascular diseases including angina pectoris, myocardial infarction and hypertension. Further, emotional stress has been shown to cause a significant increase in plasma NPY levels (see Circulation (1994) 90, I-268, Abstract No. 1445). Such observations suggest a significant pathogenic role for NPY in myocardial ischemic heart disease and hypertension. Moreover, by causing coronary vasoconstriction and reduced vagal tone, NPY may predispose a patient to ventricular fibrillation and sudden cardiac death.

Effective NPY antagonists would therefore be expected to be useful in the treatment of inter alia cardiovascular diseases.

PRIOR ART

Non-peptide antagonists of NPY have been disclosed in European Patent Applications 614 911, 747 357, 747 356 and 747 378, International Patent Applications WO 94/17035, WO 97/19911, WO 97/19913, WO 97/19914, WO 96/22305, WO 96/40660, WO 96/12490, WO 97/09308, WO 97/20820, WO 97/20821, WO 97/20822 and WO 97/20823 and U.S. Pat. Nos. 5,552,411 and 5,567,714.

European Patent Applications 747 357, 747 356 and 747 378 disclose dihydropyridine derivatives as $Y_1$ sub-receptor antagonists.

International Patent Applications WO 96/12490, WO 97/09308 and U.S. Pat. No. 5,567,714 disclose benzothiophene and indole derivatives as $Y_1$ sub-receptor antagonists.

International Patent Application WO 96/40660 discloses benzylamine derivatives as $Y_1$ sub-receptor antagonists or partial $Y_1$ sub-receptor agonists.

U.S. Pat. No. 5,552,411 discloses quinoline derivatives as $Y_1$ sub-receptor antagonists.

International Patent Applications WO 97/20820, WO 97/20821, WO 97/20822 and WO 97/20823 disclose quinazoline derivatives as $Y_5$ sub-receptor antagonists and are thus indicated for use in the treatment of eating disorders.

The compounds disclosed in International Patent Application WO 96/22305 are disclosed as $Y_2$ sub-receptor antagonists and are also indicated for use in the treatment of eating disorders. Amongst the compounds specifically disclosed are phenylalaninamide derivatives of N-(diphenylpropionyl)-arginine.

Whether the compounds disclosed in European Patent Application 614 911 and International Patent Application WO 94/17035 are $Y_1$ or Y2 sub-receptor antagonists is not mentioned.

International Patent Application WO 94/17035 discloses certain amino acid derivatives, including (R)-$N^2$-(diphenylacetyl)-N-[(4-hydroxyphenyl)-methyl]arginine amide, as antagonists of NPY. The presence of substituents on the carbon atom which is in the a-position relative to the (4-hydroxy) substituted phenyl group in the above molecule is neither mentioned nor suggested.

Surprisingly we have found that novel analogues of the above compound, containing substituents on the carbon atom which is in the Deposition relative to the above-mentioned phenyl group are remarkably good antagonists of NPY.

DISCLOSURE OF THE INVENTION

According to the invention there is provided a compound of formula I,

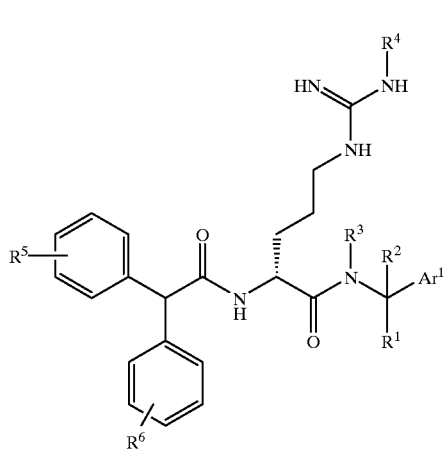

wherein

Ar$^1$ represents a structural fragment of the formula

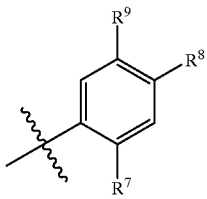

or represents 1- or 2-naphthyl, which latter group is optionally substituted by one or more substituent selected from OH, halo or C$_{1-7}$ alkoxy;

R$^1$ represents C(O)NH$_2$, C$_{1-4}$ alkyl (optionally substituted or terminated by one or more substituent selected from hydroxy or amino), or, together with R$^7$ (in Ar$^1$), forms C$_{2-3}$ alkylene;

R$^4$ represents H, C$_{1-7}$ alkyl or C$_{1-4}$ alkylenephenyl (in which latter group, the phenyl group is optionally substituted by one or more substituent selected from OH or C$_{1-4}$ alkoxy);

R$^5$ and R$^6$ independently represent H, OH, C$_{1-4}$ alkyl, C$_{1-4}$ alkoxy or halo;

R$^7$ represents H, OH or, together with R$^1$, forms C$_{2-3}$ alkylene;

R$^8$ represents H, halo, OH, C$_{1-7}$ alkoxy, phenyl, phenoxy, benzyloxy, —(CH$_2$)$_n$C(O)N(R$^{10}$)R$^{11}$, —(CH$_2$)$_n$N(H)C(O)N(R$^{10}$)R$^{11}$ or —O(CH$_2$)$_n$C(O)OR$^{10}$;

R$^9$ represents H, halo, OH or C$_{1-7}$ alkoxy;

R$^2$, R$^3$, R$^{10}$ and R$^{11}$ independently represent H or C$_{1-7}$ alkyl; and n represents 1, 2, 3 or 4;

or a pharmaceutically acceptable derivative thereof (hereinafter referred to together as "the compounds of the invention").

Pharmaceutically acceptable derivatives includes solvates and salts. Particular salts which may be mentioned include those of hydrochloric, acetic and camphorsulphonic acid.

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism, All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. The desired optical isomers may be made by reaction of the appropriate optically active starting materials under conditions which will not cause racemisation or epimerisation. Desired optical isomers may also be obtained by derivatisation, for example by reacting an intermediate with a homochiral acid, separating the diastereomeric derivatives by conventional means (e.g. HPLC, chromatography over silica) and converting back to the optically pure intermediate. All stereoisomers are included within the scope of the invention.

Alkyl groups which R$^1$, R$^2$, R$^3$, R$^4$, R$^5$, R$^6$, R$^{10}$ and R$^{11}$ may represent may be linear or branched, may be cyclic or acyclic, may be saturated or unsaturated and/or may be optionally interrupted by oxygen. Alkoxy groups which R$^5$, R$^6$, R$^8$ and R$^9$ may represent, and with which Ar$^1$ and R$^4$ may be substituted, may be linear or branched, may be cyclic or acyclic, may be saturated or unsaturated and/or may be optionally interrupted by oxygen. The alkylene part of alkylenephenyl groups which R$^4$ may represent may be linear or branched and/or may be saturated or unsaturated. Alkylene groups which R$^1$ and R$^7$ may together represent may be linear or branched and/or may be saturated or unsaturated.

Halo groups which R$^5$, R$^6$, R$^1$ and R$^9$ may represent, and with which Ar$^1$ may be substituted, include fluoro, chloro, bromo and iodo.

The wavy line on the carbon atom in the structural fragment

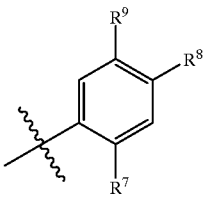

signifies the bond position of the fragment.

Abbreviations are listed at the end of this specification.

Preferred compounds of formula I include those wherein:

R$^1$ represents C(O)NH$_2$, CH$_2$OH, ethyl or, especially, methyl;

R$^2$ represents H;

R$^3$ represents H or methyl;

R$^4$ represents H;

R$^5$ represents OH, halo, methyl, methoxy or, especially, H;

R$^6$ represents OH, halo, methyl, methoxy or, especially, H;

R$^7$ represents H;

R$^8$ represents OCH$_3$, bromo, —CH$_2$C(O)NH$_2$, —CH$_2$N(H)C(O)NH$_2$ or, especially, OH;

R$^9$ represents H;

R$^{10}$ represents H;

R$^{11}$ represents H.

Preferred compounds of formula I include those wherein the carbon atom which is in the α-position relative to Ar$^1$ in the fragment

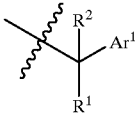

is in the:

(a) R-configuration when R$^1$ represents C$_{1-4}$ alkyl; and (b) S-configuration when R$^1$ represents C(O)NH$_2$ or CH$_2$OH.

The wavy line on the carbon atom in the above fragment signifies the bond position of the fragment.

Preferred compounds of the invention include:

(R)-N$^2$-(diphenylacetyl)-(R)-N-[1-(4-methoxyphenyl)ethyl]arginine amide;

(R)-N$^2$-(diphenylacetyl)-(R,S)-N-(1-phenylpropyl)arginine amide;

(R)-N$^2$-(diphenylacetyl)-(R,S)-N-[1-(4-hydroxyphenyl)ethyl]arginine amide;

(R)-N$^2$-(diphenylacetyl)-(R)-N-[1-(4-hydroxyphenyl)ethyl]arginine amide;

(R)-N$^2$-(diphenylacetyl)-(S)-N-[1-(4-methoxyphenyl)ethyl]arginine amide;

(R)-N²-(diphenylacetyl)-(S)-N-[1-(4-bromophenyl)ethyl]arginine amide;
(R)-N²-(diphenylacetyl)-(R)-N-[1-(4-bromophenyl)ethyl]arginine amide;
(R)-N²-(diphenylacetyl)-(R,S)-N-[1-(3-methoxyphenyl)ethyl]arginine amide;
(R)-N²-(diphenylacetyl)-(R)-N-(1-phenylethyl)arginine amide;
(R)-N²-(diphenylacetyl)-(S)-N-(1-phenylethyl)arginine amide;
(R)-N²-(diphenylacetyl)-(R,S)-N-[1-cyclopropyl-1-(4-methoxyphenyl)-methyl]-arginine amide;
(R)-N²-(diphenylacetyl)-N-(1-methyl-1-phenylethyl)arginine amide;
(R)-N²-(diphenylacetyl)-(R,S)-N-(1-indanyl)arginine amide;
(R)-N²-(diphenylacetyl)-(S or R)-N-(1-carbamoyl-phenylmethyl)arginine amide;
(R)-N²-(diphenylacetyl)-(R or S)-N-[1-carbamoyl-(4-methoxypheny)-methyl]arginine amide;
(R)-N²-(diphenylacetyl)-(S)-N-(2-hydroxy-1-phenylethyl)arginine amide;
(R)-N²-(diphenylacetyl)-(R)-N-(2-hydroxy-1-phenylethyl)arginine amide;
(R)-N²-(diphenylacetyl)-(R)-N-[2-hydroxy-1-(4-methoxyphenyl)ethyl]-arginine amide;
(R)-N²-(diphenylacetyl)-(S)-N-[2-hydroxy-1-(4-methoxyphenyl)ethyl]-arginine amide;
(R)-N²-(diphenylacetyl)-(S)-N-[1-(4-hydroxyphenyl)ethyl]arginine amide;
(R)-N²-(diphenylacetyl)-(R,S)-N-[1-(4-methoxyphenyl)ethyl]arginine amide;
(R)-N²-(diphenylacetyl)-N-methyl-(R)-N-(1-phenylethyl)arginine amide;
(R)-N²-(diphenylacetyl)-N-methyl-(S)-N-(1-phenylethyl)arginine amide;
(R)-N²-(diphenylacetyl)-(R,S)-N-[1-(4-cyclopropylmethoxyphenyl)ethyl]-arginine amide;
(R)-N²-(diphenylacetyl)-(R)-N-[1-(4-benzyloxyphenyl)ethyl]arginine amide;
(R)-N²-(diphenylacetyl)-(R,S)-N-[1-(4-phenoxyphenyl)ethyl]arginine amide;
(R)-N²-(diphenylacetyl)-(R,S)-N-[1-(4-phenylphenyl)ethyl]arginine amide;
(R)-N²-(diphenylacetyl)-(R,S)-N-[1-(2-naphthyl)ethyl]arginine amide;
(R)-N²-(diphenylacetyl)-(R)-N-[1-(1-naphthyl)ethyl]arginine amide;
(R)-N²-[(R,S)-2-(4-methoxyphenyl)phenylacetyl]-(R)-N-[1-(4-hydroxy-phenyl)ethyl]arginine amide;
(R)-N²-[(R,S)-2-(4-methylphenyl)phenylacetyl]-(R)-N-[1-(4-hydroxy-phenyl)ethyl]arginine amide;
(R)-N²-[(R,S)-2-(4-chlorophenyl)phenylacetyl]-(R)-N-[1-(4-hydroxy-phenyl)ethyl]arginine amide;
(R)-N²-(4,4'-dichlorodiphenylacetyl)-(R)-N-[1-(4-hydroxyphenyl)ethyl]-arginine amide;
(R)-N²-[(R,S)-2-(4-hydroxyphenyl)phenylacetyl]-(R)-N-[1-(4-hydroxy-phenyl)ethyl]arginine amide;
(R)-N'-(ethyl)-N²-(diphenylacetyl)-(R)-N-[1-(4-methoxyphenyl)ethyl]-arginine amide;
(R)-N'-(benzyl)-N²-(diphenylacetyl)-(R)-N-[1-(4-methoxyphenyl)ethyl]-arginine amide;
(R)-N'-(1-(4-hydroxyphenyl)ethyl)-N²-(diphenylacetyl)-(R)-N-[1-(4-hydroxyphenyl)ethyl]arginine amide;
(R)-N²-(diphenylacetyl)-(R,S)-N-[1-(4-(aminocarbonylmethyl)phenyl)ethyl]-arginine amide;
(R)-N²-(diphenylacetyl)-(R,S)-N-[1-(4-(aminocarbonylaminomethyl)-phenyl)ethyl]arginine amide;
(R)-N²-(4,4'-dichlorodiphenylacetyl)-(R, S)-N-[1-(4-(aminocarbonylmethyl)-phenyl)ethyl]arginine amide; and
(R)-N²-(4,4'-dichlorodiphenylacetyl)-(R,S)-N-[1-(4-(aminocarbonylamino-methyl)phenyl)ethyl]arginine amide.

Particularly preferred compounds of the invention include:
(R)-N²-(diphenylacetyl)-(R)-N-[1-(4-methoxyphenyl)ethyl]arginine amide;
(R)-N²-(diphenylacetyl)-(R)-N-[1-(4-hydroxyphenyl)ethyl]arginineamide;
(R)-N²-[(R,S)-2-(4-chlorophenyl)phenylacetyl]-(R)-N-[1-(4-hydroxy-phenyl)ethyl]arginine amide;
(R)-N²-(4,4'-dichlorodiphenylacetyl)-(R)-N-[1-(4-hydroxyphenyl)ethyl]-arginine amide; and
(R)-N²-[(R,S)-2-(4-hydroxyphenyl)phenylacetyl]-(R)-N-[1-(4-hydroxy-phenyl)ethyl]arginine amide.

PREPARATION

According to the invention there is also provided a process for the preparation of compounds of formula I which comprises:

(a) Preparation of a compound of formula I by reaction of a compound of formula II,

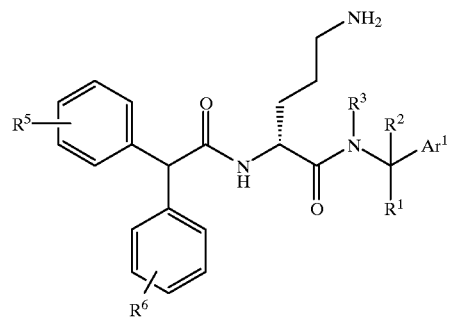

Wherein $Ar^1$, $R_1$, $R^2$ $R^3$, $R^5$ and $R^6$ are as hereinbefore defined with a compound of formula III, $$R^aSC(=NR^4)NH_2 \qquad III$$

or a hydrogen sulphate salt thereof, wherein $R^a$ represents $C_{1-4}$ alkyl (e.g. methyl) and $R^4$ is as hereinbefore defined, for example at room temperature in the presence of a suitable base (e.g. DiPEA or triethylamine) and an appropriate organic solvent (e.g. DMF, THF or a mixture thereof).

(b) Preparation of a compound of formula I, wherein $R^4$ represents H, by reaction of a compound of formula II as hereinbefore defined with 1H-pyrazole-1-carboxamidine, or a hydrohalide salt thereof, for example at room temperature in the presence of a suitable base (e.g. DiPEA or triethylamine) and an appropriate organic solvent (e.g. DMF).

(c) Preparation of a compound of formula I by reaction of a compound of formula II as hereinbefore defined with a compound of formula IV, $$R^aOC(=NR^4)NH_2 \qquad IV$$

or a hydrogen sulphate salt thereof, wherein $R^a$ and $R^4$ are as hereinbefore defined, for example between room temperature and 70° C. in the presence of a suitable base (e.g. DiPEA or triethylamine) and an appropriate organic solvent (e.g. acetonitrile or DMF).

d) Preparation of a compound of formula I wherein $R^4$ represents H by reaction of a compound of formula II as hereinbefore defined with a compound of formula V,

V

HN\(\overset{S(O)_mH}{\diagdown}\)NH$_2$ wherein m represents 2 or 3, for example at room temperature to 70° C. in the presence of a suitable base (e.g. DiPEA or triethylamine) and an appropriate organic solvent (e.g. acetonitrile or DMF).

e) Preparation of a compound of formula I by reaction of a compound of formula VI,

VI

[structure with $R^b$, $R^5$, $R^3$, $R^2$, $R^1$, $Ar^1$, $R^6$]

wherein $R^b$ represents $C_{1-4}$ alkyl (e.g. methyl) and $Ar^1$, $R^1$, $R^2$, $R^3$, $R^5$ and $R^6$ are as hereinbefore defined with a compound of formula VII, $R^4NH_2$    VII wherein $R^4$ is as hereinbefore defined, for example at room temperature in the presence of an appropriate solvent (e.g. DMF).

f) Preparation of a compound of formula I by reaction of a compound of formula VIII,

VIII

[structure with $R^4$, $R^3$, $R^2$, $R^1$, $Ar^1$]

wherein $Ar^1$, $R^1$, $R^2$, $R^3$ and $R^4$ are as hereinbefore defined with a compound of formula IX,

IX

[structure with $R^5$, $NO_2$, $R^6$]

wherein $R^5$ and $R^6$ are as hereinbefore defined, for example between −10° C. and reflux (e.g. −10 to 30° C.) in the presence of a suitable base (e.g. triethylamine or DiPEA) and a suitable organic solvent (e.g. $CH_2Cl_2$).

g) Preparation of a compound of formula I by reaction of a compound of formula VIII, as hereinbefore defined, with a compound of formula X,

X

[structure with $R^5$, Cl, $R^6$]

wherein $R^5$ and $R^6$ are as hereinbefore defined, for example at or below room temperature in the presence of a suitable base (e.g. DiPEA, pyridine or sodium bicarbonate) and an appropriate organic solvent (e.g. THF, EtOAc or $CH_2Cl_2$, with or without trace DMF).

h) Preparation of a compound of formula I by reaction of a compound of formula VIII, as hereinbefore defined, with a compound of formula XI,

XI

[structure with $R^5$, OH, $R^6$]

wherein R⁵ and R⁶ are as hereinbefore defined, for example at or below room temperature in the presence of a suitable peptide coupling system (e.g. BOP reagent), base (e.g. triethylamine) and a suitable organic solvent (e.g. acetonitrile).

Compounds of formula II may be prepared by reaction of a compound of formula XII,

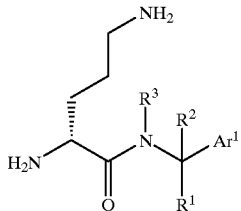

XII wherein Ar¹, R¹, R² and R³ are as hereinbefore defined with a compound of formula IX, as hereinbefore defined, for example under similar conditions to those described hereinbefore for compounds of formula I (process step (f)).

Compounds of formula II may alternatively be prepared by reaction of a compound of formula XII, as hereinbefore defined, with a compound of formula X, as hereinbefore defined, for example under similar conditions to those described hereinbefore for compounds of formula I (process step (g)).

Compounds of formula II may alternatively be prepared by reaction of a compound of formula XII, as hereinbefore defined, with a compound of formula XI, as hereinbefore defined, for example under similar conditions to those described hereinbefore for compounds of formula I (process step Compounds of formula VI may be prepared by reaction of a compound of formula XIII,

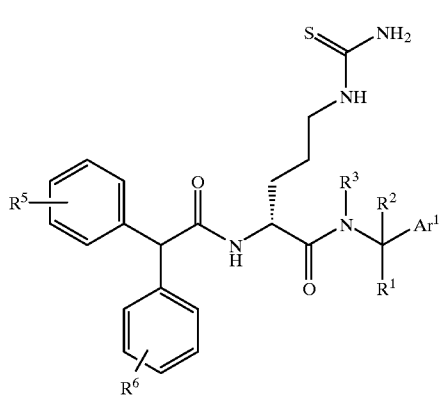

XIII wherein Ar¹, R¹, R², R³, R⁵ and R⁶ are as hereinbefore defined, with the appropriate alkyl iodide, for example at room temperature in the presence of an appropriate solvent system (e.g. $CH_2Cl_2$ or MeOH or mixtures thereof).

Compounds of formula VIII may be prepared by reaction of a compound of formula XII, as hereinbefore defined, with a compound of formula III (or a hydrogen sulphate salt thereof), 1H-pyrazole-1-carboxamidine (or a hydrohalide salt thereof), or a compound of formula IV (or a hydrogen sulphate salt thereof), for example as described hereinbefore for the synthesis of compounds of formula I (process steps (a), (b) and (c), respectively).

Compounds of formula XII may be prepared by reaction of a compound of formula XIV,

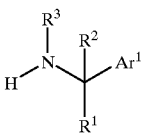

XIV wherein Ar¹, R¹, R² and R³ are as hereinbefore defined with (R)-ornithine, or a derivative thereof, for example at room temperature in the presence of a suitable peptide coupling system (e.g. BOP reagent and HOBT or EDC), base (e.g. DiPEA, triethylamine or diisopropylamine) and an appropriate organic solvent (e.g. acetonitrile, $CH_2Cl_2$ or a mixture thereof).

Compounds of formula XII may alternatively be prepared by reaction of a compound of formula XIV or a hydrohalide salt thereof as hereinbefore defined with (R)-ornithine 2-nitrophenyl ester, for example at room temperature in the presence of an appropriate organic solvent (e.g. $CH_2Cl_2$) and, if the compound of formula XIV is a salt, a suitable base (e.g. triethylamine or DiPEA).

Compounds of formula XIII may be prepared by reaction of a compound of formula II as hereinbefore defined with isothiocyanate, or a derivative (e.g. the benzoyl derivative) thereof, for example at room temperature in the presence of an appropriate organic solvent (e.g. $CH_2Cl_2$), followed by, for example, treatment with aqueous base (e.g. potassium carbonate) in the presence of an appropriate solvent such as MeOH.

Compounds of formula XIV are either commercially available, are known in the literature or are available using known techniques. For example compounds of formula XIV wherein R² and R³ both represent H may be prepared by reductive amination of a corresponding compound of formula XV,

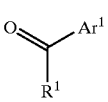

XV wherein Ar¹ and R¹ are as hereinbefore defined under conditions which are well known to those skilled in the art.

Optically active compounds of formula XIV may be isolated in accordance with known techniques, and may subsequently be used in the synthesis of corresponding compounds of formulae XII, II and I under conditions which will not cause racemisation or epimerisation such as those defined hereinbefore.

Compounds of formulae III, IV, V, VII, IX, X, XI, XV are either commercially available, are known in the literature or are available using known techniques, for example as described hereinafter.

Substituents on the aromatic group in compounds of formulae I, II, III, IV, VI, VII, VIII, IX, X, XI, XII, XIII, XIV and XV may be interconverted by techniques which are well known to those skilled in the art.

The compounds of the invention may be isolated from their reaction mixtures using conventional techniques.

It will be appreciated by those skilled in the art that, in the processes described above, the functional groups of intermediate compounds may need to be protected by protecting groups.

Functional groups which it is desirable to protect include hydroxy, amino, amidino, guanidino and carboxylic acid.

Suitable protecting groups for hydroxy include trialkylsilyl and diarylalkylsilyl groups (e.g. tertbutyldimethylsilyl, tertbutyldiphenylsilyl or trimethylsilyl) and tetrahydropyranyl. Suitable protecting groups for amino, amidino and guanidino include tertbutyloxycarbonyl, 9-fluorenylmethoxycarbonyl or benzyloxycarbonyl. Amidino and guanidino nitrogens may be either mono- or diprotected. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art and as described hereinafter.

Many protected derivatives of the intermediate compounds described hereinbefore are commercially available.

Persons skilled in the art will appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups. Accordingly, the order and type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", 2nd edition, T W Greene & P G M Wutz, Wiley-Interscience (1991).

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of the invention which are pharmacologically active. Such derivatives may therefore be described as "prodrugs".

All prodrugs of compounds of formula I are included within the scope of the invention.

Medical and Pharmaceutical Use

The compounds of the invention are useful because they possess pharmacological activity. They are therefore indicated as pharmaceuticals.

According to a further aspect of the invention there is thus provided the compounds of the invention for use as pharmaceuticals.

In particular, the compounds of the invention are potent antagonists of NPY for example as demonstrated in the tests described below.

The compounds of the invention are thus expected to be useful in the treatment of diseases/disorders which are/may be mediated by NPY, such as cardiovascular diseases.

The compounds of the invention are thus indicated for use in the treatment of coronary heart diseases such as angina pectoris, myocardial infarction and syndrome X as well as high blood pressure, hypertension and chronic heart insufficiency.

According to a further aspect of the invention, there is provided a method of treatment of a cardiovascular disease, which method comprises administration of a therapeutically effective amount of a compound of the invention to a person suffering from, or susceptible to, such a condition.

The compounds of the invention are also indicated for use in the treatment of other diseases in which NPY is thought to play a pathogenic role, such as chronic kidney failure, tumour diseases such as phaeochromocytoma, infections, migraine, hyperthyroidism as well as obesity and diabetes.

Compounds of the invention have been found to be selective antagonists of the NPY sub-receptor $Y_1$, for example as demonstrated in the tests described below.

The compounds of the invention thus find particularly utility in the inhibition of vasoconstriction and in disease states characterised thereby such as migraine, Horton's syndrome, Raynauld's disease, vasospasm after subarachnoid hemorrhage, angina pectoris, coronary infarction, heart failure, cardiac arrhythmias, hypertension, endotoxin shock and stroke.

According to a further aspect of the invention there is provided a method of treatment of vasoconstriction, which method comprises administration of a therapeutically effective amount of a compound of the invention, or a pharmaceutically acceptable derivative thereof, to a person suffering from, or susceptible to, such a condition.

Pharmaceutical Preparations

The compounds of the invention will normally be administered orally, intravenously, subcutaneously, buccally, rectally, dermally, nasally, tracheally, bronchially, by any other parenteral route or via inhalation, in the form of pharmaceutical preparations comprising the active ingredient either as a free base, or a pharmaceutical acceptable non-toxic organic or inorganic acid addition salt, in a pharmaceutically acceptable dosage form. Depending upon the disorder and patient to be treated and the route of administration, the compositions may be administered at varying doses.

The compounds of the invention may also be combined with other therapeutic agents which are useful in the treatment of cardiovascular disease, for example β-adrenoceptor antagonists, ACE-inhibitors, diuretics, and calcium antagonists.

According to a further aspect of the invention there is thus provided a pharmaceutical formulation including a compound the invention in admixture with a pharmaceutically acceptable adjuvant, diluent or carrier.

Suitable doses of the compounds of the invention in therapeutic treatment of humans are about 0.1–1 mg/kg body weight per day at peroral administration and 0.001–0.1 mg/kg body weight per minute at parenteral administration.

Compounds of the invention have been observed to have the advantage that they produce fewer side effects than compounds known in the abovementioned prior art.

Compounds of the invention may also have the advantage that they may be more efficacious, be less toxic, be longer acting, have a broader range of activity, be more potent, be more easily absorbed than, or that they may have other useful pharmacological properties over, compounds known in the prior art.

Biological Tests

Test A

Binding to NPY $Y_1/Y_2$ Receptors in vitro (a) Preparation of Receptor Containing Membranes (i) $Y_1$ receptors The main portion of the rat brain cortex was used for this preparation.

The rats (male or female Sprague-Dawley rats, weighing 150–250 g) were killed using $CO_2$ followed by bleeding. The brains were excised, and put in ice cold buffer (0.3 M sucrose, 5 mM Hepes; pH 7.4).

The material was diluted in 10 volumes of ice cold buffer, cut in smaller pieces, and homogenized first with a polytrone followed by 10 strokes at maximum speed with a Potter-Elvehjem homogenizer.

The homogenate was centrifuged at 650×g at 4° C. for 10 minutes. The supernatant was further centrifuged at 33 000×g at 4° C. for 19 minutes. The pellets were washed once by resolving them in buffer and repeating the last centrifugation step. The final pellets were resolved in a small volume (0.3–1 mL per gram tissue) of buffer complemented with 10% (v/v) glycerol. Aliquots (~200 μl) were quickly frozen in MeOH and dry ice, and stored at −80° C. until further use.

The protein concentration was determined according to Bradford (Anal. Biochem. (1976) 72, 248), using the Bio-Rad kit. The $Y_1$ preparation contained approximately 70–80% $Y_1$ receptors.

(ii) $Y_2$ receptors

This preparation was performed using pig spleen from a local slaughter house (Farmek Ekonomisk, Fbrening, Varberg, Sweden). The preparative procedure was the same as for the $Y_1$ receptor above. The resulting membranes contained approximately 80–90% $Y_2$ receptors.

(b) Receptor Binding Assay

In a typical experiment, 300 μg of $Y_1$ or $Y_2$ receptor containing membranes were mixed with $^3$H-NPY and test compound in different concentrations. Membranes and ligands were diluted in the assay buffer (137 mM NaCl, 2.7 mM KCl, 2.1 mM $MgCl_2$, 1.8 mM $CaCl_2$, 0.2% (w/v) bovine serum albumin, 20 mM Hepes; pH 7.4). The samples were incubated for 60 minutes at 30° C., and the binding reaction was stopped by putting the tubes on ice. The samples were filtered on glass fibre filters using a Millipore filtration manifold, to separate unbound and bound isotope labelled ligand. The radioactivity collected on the filters was determined by liquid scintillation counting.

Non specific binding (non NPY related binding) was estimated in the presence of a high concentration (0.1 μM) of unlabelled $NPY_1$ The difference between total binding (in the absence of NPY/test compound) and non specific binding was expressed as specific binding and is used at the maximal response in each experiment.

Test B

The Effects of Test Compounds on NPY in Anaesthetised Rats

Male Sprague-Dawley rats (300–450 g) from Charles River UK were used. The animals were initially anaesthetised with sodium pentobarbitone 70 mg/kg i.p. The anaesthesia was maintained by a continuous infusion in the tail artery (12–20 mg/kg/hour). Body temperature was measured by a rectal probe and maintained by means of a heating pad and a heating lamp at 37.5–38.0° C. The rats were tracheotomised (PE 240) to facilitate spontaneous breathing. Catheters (PE 25) were inserted in the right and left jugular veins for infusions of NPY and test compound. In the tail artery a catheter (PE 25) was inserted for measurement of blood pressure (BP) and for a continuous infusion of anaesthesia. Mean arterial pressure was measured with a transducer (156PC) and heart rate was measured from the pulsating arterial pressure signal with a rate-meter. The left renal artery was dissected free and a small probe was placed around the artery (Transonic 0.7 VB42) in order to measure renal blood flow.

All signals were recorded on a paper chart recorder (Grass Polygraph) and digitised using a standard PC. The sampling rate was 10 samples per second and the mean value was calculated and stored every 2 seconds. The computer program then calculated changes in mean arterial pressure, heart rate and renal blood flow from control values measured before drug administration.

After completion of the surgical preparation above, and a stabilisation-period of 30 minutes, NPY (4 μg/kg/20sec.) was intravenously administered at 20 minute intervals. After 2 stable readings following NPY administration, test compound was intravenously administered in increasing doses (0.625–40 μg/kg/min.) over 20 minutes. After 10 minutes, further NPY was administered. A test compound was considered active if it attenuated the cardiovascular effect of further NPY treatment in a dose dependent manner.

The invention is illustrated by way of the following examples.

EXAMPLES

General

Thin layer chromatography utilized silica gel with the following eluent systems: $CHCl_3$:MeOH:concentrated ammonium hydroxide (77:18:5) with EM Science No. 5714-3 plates (System A); MeOH:$CH_2Cl_2$ (1:9) with EM Science No. 5714-3 plates (System B); $CH_2Cl_2$:MeOH:concentrated ammonium hydroxide (88.5:10:1.5) with Whatman No. 4420 222 plates (System C); $CHCl_3$:MeOH:concentrated ammonium hydroxide (6:3:1) with Whatman No. 4420 222 plates (System D); [pyridine:HOAc:water (55:25:20)]:EtOAc (1:1) with Whatman No. 4420 222 plates (System E); [pyridine:HOAc:water (55:25:20)]:EtOAc (1:2) with Whatman No. 4420 222 plates (System F). Preparative TLC plates were Analtech Uniplate Silica Gel GF (20×20 cm, tapered layer; catalog #81013).

Example 1

(R)-$N^2$-(Diphenylacetyl)-(R)-N-[1-(4-methoxyphenyl)ethyl]arginine amide hydrochloride (a) (R)-$N^2$-(Boc)-$N^5$-(Cbz)-(R)-N-[1-(4-methoxyphenyl) ethyl]ornithine amide To a magnetically stirred suspension of $N^\alpha$-Boc$^\delta$-N-Cbz-(R)-ornithine (3.6 g; 9.9 mmol), BOP reagent (4.4 g; 9.9 mmol) and HOBT (1.3 g; 9.9 mmol) in 200 mL of acetonitrile:$CH_2Cl_2$ (1:1) was added DiPEA (5.2 mL; 30 mmol) at room temperature under nitrogen. After 5 minutes, all the solids dissolved. To the resultant solution was added (R)-4-methoxy-α-methylbenzylamine (1.5 g; 9.9 mmol) in $CH_2Cl_2$ (5 mL). The solution was stirred at room temperature for 2 hours, then concentrated at reduced pressure to give a thick oil. The residue was dissolved in 500 mL of EtOAc and washed successively with 5% aqueous citric acid solution (2×300 mL), water (300 mL), saturated aqueous $NaHCO_3$ (2×300 mL) and brine (2×300 mL). The organic layer was dried ($Na_2SO_4$), filtered and evaporated at reduced pressure to give 5.0 g (100%) of the sub-title compound as a light yellow solid.

$^1$H NMR (CD$_3$OD) 67 1.39 (s, 9H), 1.40–1.75 (m, 7H), 3.03–3.18 (m, 2H), 3.72 (s, 3H), 4.00–4.10 (m, 1H), 4.89–5.00 (m, 1H), 5.03 (s, 2H), 6.83 (d, 2H), 7.22 (d, 2H), 7.25–7.35 (m, 5H).

(b) (R)-$N^5$-(Cbz)-(R)-N-[1-(4-Methoxyphenyl)ethyl] ornithine amide hydrochloride (R)-$N^2$-(Boc)-$N^5$-(Cbz)-(R)-N-[1-(4-methoxyphenyl) ethyl]ornithine amide (14.0 g; from step (a) above) in EtOAc (300 mL) was treated with EtOAc saturated with hydrogen chloride (HCl/EtOAc; 300 mL) at room temperature for 5 hours. The solution was concentrated to give the crude sub-title compound as a crushable foam (12.9 g) which was used without purification.

$^1$H NMR (CD$_3$OD) 67 1.45 (d, 3H), 1.70–1.90 (m, 4H), 3.08 (t, 2H), 3.74 (s, 3H), 3.87 (m, 1H), 5.01 (m, 1H), 5.06 (s, 2H), 6.87 (d, 2H), 7.27 (d, 2H), 7.30–7.48 (m, 5H).

(c) 2-Nitrophenol diphenyl acetate

A solution of diphenylacetic acid (30.0 g; 141 mmol) and o-nitrophenol (39.3 g; 282 mmol) in pyridine (250 mL) was cooled to 0° C. N,N$^1$-dicyclohexylcarbodiimide (27.6 g; 134 mmol) was added at 0° C. The solution was stirred at 0° C. for several hours, warmed to room temperature and stirred overnight. The resulting heterogeneous solution was diluted with EtOAc and filtered. The filtrate was concentrated to afford a thick oil which was dissolved in a minimal amount of warm isopropanol. Upon cooling the sub-title compound began to crystallize from solution. The crystals were collected and dried under vacuum to afford the sub-title compound (37.3 g; 82%) as an off-white powder.

mp 83–85° C.

$^1$H NMR (CDCl$_3$) 67 5.38 (s, 1H), 7.14 (d, 1H), 7.20–7.45 (m, 11H), 7.60 (t, 1H), 8.07 (d, 1H).

(d) (R)-N$^5$-(Cbz)-N$^2$-(Diphenylacetyl)-(R)-N-[1-(4-methoxyphenol)ethyl]-ornithine amide (R)-N$^5$-(Cbz)-(R)-N-[1-(4-methoxyphenyl)ethyl] ornithine amide hydrochloride (12.9 g; 29.6 mmol; from step (b) above) and 2-nitrophenyl diphenyl acetate (9.5 g; 29.6 mmol; from step (c) above) were combined in CH$_2$Cl$_2$ (600 mL). Triethylamine (4.5 g; 44.4 mmol) was added. The resulting yellow solution was stirred at room temperature for 60 hours. When the coupling was complete, as determined by TLC, one volume of 0.5 N NaOH was added and the solution stirred for several minutes. The organic layer was separated and the aqueous layer extracted twice more with CH$_2$Cl$_2$. The combined organics were washed with brine, dried over anhydrous sodium sulfate, filtered and concentrated under vacuum to give the crude product as a light yellow solid (16.6 g). The product was dissolved in a mixture of CH$_2$Cl$_2$, MeOH and EtOAc and concentrated until solids formed. The solids were collected and dried to give pure product as a white solid (3.2 g). The filtrate was concentrated to give a solid which was chromatographed on silica gel using EtOAc:CH$_2$Cl$_2$ (1:3) as eluent. Concentration of the appropriate fractions gave additional pure product as a white solid (8.8 g).

R$_f$ 0.3 (EtOAc:CH$_2$Cl$_2$ (1:3); silica gel TLC plate) $^1$H NMR (CDCl$_3$) 67 1.38 (d, 3H), 1.20–1.58 (m, 2H), 1.62–1.80 (m, 2H), 3.03 (m, 1H), 3.32 (m, 1H), 3.72 (s, 3H), 4.68 (m, 1H), 4.80–5.08 (m, 4H), 6.72 (d, 1H), 6.78 (d, 2H), 7.02–7.45 (m, 17H).

(e) (R)-N$^2$-(Diphenylacetyl)-(R)-N-[1-(4-methoxyphenyl) ethyl]ornithine amide

A solution of (R)-N$^5$-(Cbz)-N$^2$-(Diphenylacetyl)-(R)-N-[1-(4-methoxy-phenyl)ethyl]ornithine amide (5.7 g; 9.6 mmol; from step (d) above) and HCl (2 N; 6 mL) in MeOH (200 mL) was flushed with nitrogen prior to the addition of 10% Pd/C (w/w; 530 mg). The heterogeneous solution was briefly flushed with hydrogen and then stirred under 1 atmosphere of hydrogen for 3 hours. When the deprotection was complete, as determined by TLC analysis, the solution was filtered through a pad of Celite to remove the catalyst. The filtrate was then evaporated at reduced pressure to give the crude product. The residue from evaporation of the filtrate was dissolved in water (300 mL) and washed with diethyl ether (2×50 mL). The aqueous layer was adjusted to pH 12 with concentrated NH$_4$OH, then extracted with EtOAc (3×200 mL). The combined organic extracts were washed with brine (200 mL), then dried (Na$_2$SO$_4$) and filtered. The filtrate was evaporated at reduced pressure to give 4.2 g (95%) of the sub-title compound (free base) as a white solid.

$^1$H NMR (CD$_3$OD) 67 1.30–1.48 (m, 2H), 1.35 (d, 3H), 1.50–1.80 (m, 2H), 2.52 (t, 2H), 3.72 (s, 3H), 4.32-4.42 (m, 1H), 4.85–4.95 (m, 1H), 5.05 (s, 1H), 6.82 (d, 2H), 7.18 (d, 2H), 7.20–7.30 (m, 10H).

(f) (R)-N$^\omega$, N$^{\omega'}$-bis(Cbz)-N$^2$-(Diphenylacetyl)-(R)-N-[1-(4-methoxy-phenyl)ethyl]arginine amide (R)-N$^2$-(Diphenylacetyl)-(R)-N-[1-(4-methoxyphenyl) ethyl]ornithine amide (free base from step (e) above; 3.26 g; 7.09 mmol) in DMF (35 mL) was treated with N,N$^1$-bis (Cbz)-S-methylisothiourea (2.80 g, 7.80 mmol) and stirred for 60 hours. Concentration under vacuum gave the crude product (5.7 g of a crushable foam) which was chromatographed on silica gel eluting with CH$_2$Cl$_2$, then EtOAc to give pure sub-title compound as a white, crushable foam (5.4 g).

R$_f$ 0.4 (CH$_2$Cl$_2$:EtOAc (3:1); silica gel TLC plate)

$^1$H NMR (CDCl$_3$) 67 1.34 (d, 3H), 1.25–1.68 (m, 3H), 1.78 (m, 1H), 3.12–3.45 (m, 2H), 3.78 (s, 3H), 4.47 (m, 1H), 4.88–5.10 (m, 4H), 5.18 (s, 2H), 6.67 (d, 1H), 6.83 (d, 2H), 6.95–7.45 (m, 22H), 8.30 (m, 1H).

(g) (R)-N$^2$-(Diphenylacetyl)-(R)-N-[1-(4-methoxyphenyl) ethyl]arginine amide hydrochloride (R)-N$^\omega$,N$^{\omega'}$-bis(Cbz)-N$^2$-(diphenylacetyl)-(R)-N-[1-(4-methoxyphenyl)ethyl]-arginine amide (5.40 g; 7.10 mmol; from step (f) above) in HOAc (300 mL) was flushed with nitrogen prior to the addition of 10% Pd/C (w/w; 1.10 g). The heterogeneous solution was briefly flushed with hydrogen and then stirred under 1 atmosphere of hydrogen for 4 hours. When the deprotection was complete, as determined by TLC analysis, the solution was filtered through a pad of Celite to remove the catalyst. The filtrate was evaporated at reduced pressure to give the crude product. The crude acetate salt was dissolved in HCl/MeOH, treated with activated carbon, filtered, concentrated, and dried under vacuum at 55–60° C. for 5 hours to give the sub-title compound as an off-white solid (3.47 g).

mp 115–120° C.

R$_f$ 0.4 (System D)

$[\alpha]_D^{25}$=+53.2° (c=0.98, MeOH)

$^1$H NMR (CD$_3$OD) 67 1.38 (d, 3H), 1.25–1.87 (m, 4H), 2.98–3.17 (m, 2H), 3.77 (s, 3H), 4.41 (m, 1H), 4.92 (m, 1H), 5.14 (s, 1H), 6.84 (d, 2H 7.08–7.45 (m, 12H).

$^{13}$C NMR (CD$_3$OD) δ23.8, 26.8, 30.5, 42.0, 49.8, 55.0, 56.2, 59.0, 115.2, 128.5, 129.8, 130.2, 137.2, 141.4, 158.8, 160.5, 173.0, 175.2.

Example 2

(R)-N$^2$-(Diphenylacetyl)-(R S)-N-(1-phenylpropyl) arginine amide hydrochloride (a) (R)-N$^2$-(Boc)-N$^5$-(Cbz)-(R,S)-N-(1-phenylpropyl) ornithine amide Prepared according to the method described in Example 1(a) above from N$^\alpha$-Boc-N$^\delta$-Cbz-(R)-ornithine (4.1 g; 11 mmol), BOP reagent (4.9 g; 11 mmol), HOBT (2.9 g; 22 mmol) and DiPEA (12 mL; 67 mmol) in acetonitrile (200 mL; instead of acetonitrile:CH$_2$Cl$_2$ (1:1)) followed by (R,S)-α-ethylbenzylamine (1.5 g; 11 mmol). Work up yielded the sub-title compound (5.4 g) as a thick oil which solidified upon standing.

$^1$H NMR (CDCl$_3$) 67 0.80–0.95 (m, 3H), 1.30–1.65 (m, 4H), 1.38+1.40 (s, 9H), 1.70–1.90 (m, 2H), 3.02–3.20+ 3.0–3.45 (m, 2H), 4.10–4.30 (m, 1H), 4.25–5.25 (m, 3H), 6.75–6.88 (m, 1H), 7.18–7.42 (m, 10H).

(b) (R)-N$^5$-(Cbz)-(R,S)-N-(1-phenylpropyl)ornithine amide hydrochloride (R)-N$^2$-(Boc)-N$^5$-(Cbz)-(R,S)-N-(1-phenylpropyl) ornithine amide (5.4 g; 11 mmol; from step (a) above) was suspended in EtOAc (30 mL) and HCl/EtOAc (100 mL) was added. The mixture was magnetically stirred at room temperature for 1 hour, then evaporated at reduced pressure to give the crude sub-title compound as a thick oil, which was suitable for use in the next step without purification.

(c) (R)-N$^5$-(Cbz)-N$^2$-(Diphenylacetyl)-(R,S)-N-(1-phenylpropyl)ornithine amide The crude (R)-N$^5$-(Cbz)-(R,S)-N-(1-phenylpropyl) ornithine amide hydrochloride (from step (b) above) was dissolved in CH$_2$Cl$_2$ (100 mL) and diphenylacetyl chloride (2.5 g; 12 mmol) was added as a solid. The flask was cooled in an ice/water bath, magnetically stirred, and DiPEA (6.0 mL; 33 mmol) was added dropwise under nitrogen over 1 minute. The mixture was warmed to room temperature and stirred at that temperature for 1.5 hours. The solution was diluted with 100 mL of CH$_2$Cl$_2$ and washed successively with aqueous saturated KHSO$_4$ (200 mL), water (200 mL), aqueous saturated NaHCO$_3$ (200 mL) and brine (150 mL), then dried (Na$_2$SO$_4$), filtered and evaporated at reduced pressure to give the sub-title compound (4.9 g; 77%) as a tan solid.

$^1$H NMR (CDCl$_3$) 67 0.72–0.89 (m, 3H), 1.25–1.90 (m, 6H), 2.92–3.15+3.25–3.44 (m, 2H), 4.58–5.12 (m, 4H), 6.50–6.70 (m, 1H), 7.00–7.40 (m, 20H).

(d) (R)-N$^2$-(Diphenylacetyl)-(R,S)-N-(1-phenylpropyl) ornithine amide

Prepared according to the method described in Example 1(e) above from (R)-N$^5$-(Cbz)-N$^2$-(diphenylacetyl)-(R,S)-N-(1-phenylpropyl)ornithineamide (2.5 g; from step (c) above), 10% Pd/C (150 mg), 50 mL of MeOH (no HCl was added), 2.5 hours reaction time, affording the sub-title compound (1.8 g; 95%; free base) as a pale white solid.

R$_f$ 0.55 and 0.48 (System A)
$^1$H NMR (CD$_3$OD) 67 0.75–0.90 (m, 3H), 1.30–1.90 (m, 6H), 2.10–2.30 (br s, 2H), 2.50–2.70 (m, 2H), 4.35–4.50 (m, 1H), 4.60–4.72 (m, 1H), 5.00+5.10 (s, 1H), 7.10–7.40 (m, 15H).

(e) (R)-N$^2$-(Diphenylacetyl)-(R,S)-N-(1-phenylpropyl) ornithine amide hydrochloride A sample of (R)-N$^2$-(diphenylacetyl)-(R,S)-N-(1-phenylpropyl)ornithine amide (from step (d) above) was treated with HCl/EtOAc then evaporated at reduced pressure to constant weight to give a sample of the sub-title hydrochloride.

mp 170–180° C. (dec.)
$^1$H NMR (CD$_3$OD) 67 0.75–0.90 (m, 3H), 1.45–1.95 (m, 6H), 2.75–2.95 (m, 2H), 4.35–4.52 (m, 1H), 4.62–4.75 (m, 1H), 5.03+5.10 (s, 1H), 7.10–7.40 (m, 15H), 8.15–8.30 (m, 1H), 8.35–8.50 (m, 1H).

(f) (R)-N$^2$-(Diphenylacetyl)-(R,S)-N-(1-phenylpropyl) arginine amide hydrochloride The title compound was prepared analogously to a literature procedure (J. Org. Chem., 57, 2497 (1992)). A mixture of (R)-N$^2$-(diphenylacetyl)-(R,S)-N-(1-phenylpropyl) ornithine amide (0.78 g; 1.8 mmol; free base), 1H-pyrazole-1-carboxamidine mono hydrochloride (0.27 g; 1.8 mmol) and DiPEA (1.2 mL; 7.0 mmol) in 3 mL of dry DMF was magnetically stirred under nitrogen for 18 hours. The resultant solution was diluted with 40 mL of CH$_2$Cl$_2$ and diethyl ether was added dropwise until the solution turned slightly cloudy. The solution was scratched to induce solid formation and the resultant solids were filtered, rinsed with CH$_2$Cl$_2$ and diethyl ether and then dried at 40° C. under vacuum to give 300 mg (33%) of the title hydrochloride as a white solid.

mp 112–114° C.
R$_f$=0.24 (System A)
$^1$H NMR (CD$_3$OD) 67 0.75–0.90 (m, 3H), 1.40–1.90 (m, 6H), 3.06–3.10+3.10–3.20 (m, 2H), 4.40–4.50 (m, 1H), 4.60–4.70 (m, 1H), 5.05+5.10 (s, 1H), 7.15–7.88 (m, 15H).

Example 3

(R)-N$^2$-(Diphenylacetyl)-(R,S)-N-[1-(4-hydroxyphenyl)ethyl]arginine amide hydrochloride (a) (R)-N$^2$-(Boc)-N$^5$-(Cbz)-(R,S)-N-[1-(4-hydroxyphenyl) ethyl]ornithine amide Prepared according to the method described in Example 1(a) above from N$^\alpha$-Boc-N$^\delta$-Cbz-(R)-ornithine (5.00 g, 13.6 mmol), (R,S)-4-hydroxy-α-methylbenzyl-amine (1.87 g, 13.6 mmol), BOP (9.0 g, 20.3 mmol) and triethylamine (2.5 mL; instead of DiPEA) in acetonitrile (100 mL; instead of acetonitrile:CH$_2$Cl$_2$ (1:1)) to yield the sub-title compound (6.12 g) as a white foam. The NMR spectrum for this material was consistent with a mixture of diastereomers.

(b) (R)-N$^5$-(Cbz)-(R,S)-N-[1-(4-Hydroxyphenyl)ethyl] ornithine amide hydrochloride Prepared according to the method described in Example 1(b) above from (R)-N$^2$-(Boc)-N$^5$-(Cbz)-(R,S)-N-[1-(4-hydroxyphenyl)ethyl]ornithine amide (6.1 g; from step (a) above), EtOAc (150 mL) and HCl/EtOAc (150 mL) yielding the sub-title compound (8.6 g) as a white foam. The NMR data for this compound was consistent with a mixture of diastereomers.

(c) (R)-N$^5$-(Cbz)-N$^2$-(Diphenylacetyl)-(R,S)-N-[1-(4-hydroxyphenyl)ethyl]-ornithine amide (R)-N$^5$-(Cbz)-(R,S)-N-[1-(4-hydroxyphenyl)ethyl] ornithine amide hydrochloride (6.0 g; 14.2 mmol; from step (b) above) was treated with diphenylacetic acid (3.32 g; 15.6 mmol), BOP (6.92 g; 15.6 mmol) and triethylamine (4.36 mL; 31.3 mmol) in 300 mL of acetonitrile. The reaction mixture was subjected to aqueous work up and the crude product was chromatographed on 100 g of silica gel eluting with EtOAc:hexanes (2:1), to afford the sub-title compound (4.1 g) as a white foam. The NMR for this compound was consistent with a mixture of diastereomers.

(d) (R)-N$^2$-(Diphenylacetyl)-(R,S)-N-[1-(4-hydroxyphenyl) ethyl]ornithine amide Prepared according to the method described in Example 1(e) above from (R)-N$^5$-(Cbz)-N$^2$-(diphenylacetyl)-(R,S)-N-[1-(4-hydroxyphenyl)ethyl]-ornithine amide (4.1 g; from step (c) above), 10% Pd/C (1.2 g), MeOH (300 mL) and concentrated HCl (1 mL; instead of 2 N HCl), affording the sub-title compound (1.9 g) as a white solid. The NMR of this material was consistent with a mixture of diastereomers.

(e) (R)-N$^2$-(Diphenylacetyl)-(R,S)-N-[1-(4-hydroxyphenyl) ethyl]arginine amide hydrochloride Prepared according to the method described in Example 2(f) from (R)-N$^2$-(diphenylacetyl)-(R,S)-N-[1-(4-hydroxyphenyl)ethyl]ornithine amide(free base; 150 mg; 0.311 mmol; from step (d) above), 1H-pyrazole-1-carboxamidine mono hydrochloride (45.6 mg, 0.311 mmol) and DiPEA (0.06 mL; 0.622 mmol) in 2 mL of dry DMF. The reaction mixture was concentrated and the residue was applied to a preparative TLC plate and eluted with CH$_2$Cl$_2$:MeOH (90:10) to give the title compound (50 mg). The NMR of this material was consistent with a mixture of diastereomers.

$^1$H NMR (CD$_3$OD) 67 1.36 (d, 3H), 1.9–1.36 (m, 4H), 3.15 (m, 2H), 4.40 (m, 1H), 4.86 (m, 1H), 5.06+5.11 (s, 1H), 6.68 (d, 2H), 6.70 (d, 2H), 7.03 (d, 2H), 7.06 (d, 2H) 7.29 (m, 10H)

Example 4

(R)-N$^2$-(Diphenylacetyl)-(R)-N-[1-(4-hydroxyphenyl)ethyl]arginine amide hydrochloride (a) N$^\alpha$-Boc-N$^\delta$-Cbz-(R)-ornithine o-nitrophenyl ester A solution N$^\alpha$-Boc-N$^\delta$-Cbz-(R)-ornithine (25.0 g; 68.2 mmol) and o-nitrophenol (19.0 g; 136.4 mmol) in pyridine (250 mL) was cooled to 0° C. Dicyclohexylcarbodiimide (13.4 g; 64.8 mmol) was added at 0° C. The solution was stirred at 0° C. for several hours, warmed to room temperature and stirred overnight. The resulting heterogeneous solution was diluted with EtOAc and filtered. The filtrate was concentrated under reduced pressure to afford a thick oil. The oil was dissolved in a minimal amount of warm isopropanol and stirred. The resultant precipitate was collected via vacuum filtration and washed with isopropanol, then diethyl ether. Concentration of the isopropanol/ether filtrate and crystallization from isopropanol provided a second crop. The combined product was dissolved in EtOAc at room temperature and filtered. Concentration of the EtOAc gave the sub-title compound as a solid.

mp 96–98° C.

$^1$H NMR (CD$_3$OD) 67 1.48 (s, 9H), 1.60–1.90 (m, 4H), 2.00–2.15 (m, 1H), 3.22 (t, 2H), 4.35–4.42, (m, 1H), 5.08 (s, 2H), 7.20–7.38 (m, 6H), 7.49 (t, 1H), 7.76 (t, 1H), 8.12 (d, 1H).

(b) (R)-N$^2$-(Boc)-N$^5$-(Cbz)-(R)-N-[1-(4-hydroxyphenyl)ethyl]ornithine amide

N$^α$-Boc-N$^δ$-Cbz-(R)-ornithine o-nitrophenyl ester (33 g; 66.8 mmol; from step (a) above) and (R)-4-hydroxy-α-methylbenzylamine (9.3 g; 68.2 mmol) were combined in CH$_2$Cl$_2$ (600 mL). The resulting yellow solution was stirred at room temperature for 4 hours. When the coupling was complete, as determined by TLC, the solution was concentrated under vacuum to give the crude product. The crude material was dissolved in EtOAc, washed with 0.5N NaOH (2×300 mL), saturated KHSO$_4$ (2×300 mL), brine (2×300 mL), dried over Na$_2$SO$_4$, filtered and concentrated to yield 30.1 g (61.9 mmol; 93%) of the sub-title compound.

mp 64–105° C.

$[α]_D^{22}$=+50.2° (c=1.0, MeOH)

R$_f$ 0.29 (2:1 EtOAc/hexanes; silica gel TLC plate)

MS 486 m/z $^1$H NMR (CD$_3$OD) 67 1.45 (s, 9H), 1.75–1.49 (m, 7H), 3.08 (m, 2H), 4.05 (m, 1H), 4.93 (m, 1H), 5.05 (m, 2H), 6.65 (m, 1H, NH), 6.72 (d, 2H), 6.95 (m, 1H, NH), 7.11 (d, 2H), 7.33 (m, 5H), 8.12 (d, 1H, NH)

(c) (R)-N$^5$-(Cbz)-(R)-N-[1-(4-hydroxyphenyl)ethyl]ornithine amide hydrochloride Prepared according to the method described in Example 1(b) above from (R)-N$^2$-(Boc)-N$^5$-(Cbz)-(R)-N-[1-(4-hydroxyphenyl)ethyl]ornithine amide (30.1 g; 61.98 mmol; from step (b) above), EtOAc (250 mL) and HCl/EtOAc (150 mL) yielding (after chromatography on silica gel, eluting with CH$_2$Cl$_2$:MeOH (80:20)) the sub-title compound (15.5 g; 60%).

mp 200–203° C.

$[α]_D^{21}$+39.7° (c=1.0, MeOH)

MS 386 m/z

R$_f$ 0.28 (CH$_2$Cl$_2$/MeOH (80:20))

$^1$H NMR (CD$_3$OD) 67 1.48 (d, 3H), 1.89–1.48 (m, 4H), 3.09 (t, 2H), 3.80 (m, 1H), 5.05 (s, 2H), 4.95 (m, 1H), 6.83 (d, 2H), 7.15 (d, 2H), 7.33 (m, 5H)

(d) (R)-N$^5$-(Cbz)-N$^2$-(Diphenylacetyl)-(R)-N-[1-(4-hydroxyphenyl)ethyl]-ornithine amide (R)-N$^5$-(Cbz)-(R)-N-[1-(4-hydroxyphenyl)ethyl]ornithine amide hydrochloride (28.1 g; 66.6 mmol; from step (c) above) was dissolved in THF (500 mL) and solid sodium bicarbonate (22.4 g; 266.4 mmol; 4 eq.) was slowly added. A solution of diphenylacetylchloride (21.4 g; 66.60 mmol) in THF was then slowly added dropwise over 30 minutes. The reaction was monitored by TLC analysis. After the reaction was judged complete, the solvent was removed under vacuum and the residue was dissolved in a mixture of THF, EtOAc and MeOH and washed with saturated aqueous sodium bicarbonate, water, saturated KHSO$_4$ and brine. The organics were dried over Na$_2$SO$_4$, filtered and concentrated to dryness to yield 29.2 g (0.050 mol; 76%) of the sub-title compound.

mp 171–175° C.

$[α]_D^{22}$+15.1° (c=1.0, DMF)

R$_f$ 0.68 (CH$_2$Cl$_2$:MeOH (80:20); silica gel TLC plate)

$^1$H NMR (CD$_3$OD) δ1.35 (d, 3H), 1.42 (m, 2H), 1.60 (m, 1H), 1.74 (m, 1H), 3.03 (m, 2H), 4.39 (m, 1H), 4.95 (m, 1H), 5.02 (s, 2H), 5.08 (s, 1H), 6.71 (d, 2H), 6.80 (m, 1H, NH), 7.10 (d, 2H), 7.3 (m, 15H), 8.1 (d, 1H, NH)

(e) (R)-N$^2$-(Diphenylacetyl)-(R)-N-[1-(4-hydroxyphenyl)ethyl]ornithine amide acetate Prepared analogously to the method described in Example 1(e) above from (R)-N$^5$-(Cbz)-N$^2$-(diphenylacetyl)-(R)-N-[1-(4-hydroxyphenyl)ethyl]-ornithine amide (26.8 g; 46.23 mmol; from step (d) above), 10% Pd/C (2.5 g) and HOAc (1L; as opposed to HCl/MeOH) yielding 24.3 g of the sub-title compound (after azeotroping with toluene).

mp 120–145° C. (with decomposition)

$[α]_D^{23}$+57.1° (c=1.0, MeOH)

MS 446 m/z

R$_f$ 0.11 (System B)

$^1$H NMR (CD$_3$OD) 67 1.35 (d, 3H), 1.61 (m, 3H), 1.80 (m, 1H), 1.95 (s, 3H, HOAc), 2.81 (t, 2H), 4.40 (m, 1H), 5.09 (s, 1H), 6.71 (d, 2H), 7.08 (d, 2H), 7.28 (m, 10H)

(f)(R)-N$^{107}$, N$^{ω'}$-bis(Cbz)-N$^2$-(Diphenylacetyl)-(R)-N-[1-(4-hydroxyphenyl)-ethyl]arginine amide Prepared analogously to the method described in Example 1(f) above from (R)-N$^2$-(diphenylacetyl)-(R)-N-[1-(4-hydroxyphenyl)ethyl]ornithine amide acetate (5.5 g; 11.8 mmol; from step (e) above) and N,N$^1$-bis(Cbz)-S-methylisothiourea (6.14 g; 17.1 mmol), additionally using DiPEA (4.0 mL; 22.9 mmol) in 100 mL of DMF yielding 6.6 g of the sub-title compound as a white foam.

mp 58–74° C.

$[α]_D^{22}$=+35.3° (c=1.0 in MeOH)

R$_f$ 0.88 (EtOAc)

$^1$H NMR (CD$_3$OD) 67 1.31 (d, 3H), 1.40 (m, 2H), 1.55 (m, 1H), 1.59 (m, 1H), 3.19 (m, 2H), 4.40 (m, 1H), 4.81 (q, 1H), 5.05 (s, 1H), 5.06 (s, 2H), 5.18 (s, 2H), 6.69 (d, 2H), 7.05 (d, 2H), 7.4–7.1 (m, 20H).

(g) (R)-N$^2$-(Diphenylacetyl)-(R)-N-[1-(4-hydroxyphenyl)ethyl]arginine amide hydrochloride Prepared according to the method described in Example 1(g) above from (R)-N$^ω$,N$^{ω'}$-bis(Cbz)-N$^2$-(diphenylacetyl)-(R)-N-[1-(4-hydroxyphenyl)ethyl]-arginine amide (6.6 g; from step (f) above), HOAc (160 mL) and 10% Pd/C (w/w; 1.1 g) yielding 2.75 g of the title compound.

mp 150–153° C.

$[α]_D^{23}$=+57.4° (c=1.0, MeOH)

R$_f$ 0.44 (EtOAc:MeOH:concentrated ammonium hydroxide (47:47:6))

$^1$H NMR (CD$_3$OD) 67 1.38 (d, 3H), 1.50 (m, 2H), 1.69 (m, 1H), 1.79 (m, 1H), 3.09 (m, 2H), 4.39 (m, 1H), 4.86 (q, 1H), 5.11 (s, 1H), 6.71 (d, 2H), 7.09 (d, 2H), 7.25 (m, 10H), 8.15 (d, 1H, NH), 8.38 (d, 1H, NH).

Example 5

(R)-N$^2$-(Diphenylacetyl)-(S)-N-[1-(4-methoxyphenyl)ethyl]arginine amide hydrochloride (a) (R)-N$^2$-(Boc)-N$^5$-(Cbz)-(S)-N-[1-(4-methoxyphenol)ethyl]ornithine amide Prepared according to the method described in Example 4(b) above from N$^α$-Boc-N$^δ$-Cbz-(R)-ornithine o-nitrophenyl ester (14.0 g; 28.7 mmol) and (S)-4-methoxy- α-methylbenzylamine (5.0 g; 33.1 mmol) in CH$_2$Cl$_2$ (400 mL), 60 hours reaction time. The reaction mixture was submitted to aqueous work up using 0.5 N NaOH, brine, aqueous KHSO$_4$, and brine. The organic solution was dried, filtered and concentrated to give a solid (14.3 g) which was used without purification.

R$_f$ 0.50 (hexanes:EtOAc (3:7); silica gel TLC plate)

(b) (R)-N$^5$-(Cbz)-(S)-N-[1-(4-methoxyphenol)ethyl] ornithine amide hydrochloride Prepared according to the method described in Example 1(b) above from (R)-N$^2$-(Boc)-N$^5$-(Cbz)-(S)-N-[1-(4-methoxyphenyl)ethyl]ornithine amide (14.3 g; crude, from step (a) above), EtOAc (300 mL) and HCl/EtOAc (300 mL), 5 hours reaction time. The solution was concentrated to give the crude product as a crushable foam (13.3 g) which was used without purification.

$^1$H NMR (CD$_3$OD) 67 1.45 (d, 3H), 1.55–1.70 (m, 2H), 1.80–1.95 (m, 2H), 3.18 (t, 2H), 3.76 (s, 3H), 3.84 (m, 1H), 4.98 (m, 1H), 5.08 (s, 2H), 6.88 (d, 2H), 7.28 (d, 2H), 7.28–7.38 (m, 5H).

(c) (R)-N$^5$-(Cbz)-N$^2$-(Diphenylacetyl)-(S)-N-[1-(4-methoxyphenyl)ethyl]-ornithine amide Prepared according to the method described in Example 1(d) above from (R)-N$^5$-(Cbz)-(S)-N-[1-(4-methoxyphenyl) ethyl]ornithine amide hydrochloride (13.3 g; 30.5 mmol; from step (b) above) 2-nitrophenyl diphenyl acetate (9.8 g; 30.5 mmol; see Example 1(c) above), triethylamine (4.6 g; 45.8 mmol) and CH$_2$Cl$_2$ (600 mL), 60 hours reaction time. The reaction mixture was submitted to aqueous work up, dried, filtered and concentrated to give the crude product as a solid. The product was dissolved in CH$_2$Cl$_2$ and concentrated until solids began to form. Diethyl ether was added to precipitate more solids. The solids were collected and dried to give the sub-title compound as a white solid (13.5 g).

R$_f$ 0.3 (EtOAc:CH$_2$Cl$_2$ (1:3))

$^1$H NMR (CDCl$_3$) 67 1.38 (d, 3H), 1.35–1.62 (m, 2H), 1.72–1.80 (m, 2H), 3.09 (m, 1H), 3.34 (m, 1H), 3.78 (s, 3H), 4.58 (m, 1H), 4.75–5.12 (m, 4H), 6.56 (d, 1H), 6.78 (d, 2H), 6.90(d, 1H), 7.02–7.40 (m, 17H).

(d) (R)-N$^2$-(Diphenylacetyl)-(S)-N-[1-(4-methoxyphenyl) ethyl]ornithine amide

Prepared according to the method described in Example 1(e) above from (R)-N$^5$-(Cbz)-N$^2$-(diphenylacetyl)-(S)-N-[1-(4-methoxyphenyl)ethyl]-ornithine amide (6.3 g; 10.6 mmol; from step (c) above), 10% Pd/C (3.2 g), MeOH (500 mL) and concentrated HCl (20 mL) under hydrogen, 60 hours reaction time, to give the crude product as a solid (5.1 g). The solid was treated with ammonium hydroxide to afford the free base as a solid (4.7 g) which was chromatographed on silica gel eluting with CH$_2$Cl$_2$:MeOH (80:20). Concentration of the product containing fractions gave pure sub-title compound as a solid (3.2 g).

R$_f$ 0.4 (MeOH:ammonium hydroxide (30:1); silica gel TLC plate)

$^1$H NMR (CDCl$_3$) 67 1.08–1.47 (m, 5H), 1.62–1.88 (m, 2H), 2.47–2.72 (m, 2H), 3.78 (s, 3H), 4.48 (m, 1H), 4.92 (s, 1H), 4.97 (m, 1H), 6.78 (d, 2H), 6.95–7.45 (m, 12H).

(e) (R)-N$^ω$, N$^{ω'}$-bis(Cbz)-N$^2$-(Diphenylacetyl)-(S)-N-[1-(4-methoxy-phenyl)ethyl]arginine amide Prepared according to the method described in Example 4(f) above from (R)-N$^2$-(diphenylacetyl)-(S)-N-[1-(4-methoxyphenyl)ethyl]ornithine amide (free base; 1.75 g; 3.81 mmol; from step (d) above), N,N'-bis(Cbz)-S-methylisothiourea (1.50 g; 4.19 mmol) and dimethyl formamide (15 mL), 18 hours reaction time. Concentration under vacuum gave the crude product which was chromatographed on silica gel eluting with CH$_2$Cl$_2$, then with EtOAc, to give pure sub-title compound as a white solid (2.3 g).

R$_f$ 0.6 (hexane:EtOAc (3:7); silica gel TLC plate)

$^1$H NMR (CDCl$_3$) δ1.15–1.72 (m, 3H), 1.37 (d, 3H), 1.85 (m, 1H), 3.15–3.40 (m, 21H), 3.77 (s, 3H), 4.49 (m, 1H), 4.85–5.07 (m, 4H), 5.18 (s, 2H), 6.68–6.82 (m, 3H), 6.95–7.45 (m, 22H), 8.32 (m, 1H).

(f) (R)-N$^2$-(Diphenylacetyl)-(S)-N-[1-(4-methoxyphenyl) ethyl]arginine amide hydrochloride Prepared according to the method described in Example 1(g) above from (R)-N$^ω$,N$^{ω'}$-bis(Cbz)-N$^2$-(diphenylacetyl)-(S)-N-[1-(4-methoxyphenyl)ethyl]-arginine amide (2.8 g; from step (e) above), 10% Pd/C (1.5 g), and, instead of HOAc, MeOH (225 mL) and concentrated HCl (21 mL) under hydrogen, 18 hours reaction time, which gave the crude product (1.8 g). Crystallization from MeOH:diethyl ether then from isopropanol:diethyl ether afforded the sub-title compound as a white solid (0.75 g).

mp 148–153° C.

R$_f$ 0.3 (System D)

[α]$_D$$^{25}$=–9.7° (c=1.0, MeOH)

$^1$H NMR (CD$_3$OD) 67 1.38 (d, 3H), 1.45–1.92 (m, 4H), 3.15 (t, 2H), 3.78 (s, 3H), 4.43 (t, 1H),4.88 (m, 1H), 5.09 (s, 1H), 6.80 (d, 2H), 7.17 (d, 2H), 7.15–7.38 (m, 10H)

$^{13}$C NMR (CD$_3$OD) 67 23.0, 26.8, 30.4, 42.4, 55.0, 56.2, 59.0, 115.4, 128.4, 130.0, 130.4, 137.0, 141.2, 159.0, 160.6, 173.2, 175.4

Example 6

(R)-N$^2$-(Diphenylacetyl)-(S)-N-[1-(4-bromophenyl) ethyl]arginine amide hydrochloride (a)(R)-N$^2$-(Boc)-N$^5$-(Cbz)-(S)-N-[1-(4-bromophenyl)ethyl] ornithine amide Prepared according to the method described in Example 4(b) above from N$^α$-Boc-N$^δ$-Cbz-(R)-ornithine o-nitrophenyl ester (4.4 g; 9.1 mmol; see Example 1(c) above) and (–)-1-(4-bromophenyl)ethylamine (2.0 g; 10.0 mmol) in CH$_2$Cl$_2$, 18 hours reaction time. The product containing solution was concentrated under vacuum to give a yellow solid which was used without purification.

R$_f$ 0.40 (hexanes:EtOAc (3:7); silica gel TLC plate)

(b) (R)-N$^5$-(Cbz)-(S)-N-[1-(4-bromophenyl)ethyl]ornithine amide hydrochloride

Prepared according to the method described in Example 1(b) above from crude (R)-N$^2$(Boc)-N$^5$-(Cbz)-(S)-N-[1-(4-bromophenyl)ethyl]ornithine amide (9.1 mmol; from step (a) above), EtOAc (100 mL) and HCl/EtOAc (75 mL), 2 hours reaction time. The solution was concentrated to give the crude product as a yellow crushable foam (5.4 g) which was used without purification.

$^1$H NMR (CD$_3$OD) δ1.45 (d, 3H), 1.55–1.70 (m, 2H), 1.80–1.95 (m, 2H), 3.18 (t, 2H), 3.88 (t, 1H), 5.02 (m, 1H), 5.12 (s, 2H), 7.28 (d, 1H), 7.28–7.45 (m, 5H), 7.48 (d, 2H)

(c) (R)-N$^5$-(Cbz)-N$^2$-(Diphenylacetyl)-(S)-N-[1-(4-bromophenyl)ethyl]-ornithine amide Prepared according to the method described in Example 1(d) above from (R)-N$^5$-(Cbz)-(S)-N-[1-(4-bromophenyl) ethyl]ornithine amide hydrochloride (9.1 mmol; from step (b) above), 2-nitrophenyl diphenyl acetate (2.9 g; 9.1 mmol; see Example 1(c) above), triethylamine (3.7 g; 36.4 mmol) and CH$_2$Cl$_2$ (300 mL), 40 hours reaction time. The reaction mixture was submitted to aqueous work up, dried with Na$_2$SO$_4$ filtered and concentrated to give the crude product as a solid (6.1 g). The product was chromatographed on silica gel eluting with EtOAc:CH$_2$Cl$_2$ (1:3). Concentration of the appropriate fractions gave pure product as a white solid (4.2 g).

R$_f$ 0.3 (EtOAc: CH$_2$Cl$_2$ (1:3); silica gel TLC plate)

$^1$H NMR (CDCl$_3$) δ1.34 (d, 3H), 1.35–1.95 (m, 4H), 3.08 (m, 1H), 3.32 (m, 1H), 4.62 (m, 1H), 4.75–5.12 (m, 4H), 6.63 (d, 1H), 6.85–7.45 (m, 19H)

(d) (R)-N²-(Diphenylacetyl)-(S)-N-[1-(4-bromophenyl) ethyl]ornithine amide (R)-N⁵-(Cbz)-N²-(diphenylacetyl)-(S)-N-[1-(4-bromophenyl)ethyl]ornithine amide (0.50 g; 0.78 mmol; from step (c) above was suspended in $CH_2Cl_2$:acetonitrile (20 mL; 1:3) and was cooled to 0° C. Trimethylsilyl iodide (0.17 g, 0.86 mmol) was added at 0° C. and the reaction stirred for 2 hours at 0° C. (solids dissolving as the reaction proceeded). When the deprotection was complete, as determined by TLC analysis, the reaction was quenched with water and diluted with EtOAc. The organic layer was separated and washed with water (1×), 1 N sodium thiosulfate (1×) and brine (2×). The combined aqueous washings were extracted with $CH_2Cl_2$. The organics were combined and triethylamine (5 mL) was added. The mixture was allowed to stand for 18 hours, transferred to a separating funnel, washed with brine (3×), dried over anhydrous sodium sulfate, filtered and concentrated to give the crude product as a yellow solid (0.40 g). The crude product was chromatographed on silica gel eluting with MeOH:$CH_2Cl_2$ (3:7), then MeOH:$CH_2Cl_2$ (1:1), to give sub-title compound (free base) as an off-white solid (0.25 g).

$R_f$ 0.5 (System D)

¹H NMR ($CDCl_3$+$CD_3OD$) 67 1.41 (d, 3H), 1.30–1.54 (m, 2H), 1.63 (m, 1H), 1.78 (m, 1H), 2.70 (t, 2H), 4.43 (m, 1H), 4.88 (m, 1H), 4.99 (s, 1H), 7.08 (d, 2H), 7.18–7.42 (m, 12H)

(e) (R)-N²-(Diphenylacetyl)-(S)-N-[1-(4-bromophenyl) ethyl]arginine amide hydrochloride Prepared according to the method described in Example 2(f) above from (R)-N²-(diphenylacetyl)-(S)-N-[1-(4-bromophenyl)ethyl]ornithine amide (free base; 0.20 g; 0.39 mmol; from step (d) above), 1H-pyrazole-1-carboxamidine mono hydrochloride (0.06 g; 0.39 mmol), triethylamine (0.08 g; 0.78 mmol; instead of DiPEA) and dimethyl formamide (1 mL), 5 hours reaction time. The solution was concentrated under vacuum and the crude product chromatographed on silica gel eluting with MeOH:$CHCl_3$:ammonium hydroxide (3:6:1). Conversion of the eluted compound to the hydrochloride salt gave the title compound as a white solid (0.17 g).

mp 136–140° C.

$R_f$ 0.4 (System D)

$[\alpha]_D^{25}$ =−15.3° (c=1.0, MeOH)

¹H NMR ($CD_3OD$) 67 1.38 (d, 3H), 1.48–1.92 (m, 4H), 3.18 (t, 2H), 4.41 (m, 1H), 4.87 (m, 1H). 5.08 (s, 1H), 7.18 (d, 2H), 7.10–7.38 (m, 10H), 7.36 (d, 2H)

Example 7

(R)-N²-(Diphenylacetyl)-(R)-N-[1-(4-bromophenyl) ethyl]arginine amide hydrochloride (a)(R)-N²-(Boc)-N⁵-(Cbz)-(R)-N-[1-(4-Bromophenyl) ethyl]ornithine amide Prepared according to the method described in Example 4(b) above from $N^\alpha$-Boc-$N^\delta$-Cbz-(R)-ornithine o-nitrophenyl ester (2.2 g; 4.5 mmol; see Example 4(a) above) and (+)-1-(4-bromophenyl)ethylamine (1.0 g; 5.0 mmol) in $CH_2Cl_2$ (75 mL), 18 hours reaction time. The product containing solution was concentrated under vacuum to give a yellow solid which was used without purification.

$R_f$ 0.40 (hexanes:EtOAc (3:7); silica gel TLC plate)

(b) (R)-N⁵-(Cbz)-(R)-N-[1-(4-Bromophenyl)ethyl]ornithine amide hydrochloride

Prepared according to the method described in Example 1(d) above from crude (R)-N²-(Boc)-N⁵-(Cbz)-(R)-N-[1-(4-bromophenyl)ethyl]ornithine amide (2.46 g; 4.5 mmol; from step (a) above), EtOAc (75 mL) and HCl/EtOAc (50 mL), 2 hours reaction time. The solution was concentrated to give the crude product as a yellow crushable foam (2.4 g) which was used without purification.

¹H NMR ($CD_3OD$) δ1.48 (d, 3H), 1.65–1.90 (m, 4H), 3.12 (t, 2H), 3.90 (t, 1H), 5.00 (m, 1H), 5.08 (s, 2H), 7.25 (d, 2H), 7.25–7.40 (m, 5H), 7.48 (d, 2H).

(c) (R)-N⁵-(Cbz)-N²-(Diphenylacetyl)-(R)-N-[1-(4-bromophenyl)ethyl]-ornithine amide Prepared according to the method described in Example 1(d) above from (R)-N⁵-(Cbz)-(R)-N-[1-(4-bromophenyl) ethyl]ornithine amide hydrochloride (2.01 g; 4.5 mmol; from step (b) above) 2-nitrophenyl diphenyl acetate (1.4 g; 4.5 mmol; see Example 1(c) above), triethylamine (1.8 g; 18.0 mmol) and $CH_2Cl_2$ (300 mL), 40 hours reaction time. The reaction mixture was submitted to aqueous work up, dried with $Na_2SO_4$, filtered and concentrated to give the crude product as a solid (2.9 g). The product was chromatographed on silica gel eluting with EtOAc:$CH_2Cl_2$ (1:3). Concentration of the product containing fractions gave the sub-title compound as a white solid (2.5 g).

$R_f$ 0.3(EtOAc:$CH_2Cl_2$ (1:3); silica gel TLC plate)

¹H NMR ($CDCl_3$) δ1.35 (d, 3H), 1.20–1.98 (m, 4H), 3.03 (m, 1H), 3.32 (m, 1H), 4.71 (m, 1H), 4.80–5.12 (m, 4H), 6.68 (d, 1H), 7.05 (d, 2H), 7.12–7.50 (m, 17H)

(d) (R)-N²-(Diphenylacetyl)-(R)-N- [1-(4-bromophenyl) ethyl]ornithine amide

Prepared according to the method described in Example 6(d) above from (R)-N⁵-(Cbz)-N²-(diphenylacetyl)-(R)-N-[1-(4-bromophenyl)ethyl]ornithine amide (1.00 g; 1.56 mmol; from step (c) above), acetonitrile (30 mL), $CH_2Cl_2$ (10 mL) and trimethylsilyl iodide (0.34 g, 1.70 mmol), 1.5 hours reaction time, followed by additional trimethylsilyl iodide (0.14 g; 0.70 mmol), 0.5 hours reaction time. Work up using triethylamine (10 mL) gave the crude product as an oil (1.00 g). The product was chromatographed on silica gel eluting with MeOH, then with MeOH:ammonium hydroxide (30:1) to give pure sub-title compound (free base) as an off-white crushable foam (0.57 g).

$R_f$ 0.5(MeOH:ammonium hydroxide (30:1); silica gel TLC plate)

¹H NMR ($CD_3OD$) δ1.22–1.45 (m, 2H), 1.40 (d, 3H), 1.52–1.83 (m, 2H), 2.58 (t, 2H), 4.38 (m, 1H), 4.91 (m, 1H), 5.07 (s, 1H), 7.11–7.35 (m, 12H), 7.43 (d, 2H)

(e) (R)-N²-(Diphenylacetyl)-(R)-N-[1-(4-bromophenyl) ethyl]arginine amide hydrochloride Prepared according to the method described in Example 2(f) above from (R)-N²-(diphenylacetyl)-(R)-N-[1-(4-bromophenyl)ethyl]ornithine amide (free base, 0.42 g; 0.83 mmol; from step (d) above), 1H-pyrazole-1-carboxamidine mono hydrochloride (0.13 g; 0.83 mmol), triethylamine (0.17 g; 1.66 mmol; instead of DiPEA) and DMF (4 mL), 18 hours reaction time. The solution was concentrated under vacuum and the crude product chromatographed on silica gel using MeOH:$CHCl_3$:ammonium hydroxide (3:6:1). Conversion to the hydrochloride salt afforded the title compound as a white solid (0.31 g).

mp 115–120° C.

$R_f$ 0.4 (System D)

$[\alpha]_D^{23}$=+49.8° (c=1, MeOH)

¹H NMR ($CD_3OD$) δ1.40 (d, 3H), 1.75–1.88 (m, 4H), 3.02–3.17 (m, 2H), 4.39 (m, 1H), 4.88 (m, 1H), 5.14 (s, 1H), 7.18 (d, 2H), 7.13–7.50 (m, 10H), 7.43 (d, 2H)

Example 8

(R)-N²-(Diphenylacetyl)-(R,S)-N-[1-(3-methoxyphenyl)ethyl]arginine amide hydrochloride (a) (R)-N²-(Boc)-N⁵-(Cbz)-(R,S)-N-[1-(3-Methoxyphenyl)ethyl]ornithine amide DiPEA (5.4 mL; 31 mmol) was added to a stirred mixture of EDC x HCl (6.0 g; 31 mmol), N-α-Boc-N-δ-Cbz-(R)-ornithine (7.7 g; 21 mmol), (±)-3-methoxy-α-methylbenzylamine (3.2 g; 21 mmol) in $CH_2Cl_2$ (100 mL). The mixture was stirred for 18 hours at room temperature, then diluted with $CH_2Cl_2$ (100 mL) and washed 3 times with brine. The organic layer was separated and dried over sodium sulfate. After evaporation of the solvent, there was obtained a colourless oil which was loaded onto a column of wet silica gel (column: 50 mm diameter by 100 mm height) and eluted with 20% EtOAc in hexanes (500 mL), then 50% EtOAc in hexane (500 mL) and finally 100% EtOAc (500 mL). Fractions (75 mL each) 10–13 were combined and concentrated to afford 10.1 g of product as a colourless glass (90%).

(b) (R)-N⁵-(Cbz)-(R,S)-N-[1-(3-methoxyphenyl)ethyl]ornithine amide hydrochloride Prepared according to the method described in Example 1(b) above from (R)-N²-(Boc)-N⁵-(Cbz)-(R,S)-N-[1-(3-methoxyphenyl)ethyl]ornithine amide (10 g; 19.3 mmol; from step (a) above) which was deprotected using HCl/EtOAc (100 mL) yielding 7.7 g (100%) of sub-title compound.

(c) (R)-N⁵-(Cbz)-N²-(Diphenylacetyl)-(R,S)-N-[1-(3-methoxyphenyl)-ethyl]ornithine amide Prepared according to the method described in Example 4(d) above from (R)-N⁵-(Cbz)-(R,S)-N-[1-(3-methoxyphenyl)ethyl]ornithine amide hydrochloride (8.6 g; 19.3 mmol; from step (b) above) and diphenylacetylchloride (4.85 g; 21 mmol), which were combined in THF (75 mL) and stirred at −5° C. A 1M solution of $Na_2CO_3$ (21 mL; 42 equivalents) was added and stirred vigorously, then warmed to room temperature over 3 hours. The mixture was poured into water and extracted with EtOAc. The organic extract was washed with 5% citric acid solution followed by saturated $NaHCO_3$ solution, dried with $Na_2SO_4$ and concentrated to afford the sub-title compound (8.7 g; 73.7%).

(d) (R)-N²-(Diphenylacetyl)-(R,S)-N-[1-(3-methoxyphenyl)ethyl]ornithine amide hydrochloride Prepared according to the method described in Example 1(e) above from (R)-N⁵-(Cbz)-N²-(diphenyl acetyl)-(R,S)-N-[1-(3-methoxyphenyl)ethyl]-ornithine amide (2.3 g; 3.76 mmol; from step (c) above), which was deprotected in HOAc (instead of MeOH). The compound was then dissolved in HCl/MeOH and concentrated to dryness to afford the sub-title compound (1.8 g; 94%) as the HCl salt from acetonitrile and EtOAc.

mp 173–175° C.

¹H NMR ($CD_3OD$; mixture of diastereomers) δ6.7–7.4 (m, 14H), 5.1 (s, 1H), 4.9 (m, 1H), 4.45 (m, 1H), 3.72 (s, 3H), 2.9 (m, 2H), 1.5–1.9 (m, 4H), 1.38 (d, 3H)

(e) (R)-N^ω,N^ω'-bis(Cbz)-N²-(Diphenylacetyl)-(R,S)-N-[1-(3-methoxyphenyl) ethyl]arginine amide Prepared according to the method described in Example 4(f) above from (R)-N²-(diphenylacetyl)-(R,S)-N-[1-(3-methoxyphenyl)ethyl]ornithine amide hydrochloride (1.75 g; 3.4 mmol; from step (d) above), N,N'-bis(Cbz)-S-methylisothiourea (1.33 g; 3.7 mmol) in DMF (2.5 mL) and 1.5 equivalents of DiPEA. Reaction was over in 2 hours, based on TLC analysis. After chromatography, the sub-title product was used directly in the next step.

(f) (R)-N²-(Diphenylacetyl)-(R,S)-N-[1-(3-methoxyphenyl)ethyl]arginine amide hydrochloride Prepared according to the method described in Example 1(g) above from (R)-N^ω,N^ω'-bis(Cbz)-N²-(diphenylacetyl)-(R,S)-N-[1-(3-methoxyphenyl)-ethyl]arginine amide (1.7 g; 2.2 mmol; from step (e) above) in HOAc (100 mL) to afford 1.1 g of the title compound as the crude acetate salt. The salt was dissolved in MeOH and 1N HCl was added slowly to the cloud point. Crystals formed, which were collected and dried to afford 0.55 g (46%) of the title compound.

mp 103–108° C.

¹H NMR (300 MHz) ($CD_3OD$) (mixture of diastereomers) δ6.7–7.4 (m, 14H), 5.1 (s, 1H), 4.95 (m, 1H), 4.45 (m, 1H), 3.7 (s, 3H), 3.1 (m, 2H), 1.35–1.9 (m, 4H), 1.32 (d, 3H)

Example 9

(R)-N²-(Diphenylacetyl)-(R)-N-(1-phenylethyl)arginine amide hydrochloride (a) (R)-N²-(Boc)-N⁵-(Cbz)-(R)-N-(1-phenylethyl)ornithine amide Prepared according to the method described in Example 1(a) above from N^α-Boc-N^δ-Cbz-(R)-ornithine (5.0 g; 13 mmol), BOP reagent (6.0 g; 13 mmol), HOBT (1.8 g; 13 mmol) and DiPEA (7.1 mL; 40.0 mmol) 100 mL of acetonitrile:$CH_2Cl_2$ (1:1), followed by 1.8 mL (13 mmol) of (R)-α-methylbenzylamine, then stirred overnight. After work up, the crude product was purified by passing it through a plug of silica gel with EtOAc to give 5.9 g (92%) of the sub-title compound as a light yellow solid.

¹H NMR ($CD_3OD$) δ1.3–1.8 (m, 16H); 3.2 (m, 2H), 4.05 (m, 1H) 5.0–5.1 (m, 3H), 7.1–7.4 (m, 10H).

(b) (R)-N⁵-(Cbz)-N²-(Diphenylacetyl)-(R)-N-(1-phenylethyl)ornithine amide

Prepared according to the method described in Examples 2(b) and 2(c) above from (R)-N²-(Boc)-N⁵-(Cbz)-(R)-N-(1-phenylethyl)ornithine amide hydrochloride (5.9 g; 13 mmol; from step (a) above) EtOAc (30 mL) then HCl/EtOAc (100 mL), 3.5 hours reaction time for the deprotection, then $CH_2Cl_2$(100 mL), diphenylacetyl chloride (2.9 g; 13 mmol) followed by pyridine (3.0 mL; 37 mmol; instead of DiPEA) over 1 min, overnight reaction time, diluted with $CH_2Cl_2$ (100 mL) for the work up procedure. The organic layer was partially concentrated at reduced pressure, upon which a precipitate formed, which was filtered to give 1.7 g (24%) of the sub-title compound as a solid.

¹H NMR ($CD_3OD$) δ1.4 (m, 5H), 1.6 (m, 1H), 1.75 (m, 1H), 3.05 (m, 2H), 4.4 (m, 1H), 4.75 (m, 1H), 5.02 (s, 2H), 5.08 (s, 1H), 6.9 (m (exchangeable), 1H), 7.1–7.4 (m, 20H), 8.25 (m (exchangeable), 1H)

(c) (R)-N²-(Diphenylacetyl)-(R)-N-(1-phenylethyl)ornithine amide hydrochloride

Prepared according to the method described in Example 1(e) above from (R)-N⁵-(Cbz)-N²-(diphenylacetyl)-(R)-N-(1-phenylethyl)ornithine amide (1.7 g; 3.0 mmol; from step (b) above) 10% Pd/C (w/w; 100 mg), HOAc (75 mL), overnight reaction time. The crude acetate salt was converted to the sub-title compound and was used without further purification.

¹H NMR ($CD_3OD$) δ1.38 (d, 3H), 1.6 (m, 3H), 1.8 (m, 1H), 2.85 (m, 2H), 4.45 (m, 1H), 4.95 (m, 1H), 5.1 (s, 1H), 7.2 14 7.4 (m, 15H).

(d) (R)-N^ω,N^ω'-bis(Cbz)-N²-(Diphenylacetyl)-(R)-N-(1-phenylethyl)-arginine amide Prepared according to the method described in Example 4(f) above from (R)-N²-(diphenylacetyl)-(R)-N-(1-phenylethyl)ornithine amide (0.50 g; 1.0 mmol; from step (c) above), N,N'-bis(Cbz)-S-methylisothiourea (0.40 g; 1.1 mmol) and DiPEA (0.3 mL; 1.6 mmol) yielding 0.58 g (73%) of the sub-title compound as a solid.

(e) (R)-$N^2$-(Diphenylacetyl)-(R)-N-(1-phenylethyl)arginine amide hydrochloride Prepared according to the method described in Example 1(g) above from (R)-$N^\omega$,$N^{\omega'}$-bis(Cbz)-$N^2$-(diphenylacetyl)-(R)-N-(1-phenylethyl)arginine amide (0.6 g; 0.8 mmol; from step (d) above), 10% Pd/C (w/w; 200 mg), HOAc (25 mL), overnight reaction time. The crude acetate salt was converted to the hydrochloride to give 0.4 g (99%) of title compound as a solid.

mp 111–116° C.

$R_f$ 0.46 (System D)

$[\alpha]_D^{24}$=+51.0° (C=0.65, MeOH)

$^1$H NMR (CD$_3$OD) δ7.20–7.36 (m, 15H), 5.10 (s, 1H), 4.97 (q, 1H), 4.43 (t, 1H), 3.08 (m, 2H), 1.42–1.85 (m, 4H), 1.41 (d, 3H)

Example 10

(R)-$N^2$-(Diphenylacetyl)-(S)-N-(1-phenylethyl) arginine amide hydrochloride (a) (R)-$N^2$-(Boc)-$N^5$-(Cbz)-(S)-N-(1-Phenylethyl)ornithine amide Prepared according to the method described in Example 1(a) above from $N^\alpha$-Boc-$N^\delta$-Cbz-(R)-ornithine (5.0 g; 13 mmol), BOP reagent (6.0 g; 13 mmol), HOBT (1.8 g; 13 mmol) and DiPEA (7.1 mL; 40 mmol) 100 mL of acetonitrile:CH$_2$Cl$_2$ (1:1), followed by (S)-α-methylbenzylamine (1.8 mL; 13 mmol), then stirred overnight. After work up, the crude product was purified by passing it through a plug of silica gel with EtOAc to give 5.9 g (92%) of the sub-title as a light yellow solid.

$^1$H NMR (CD$_3$OD) δ1.2–1.8 (m, 16H), 3.2 (m, 2H), 4.05 (m, 1H), 4.9–5.1 (m, 3H), 7.1–7.4 (m, 10H)

(b) (R)-$N^5$-(Cbz)-$N^2$-(Diphenylacetyl)-(S)-N-(1-phenylethyl ornithine amide

Prepared according to the method described in Example 2(b) and 2(c) from (R)-$N^2$-(Boc)-$N^5$-(Cbz)-(S)-N-(1-phenylethyl)ornithine amide (5.9 g; 13 mmol; from step (a) above) EtOAc (30 mL) then HCl/EtOAc (100 mL), 3.0 hours reaction time for the deprotection, then CH$_2$Cl$_2$ (100 mL), diphenylacetyl chloride (3.0 g; 13 mmol) followed by pyridine (3.0 mnL; 37 mmol; instead of DiPEA) over 1 minute, overnight reaction time, diluted with CH$_2$Cl$_2$ (100 mL) for the work up procedure. Crystallization from CH$_2$C$_2$:EtOAc:MeOH gave 3.4 g (47%) of the sub-title compound as a solid.

$^1$H NMR (CD$_3$OD) δ1.35 (d, 3H), 1.45 (m, 2H), 1.65 (m, 1H), 1.8 (m, 1H), 3.2 (m, 2H), 4.45 (m, 1H), 4.85 (m, 1H), 5.02 (s, 1H), 5.08 (s, 2H), 7.1–7.4 (m, 20H)

(c) (R)-$N^2$-(Diphenylacetyl)-(S)-N-(1-phenylethyl)ornithine amide hydrochloride Prepared according to the method described in Example 1(e) above from (R)-$N^5$-(Cbz)-$N^2$-(diphenylacetyl)-(S)-N-(1-phenylethyl)ornithine amide (2.0 g; 3.5 mmol; from step (b) above), 10% Pd/C (w/w; 150 mg), HOAc (100 mL; instead of MeOH), overnight reaction time. The crude acetate salt was converted to the sub-title hydrochloride and was used without further purification.

$^1$H NMR (CD$_3$OD) δ1.4 (d, 3H), 1.65 (m, 3H), 1.85 (m, 1H), 2.9 (m, 2H), 4.45 (m, 1H), 4.95 (m, 1H), 5.05 (s, 1H), 7.15–7.4 (m, 15H)

(d) (R)-$N^\omega$,$N^{\omega'}$(bisCbz)-$N^2$-(Diphenylacetyl-(S)-N-(1-phenylethyl)arginine amide Prepared according to the method described in Example 4(f) above from (R)-$N^2$-(diphenylacetyl)-(S)-N-(1-phenylethyl)ornithine amide hydrochloride (0.50 g; 1.0 mmol; from step (c) above), N,N'-bis(Cbz)-S-methylisothiourea (0.40 g; 1.1 mmol) of and DiPEA (0.3 mL; 1.6 mmol), yielding 0.59 g (74%) of sub-title compound as a solid.

(e) (R)-$N^2$-(Diphenylacetyl)-(S)-N-(1-phenylethyl)arginine amide hydrochloride Prepared according to the method described in Example 1(g) above from (R)-$N^\omega$,$N^{\omega'}$-bis(Cbz)-$N^2$-(diphenylacetyl)-(S)-N-(1-phenylethyl)arginine amide (0.6 g; 0.8 mmol; from step (d) above), 10% Pd/C (w/w; 200 mg), HOAc (25 mL), overnight reaction time. The crude acetate salt was converted to the hydrochloride to give 0.4 g (99%) of the title compound as a solid.

mp 112–118° C.

$R_f$ =0.46 (System D)

$[\alpha]_D^{25}$=−2.6° (C=1.1, MeOH)

$^1$H NMR (CD$_3$OD) δ1.41 (d, 3H), 1.49–1.90 (m, 4H), 3.18 (m, 2H), 4.46 (t, 1H), 4.95 (q, 1H), 5.06 (s, 1H), 7.20–7.32 (m, 15H).

Example 11

(R)-$N^2$-(Diphenylacetyl)-(R,S)-N-[1-cyclopropyl-1-(4-methoxyphenyl)-methyl]arginine amide hydrochloride (a)(R)-$N^2$-(Boc)-$N^5$-(Cbz)-(R,S)-N-[1-Cyclopropyl-1-(4-methoxyphenyl)-methyl]ornithine amide Prepared analogously to the method described in Example 4(b) above from $N^\alpha$-Boc-$N^{67}$-Cbz-(R)-ornithine o-nitrophenyl ester (6.25 g; 12.8 mmol; see Example 4(a) above), (R,S)-α-cyclopropyl-4-methoxybenzenemethanamine hydrochloride (3.01 g; 14.1 mmol) and DiPEA (1.99 g, 15.4 mmol) in CH$_2$Cl$_2$ (200 mL), 3 hours reaction time, followed by additional DiPEA (1 mL) and (R,S)-α-cyclopropyl-4-methoxybenezenemethanamine hydrochloride (0.50 g) and stirred for 15 minutes. The reaction mixture was concentrated and dissolved in EtOAc. The EtOAc was washed with water, saturated aqueous potassium hydrogen sulfate, water, saturated aqueous sodium carbonate, brine, and then dried. Concentration of the organics afforded a yellow solid (7.40 g) as a mixture of diastereomers. The crude material was used without further purification. An analytical sample was prepared by crystallization from the EtOAc:diethyl ether:hexanes.

mp 122–125° C.

$R_f$ 0.50 (hexanes:EtOAc (3:7); silica gel TLC plate)

(b) (R)-$N^5$-(Cbz)-(R,S)-N-[1-Cyclopropyl-1-(4-methoxyphenyl)methyl]-ornithine amide hydrochloride Prepared according to the method described in Example 1(b) above from crude (R)-$N^2$-(Boc)-$N^5$-(Cbz)-(R,S)-N-[1-cyclopropyl-1-(4-methoxy-phenyl)methyl]ornithine amide (5.6 g; from step (a) above), EtOAc (100 mL) and HCl/EtOAc (100 mL), 18 hours reaction time. The hydrochloride salt was precipitated by the addition of diethyl ether, collected and dried to give the sub-title compound as a greyish solid (3.8 g).

$R_f$ 0.3 (CHCl$_3$:MeOH:HOAc (9.0:1.0:0.1); silica gel TLC plate) $^1$H NMR (CD$_3$OD; complex mixture of diastereomers) δ0.28–0.42 (m), 0.52–0.65 (m), 0.88–0.98 (m), 1.15–1.98 (m), 3.02–3.20 (m), 3.72 (s), 3.74 (s), 3.75–3.95 (m), 4.20–4.30 (m), 5.02–5.13 (m), 6.83–6.90 (m), 7.18–7.40 (m)

(c) (R)-$N^5$-(Cbz)-$N^2$-(Diphenylacetyl)-(R,S)-N-[1-cyclopropyl-1-(4-methoxyphenyl)methyl]ornithine amide Prepared according to the method described in Example 1(d) above from (R)-$N^5$-(Cbz)-(R,S)-N-[1-cyclopropyl-1-(4-methoxyphenyl)methyl]ornithine amide hydrochloride (2.0 g; 4.3 mmol; from step (b) above), 2-nitrophenyl diphenyl acetate (1.4 g; 4.3 mmol; see Example 1(c) above), triethylamine (0.7 g; 6.5 mmol) and $CH_2Cl_2$ (150 mL), 18 hours reaction time at room temperature, and 4 hours reaction time at reflux. The reaction mixture was submitted to aqueous work up, dried, filtered and concentrated to give the crude product as a yellow solid (2.8 g). The product was chromatographed on silica gel eluting with hexanes:EtOAc (1:1) then $CH_2Cl_2$:EtOAc (1:1). Concentration of the product containing fractions gave pure sub-title compound as a light yellow solid (2.2 g).

$R_f$ 0.4 (hexanes:EtOAc (1:1), silica gel TLC plate)

$^1H$ NMR ($CD_3OD$, complex mixture of diastereomers) δ0.25–0.36 (m), 0.45–0.60 (m), 0.80–0.98 (m), 1.00–1.92 (m), 2.95–3.16 (m), 3.73 (s), 3.74 (s), 4.16–4.28 (m), 4.38–4.50 (m), 4.70–4.85 (m), 4.98–5.08 (m), 6.72–6.87 (m), 7.05–7.40 (m).

(d) (R)-$N^2$-(Diphenylacetyl)-(R,S)-N-[1-cyclopropyl-1-(4-methoxy-phenyl)methyl]ornithine amide hydrochloride Prepared according to the method described in Example 1(e) above from (R)-$N^5$-(Cbz)-$N^2$-(diphenylacetyl)-(R,S)-N-[1-cyclopropyl-1-(4-methoxy-phenyl)methyl]ornithine amide (2.0 g; 3.23 mmol; from step (c) above), 10% Pd/C (1.0 g), MeOH (250 mL) and concentrated HCl (5 mL) under hydrogen, 60 hours reaction time, to give the crude product. The free base was prepared to afford a solid (1.1 g) which was chromatographed on silica gel eluting with MeOH:ammonium hydroxide (15:1). Concentration of the product containing fractions gave pure sub-title compound as an off-white solid (0.6 g; $R_f$ 0.4 (MeOH:ammonium hydroxide (30:1), silica gel TLC plate), which was treated with HCl/MeOH to give the sub-title hydrochloride salt as a white solid.

mp 190–197° C.

$^1H$ NMR ($CD_3OD$, mixture of diastereomers) δ0.81–0.97 (m, 2H), 1.10–1.40 (m, 2H), 1.52–1.93 (m, 5H), 2.78–2.94 (m, 2H), 3.78 (s, 3H), 4.45 (m, 1H), 4.77 (m, 1H), 5.08 (s, 1H), 5.12 (s, 1H), 6.75–6.87 (m, 2H), 7.08–7.40 (m, 14H)

(e) (R)-$N^ω$,$N^{ω'}$-bis(Cbz)-$N^2$-(Diphenylacetyl)-(R,S)-N-[1-cyclopropyl-1-(4-methoxyphenyl) methyl]arginine amide Prepared according to the method described in Example 4(f) above from (R)-$N^2$-(diphenylacetyl)-(R,S)-N-[1-cyclopropyl-1-(4-methoxyphenyl)-methyl]ornithine amide hydrochloride (0.46 g; 0.88 mmol; from step (d) above), N,N'-bis(Cbz)-S-methylisothiourea (0.35 g; 0.97 mmol), triethylamine (0.27 g; 2.64 mmol; instead of DiPEA) and THF (30 mL; instead of DMF), 18 hours reaction time. Concentration under vacuum gave the crude product which was chromatographed on silica gel eluting with hexanes:EtOAc (1:1) to give pure sub-title compound (0.24 g).

$R_f$ 0.3 (hexanes:EtOAc (1:1); silica gel TLC plate)

$^1H$ NMR ($CD_3OD$, complex mixture of diastereomers) δ0.77–0.90 (m), 1.08–1.94 (m), 3.12–3.42 (m), 3.77 (s), 3.78 (s), 4.38–4.55 (m), 4.73–4.87 (m), 4.88–5.22 (m), 6.62–6.87 (m), 6.90–7.48 (m), 8.22–8.40 (m).

(f) (R)-$N^2$-(Diphenylacetyl)-(R,S)-N-[1-cyclopropyl-1-(4-methoxy-phenyl)methyl]arginine amide hydrochloride Prepared according to the method described in Example 1(g) above from (R)-$N^ω$,$N^{ω'}$-bis(Cbz)-$N^2$-(diphenylacetyl)-(R,S)-N-[1-cyclopropyl-1-(4-methoxyphenyl)methyl] arginine amide (0.24 g; 0.30 mmol; from step (e) above), 10% Pd/C (0.12 g) and, instead of HOAc, MeOH (75 mL) and concentrated HCl (1 mL) under hydrogen, 15 hours reaction time, gave the crude product which was chromatographed on silica gel eluting with MeOH:$CHCl_3$:ammonium hydroxide (3:6:1) to give the title compound as a solid (0.16 g).

mp 105–115° C.

$R_f$ 0.3 (System D)

$^1H$ NMR ($CD_3OD$, mixture of diastereomers) δ0.80–0.93 (m), 1.07–1.92 (m), 3.03–3.20 (m), 3.78 (s), 4.35–4.47 (m), 4.62–4.95 (m), 5.13 (s), 5.16 (s), 6.25–6.88 (m), 7.08–7.45 (m), 8.10–8.26 (m)

$^{13}C$ NMR ($CD_3OD$) δ14.5, 21.0, 27.0, 30.5, 40.0, 42.2, 54.5, 55.2, 56.2, 59.0, 115.0, 128.4, 129.0, 129.8, 130.2, 136.2, 141.0, 158.8, 160.4, 173.2, 175.2.

Example 12

(R)-$N^2$-(Diphenylacetyl)-N-(1-methyl-1-phenylethyl)arginine amide hydrochloride (a) (R)-$N^2$-(Boc)-$N^5$-(Cbz)-N-(1-methyl-1-phenylethyl) ornithine amide Prepared according to the method described in Example 4(b) above from $N^α$-Boc-$N^δ$-Cbz-(R)-ornithine o-nitrophenyl ester (5.0 g; 11.5 mmol; see Example 4(a) above) and cumylamine (1.55 g; 11.5 mmol) and 160 mL of $CH_2Cl_2$. The reaction mixture was heated to reflux for 2 hours. The mixture was concentrated to dryness and dissolved in EtOAc and washed with saturated aqueous $KHSO_4$ and brine, dried with $Na_2SO_4$, filtered and concentrated to give 6.1 g of the sub-title compound as a yellow oil.

$R_f$ 0.93 (System B)

(b)(R)-$N^5$-(Cbz)-N-(1-methyl-1-phenylethyl)ornithine amide hydrochloride

Prepared according to the method described in Example 1(b) above from (R)-$N^2$-(Boc)-$N^5$-(Cbz)-N-(1-methyl-1-phenylethyl)ornithine amide (6.0 g; from step (a) above) treated with EtOAc (100 mL) and HCl/EtOAc (50 mL), 24 hours reaction time. The reaction mixture was concentrated to dryness and triturated with ether to give 3.68 g of the sub-title compound as a white solid.

$^1H$ NMR ($CD_3OD$) δ1.95–1.5 (m, 4H), 1.64 (s, 3H), 1.66 (s, 3H), 3.14 (t, 2H) 3.89 (m, 1H), 5.06 (s, 2H), 7.45–7.1 (m, 10H).

(c) (R)-$N^5$-(Cbz)-$N^2$-(Diphenylacetyl)-N-(1-methyl-1-phenylethyl)-ornithine amide Prepared according to the method described in Example 1(d) above from (R)-$N^5$-(Cbz)-N-(1-methyl-1-phenylethyl) ornithine amide hydrochloride (3.6 g; 8.57 mmol; from step (b) above), 2-nitrophenyl diphenyl acetate (3.44 g; 10.8 mmol; see Example 1(c) above), and triethylamine (1.5 mL; 10.8 mmol) in 100 mL of $CH_2Cl_2$. The reaction mixture was stirred for 12 hours and submitted to aqueous work up. The product was chromatographed eluting with EtOAc/hexanes on 250 mL of silica gel, yielding 4.26 g of sub-title compound.

(d) (R)-$N^2$-(Diphenylacetyl)-N-(1-methyl-1-phenylethyl) ornithine amide hydrochloride Prepared according to the method described in Example 1(e) above from (R)-$N^5$-(Cbz)-$N^2$-(diphenylacetyl)-N-(1-methyl-1-phenylethyl)ornithine amide (4.21 g; from step (c) above) using 10% Pd/C (200 mg) in 150 mL of MeOH and 1 mL of concentrated HCl, yielding 3.88 g of sub-title compound.

mp 126–128° C.

MS(Cl/Isobutane) 444 m/z $R_f$ 0.53 (EtOAc:MeOH:$NH_4OH$ (47:47:6))

1H NMR ($CD_3OD$) δ1.48 (s, 3H), 1.58 (s, 3H), 1.78 (m, 2H), 1.55 (m, 2H), 2.61 (t, 2H), 4.41 (m, 1H), 5.05 (s, 1H), 7.4–7.05 (m, 15H)

(e) (R)-$N^2$-(Diphenylacetyl)-($N^ω$,$N^{ω'}$)-bis(Cbz)-N-(1-methyl-1-phenyl-ethyl)arginine amide Prepared according to the method described in Example 4(f) above from (R)-$N^2$-(diphenylacetyl)-N-(1-methyl-1- phenylethyl)ornithine amide hydrochloride (2.0 g; 4.2 mmol; from step (d) above), N,N'-bis(Cbz)-S-methylisothiourea (2.4 g; 6.2 mmol), 1 mL of DiPEA and 50 mL of DMF, yielding 1.1 g of the sub-title compound as a white solid.

(f) (R)-$N^2$-(Diphenylacetyl)-N-(1-methyl-1-phenylethyl) arginine amide hydrochloride Prepared according to the method described in Example 1(g) above from (R)-$N^2$-(diphenylacetyl)-($N^{\omega}$,$N^{\omega'}$)-bis (Cbz)-N-(1-methyl-1-phenylethyl)-arginine amide (0.5 g; from step (e) above), 10% Pd/C (0.1 g) and, instead of HOAc, concentrated HCl (0.4 mL) and MeOH (50 mL), yielding 62 mg of the title compound.

mp 140–143° C.

$R_f$ 0.43 (EtOAc:MeOH:conc. ammonium hydroxide (46:46:7))

$^1$H NMR (CD$_3$OD) δ1.55 (s, 3H), 1.59 (s, 3H), 1.90–1.40 (m, 4H), 3.16 (m, 2H), 4.44 (m 1H), 4.81 (m, 1H), 5.08 (s, 1H), 7.4–7.0 (m, 15H) 8.0 (s, 1H, NH), 8.38 (d, 1H, NH)

Example 13

(R)-$N^2$-(Diphenylacetyl)-(R,S)-N-(1-indanyl) arginine amide hydrochloride (a) (R)-$N^2$-(Boc)-$N^5$-(Cbz)-(R,S)-N-(1-indanyl)ornithine amide Prepared according to the method described in Example 1(a) above from $N^{\alpha}$-Boc-$N^{\delta}$-Cbz-(R)-ornithine (3.7 g; 10 mmol), BOP reagent (4.4 g; 10 mmol), HOBT (2.7 g; 20 mmol) and DiPEA (5.0 mL; 30.0 mmol) in acetonitrile (200 mL; instead of acetonitrile:CH$_2$Cl$_2$ (1:1)), followed by (R,S)-1-indanamine (1.3 mL; 10 mmol). Work up gave 4.0 g (83%) of the sub-title compound as a solid.

$^1$H NMR (CDCl$_3$) δ1.30–1.90 (m, 7H), 1.40 (s, 9H), 2.45–2.62 (m, 1H), 2.75–3.05 (m, 2H), 3.05–3.22 +3.25–3.50 (m, 2H), 4.15–4.32 (m, 1H), 4.82–5.00 (m, 2H), 5.18–5.33 (m, 1H), 5.35–5.55 (m, 1H), 6.60–6.70 (m, 1H), 7.05–7.40 (m, 9H)

(b) (R)-$N^5$-(Cbz)-$N^2$-(Diphenylacetyl)-(R,S)-N-(1-indanyl) ornithine amide

Prepared according to the method described in Example 2(b) and 2(c) above from (R)-$N^2$-(Boc)-$N^5$-(Cbz)-(R,S)-N-(1-indanyl)ornithine amide (1.6 g; 3.2 mmol; from step (a) above) EtOAc (10 mL) then HCl/EtOAc (125 mL), 1 hour reaction time for the deprotection, then CH$_2$Cl$_2$ (125 mL), diphenylacetyl chloride (0.74 g; 3.6 mmol), followed by DiPEA (1.7 mL; 9.7 mmol) over 1 minute, 1 hour reaction time, diluted with CH$_2$Cl$_2$ (125 mL) for the work up procedure, yielding 1.8 g (100%) of the sub-title compound.

$^1$H NMR (CDCl$_3$) δ1.40–1.90 (m, 7H), 2.40–2.55 (m, 1H), 2.72–2.96 (m, 2H), 3.00–3.18 +3.25–3.53 (m, 2H), 4.55–4.72 (m, 1H), 4.75–4.96 (m, 2H), 5.25–5.95 (m, 1H), 6.55–6.65 +6.78–6.95 (m, 1H), 7.05–7.40 (m, 19H).

(c) (R)-$N^2$-(Diphenylacetyl)-(R,S)-N-(1-indanyl)ornithine amide

Prepared according to the method described in Example 1(e) above from (R)-$N^5$-(Cbz)-$N^2$-(diphenylacetyl)-(R,S)-N-(1-indanyl)ornithine amide (1.2 g; 2.2 mmol; from step (b) above), 10% Pd/C (w/w; 500 mg), MeOH (100 mL; HCl was not added), and 2.5 hours reaction time, yielding 0.82 g (90%) of the sub-title compound as a pale white solid.

$R_f$ 0.54 (System A)

$^1$H NMR (CDCl$_3$) δ1.35–1.90 (m, 7H), 2.40–2.95 (m, 5H), 4.40–4.55 (m, 1H), 4.90 (s, 1H), 5.30–5.45 (m, 1H), 6.95–7.40 (m, 14H).

(d) (R)-$N^2$-(Diphenylacetyl)-(R,S)-N-(1-indanyl)ornithine amide hydrochloride

A sample of (R)-$N^2$-(diphenylacetyl)-(R,S)-N-(1-indanyl) ornithine amide (from step (c) above) was treated with HCl/EtOAc then evaporated at reduced pressure. Crystallization from MeOH:diethyl ether gave the sub-title hydrochloride.

mp 220–225° C. (dec.)

$^1$H NMR (CD$_3$OD) δ1.60–2.00 (m, 7H), 2.30–2.50 (m, 1H), 2.72–3.00 (m, 4H), 4.35–4.98 (m, 1H), 5.12 (s, 1H), 5.25–5.35 (m, 1H), 7.05–7.40 (m, 14H), 7.95–8.12 (m 1H), 8.45–8.55 (m, 1H).

(e) (R)-$N^2$-(Diphenylacetyl)-(R,S)-N-(1-indanyl)arginine amide hydrochloride

Prepared according to the method described in Example 2(f) above from (R)-$N^2$-(diphenylacetyl)-(R,S)-N-(1-indanyl)ornithine amide (0.54 g; 1.3 mmol; free base from step (c) above), 1H-pyrazole-1-carboxamidine mono hydrochloride (0.20 g; 1.3 mmol), and DiPEA (0.8 mL; 5 mmol). The product was additionally rinsed with EtOAc to give 0.19 g (28%) of the title compound as a white solid.

mp 130–140° C.

$R_f$ =0.16 (System A)

$^1$H NMR (CD$_3$OD) δ1.50–1.95 (m, 7H), 2.35–2.52 (m, 1H), 2.75–3.00 (m, 2H), 3.08–3.20 (m, 2H), 4.35–4.45 (m, 1H), 5.10 (s, 1H), 5.28–5.38 (m, 1H), 7.05–7.40 (m, 14H).

Example 14

(R)-$N^2$-(Diphenylacetyl)-(S or R)-N-(1-carbamoylphenylmethyl)arginine amide hydrochloride (a) (R)-$N^2$-(Boc)-$N^5$-(Cbz -(R or S)-N-(1-carbamoylphenylmethyl)ornithine amide and (R)-$N^2$-(Boc)-$N^5$-(Cbz)-(S or R)-N-(1-carbamoylphenylmethyl)-ornithine amide Prepared according to the method described in Example 1(a) above from $N^{\alpha}$-Boc-$N^{\delta}$-Cbz-(R)-ornithine (8.0 g; 22 mmol), BOP (9.7 g; 22 mmol), HOBT (3.0 g; 22 mmol) and DiPEA (11.3 mL; 65.0 mmol) in 160 mL of acetonitrile:CH$_2$Cl$_2$ (1:1), followed by racemic α-aminophenylacetamide (3.3 g; 22 mmol), then stirred overnight. After work up the crude product was purified by passing it through a plug of silica gel with EtOAc to give 8.0 g (73%) of a diastereomeric mixture of the sub-title compounds as a solid.

b) (R)-$N^5$-(Cbz)-$N^2$-(Diphenylacetyl)-(R or S)-N-(1-carbamoylphenyl-ethyl)ornithine amide and (R)-$N^5$-(Cbz)-$N^2$-(Diphenylacetyl)-(S or R)-N-1-carbamoylphenylmethyl)ornithine amide Prepared according to the method described in Example 2(b) and 2(c) above from a mixture of (R)-$N^2$-(Boc)-$N^5$-(Cbz)-(R or S)-N-(1-carbamoyl-phenylmethyl)ornithine amide and (R)-$N^2$-(Boc)-$N^5$-(Cbz)-(S or R)-N-(1-carbamoylphenylmethyl)ornithine amide (8.0 g; 16 mmol; from step (a) above), EtOAc (250 mL) then HCl/EtOAc (60 mL), 2 hours reaction time for the deprotection, then CH$_2$Cl$_2$ (100 mL), diphenylacetyl chloride (3.7 g; 16 mmol) followed by pyridine (12 mL; 0.15 mol; instead of DiPEA) over 10 minutes, overnight reaction time, diluted with CH$_2$Cl$_2$(100 mL) and some EtOAc to help with solubility for the work up procedure. The crude product was purified by dissolving the product in a mixture of MeOH:HOAc and filtering off the solids. Concentration of the filtrate at reduced pressure provided 6.0 g (63%) of a mixture of sub-title compounds as a solid.

$^1$H NMR (CD$_3$OD) δ1.45 (m, 2H), 1.65 (m, 1H), 1.75 (m, 1H), 3.05 (m, 2H), 4.4 (m, 1H), 4.9–5.1 (m, 4H), 7.2–7.5 (m, 20H)

(c) (R)-N²-(Diphenylacetyl)-(R or S)-N-(1-carbamoylphenylmethyl)-ornithine amide acetate Prepared according to the method described in Example 1(e) above from a mixture of (R)-N⁵-(Cbz)-N²-(diphenylacetyl)-(R or S)-N-(1-carbamoyl phenylmethyl) ornithine amide and (R)-N⁵-(Cbz)-N²-(diphenylacetyl)-(S or R)-N-(1-carbamoylphenylmethyl)ornithine amide (6.0 g; 10 mmol; from step (b) above) 10% Pd/C (w/w; 600 mg), HOAc (200 mL; instead of MeOH), overnight reaction time. The crude product mixture was crystallized from HOAc:EtOAc to give the sub-title compound (0.5 g; 94%).

(d) (R)-N²-(Diphenylacetyl)-(S or R)-N-(1-carbamoyl-phenylmethyl)-ornithine amide The mother liquors from step (c) above were allowed to sit overnight, after which a second crop of crystals were obtained which was the sub-title compound (0.42 g; 8%).

(e) (R)-N^ω, N^ω'-bis(Cbz)-N²-(Diphenylacetyl)-(S or R)-N-(1-carbamoyl-phenylmethyl)arginine amide Prepared according to the method described in Example 4(f) above, with the exception that THF (5 mL) was added as a co-solvent, from (R)-N²-(diphenylacetyl)-(S or R)-N-(1-carbamoyl-phenylmethyl)ornithine amide (0.4 g; 0.8 mmol; from step (d) above), N,N'-bis(Cbz)-S-methylisothiourea (0.3 g; 0.8 mmol) and DiPEA (0.2 mL; 1.1 mmol). The crude product was purified by crystallization from EtOAc, which gave 0.40 g (64%) of the sub-title compound as a solid.

(f) (R)-N²-(Diphenylacetyl)-(S or R)-N-(1-carbamoylphenylmethyl)arginine amide hydrochloride Prepared according to the method described in Example 1(g) above from (R)-N^ω,N^ω'-bis(Cbz)-N²-(diphenylacetyl)-(S or R)-N-(1-carbamoylphenyl-methyl)-arginine amide (0.25 g; 0.33 mmol; from step (e) above), 10% Pd/C (w/w; 100 mg), HCl/MeOH (50 mL), and overnight reaction time. The crude product was purified by column chromatography using CHCl₃:MeOH:concentrated ammonium hydroxide (6:3:1) to provide 0.16 g (91%) of the title compound.

mp 110–150° C.

$R_f$ =0.58 (System D)

Example 15

(R)-N²-(Diphenylacetyl)-(R or S)-N-[1-carbamoyl-(4-methoxyphenyl)-methyl]arginine amide hydrochloride (a) (R)-N²-(Boc)-N⁵-(Cbz)-(R or S)-N-[1-carbamoyl-(4-methoxyphenyl)-methyl]ornithine amide and (R)-N²-(Boc)-N⁵-(Cbz -(S or R)-N-[1-carbamoyl(4-methoxy-phenyl)methyl]ornithine amide Prepared according to the method described in Example 1(a) above from N^α-Boc-N^δ-Cbz-(R)-ornithine (5.0 g; 13 mmol), BOP reagent (6.0 g; 13 mmol), HOBT (1.8 g; 13 mmol) and DiPEA (7.1 mL; 40 mmol) in 100 mL of acetonitrile:CH₂Cl₂ (1:1), followed by a racemic mixture of 4-methoxy-α-aminophenylacetamide (2.5 g; 13 mmol), stirring overnight. After work up, the crude product was purified by crystallization from EtOAc:MeOH, yielding 4.5 g (62%) of a diastereomeric mixture of the sub-title compounds as a solid.

¹H NMR (CD₃OD) δ1.43 (s, 9H), 1.49–1.85 (m, 4H), 3.12 (m, 2H), 3.76 and 3.79 (2s, 3H), 4.08 (m, 1H), 5.02 (s, 1H), 5.08 (s, 1H), 5.33 (m, 1H), 6.89 (d, 2H), 7.32 (m, 7H).

(b) (R)-N⁵-(Cbz)-(R or S)-N-[1-carbamoyl-(4-methoxyphenyl)methyl]ornithine amide hydrochloride A mixture of(R)-N²-(Boc)-N⁵-(Cbz)-(R or S)-N-[1-carbamoyl-(4-methoxy-phenyl)methyl]ornithine amide and (R)-N²-(Boc)-N⁵-(Cbz)-(S or R)-N-[1-carbamoyl(4-methoxyphenyl)methyl]ornithine amide (4.5 g; 8.5 mmol) was dissolved in 25 mL of MeOH and 100 mL of HCl/EtOAc was added. The mixture was magnetically stirred at room temperature for 1 hour, then evaporated at reduced pressure to give a crude hydrochloride salt of the diastereomers of (R)-N⁵-(Cbz)-(R or S)-N-[1-carbamoyl-(4-methoxy-phenyl)methyl]ornithine amide and (R)-N⁵-(Cbz)-(S or R)-N-[1 -carbamoyl-(4-methoxyphenyl)methyl]ornithine amide hydrochloride. Crystallization from MeOH:EtOAc provided 1.3 g of the more polar sub-title diastereomer (32%).

$R_f$ 0.36 (System C)

¹H NMR (CD₃OD) δ1.5 (m, 2H), 1.8 (m, 2H), 3.1 (m, 2H) 3.7 (s, 3H), 3.95 (m, 1H), 4.95 (d, 2H), 5.38 (s, 1H), 6.9 (d, 2H), 7.3 (m, 2H)

(c) (R)-N⁵-(Cbz)-N²-(Diphenylacetyl)-(R or S)-N-[1-carbamoyl-(4-methoxyphenyl)methyl]ornithine amide To a mixture of (R)-N⁵-(Cbz)-(R or S)-N-[1-carbamoyl-(4-methoxyphenyl)-methyl]ornithine amide hydrochloride (1.2 g; 2.6 mmol; from step (b) above) and pyridine (4 mL; 49 mmol) in CH₂Cl₂ (80 mL) and DMF (2.5 mL) was added diphenylacetyl chloride (0.59 g; 2.6 mmol) and the resultant mixture was stirred overnight. The solvents were evaporated under reduced pressure and the residue was partitioned between MeOH:EtOAc (1:2) and dilute KHSO₄ solution. The organic layer was separated and concentrated under reduced pressure and the resulting solid was washed with water to remove inorganic salts. This provided 0.95 g (59%) of sub-title compound as a white solid.

¹H NMR (CD₃OD) δ1.45 (m, 2H), 1.65 (m, 1H), 1.75 (m, 1H), 3.08 (m, 2H), 3.75 (s, 3H), 4.4 (m, 1H), 5.0–5.1 (s, s ,m, 4H), 5.28 (s, 1H), 6.85 (d, 2H), 7.15–7.4 (17H)

(d) (R)-N²-(Diphenylacetyl)-(R or S)-N-[1-carbamoyl-(4-methoxyphenyl)-methyl]ornithine amide acetate Prepared according to the method described in Example 1(e) above from (R)-N⁵-(Cbz)-N²-(diphenylacetyl)-(R or S)-N-[1-carbamoyl-(4-methoxy-phenyl)methyl]ornithine amide (0.95 g; 1.4 mmol; from step (c) above) 10% Pd/C (w/w; 120 mg), HOAc (100 mL; instead of MeOH), overnight reaction time. The crude acetate salt was crystallized from MeOH:EtOAc to give 0.84 g (99%) of the sub-title compound as a solid.

e) (R)-N^ω,N^ω'-bis(Cbz)-N²-(Diphenylacetyl)-(R or S)-N-[1-carbamoyl-(4-ethoxyphenyl)methyl]arginine amide Prepared according to the method described in Example 4(f) above from (R)-N²-(diphenylacetyl)-(R or S)-N-[1-carbamoyl-(4-methoxyphenyl)-methyl]ornithine amide acetate (0.49 g; 1.0 mmol; from step (d) above), N,N'-bis(Cbz)-S-methylisothiourea (0.35 g; 0.99 mmol) and DiPEA (0.25 mL; 1.4 mmol). The product was purified by crystallization from EtOAc:MeOH, which gave 0.43 g (70%) of the sub-title compound as a solid.

(f) (R)-N²-(Diphenylacetyl)-(R or S)-N-[1-carbamoyl-(4-methoxyphenyl)-methyl]-arginine amide hydrochloride Prepared according to the method described in Example 1(g) above from (R)-N^ω,N^ω'-bis(Cbz)-N²-(diphenylacetyl)-(R or S)-N-[1-carbamoyl-(4-methoxyphenyl)methyl]arginine amide (0.42 g; 0.53 mmol; from step (e) above) 10% Pd/C (w/w; 100 mg), HOAc (75 mL) and overnight reaction time. The crude acetate salt was converted to the hydrochloride then triturated with MeOH:EtOAc to provide 0.15 g (52%) of the title compound.

mp 140–158° C.

$R_f$ =0.56 (System E)

¹H NMR (CD₃OD) δ1.42–1.91 (m, 4H), 3.12 (t, 2H), 3.79 (s, 3H), 4.41 (t, 1H), 5.08 (s, 1H), 5.31 (s, 1H), 6.82 (d, 2H), 7.18–7.35 (m, 12H)

Example 16

(R)-N²-(Diphenylacetyl)-(S)-N-(2-hydroxy-1-phenylethyl)arginine amide hydrochloride (a) (R)-N²-(Boc)-N⁵-(Cbz)-(S)-N-(2-hydroxy-1-phenylethyl)ornithine amide Prepared according to the method described in Example 4(b) above from N$^\alpha$-Boc-N$^\delta$-Cbz-(R)-ornithine o-nitrophenyl ester (4.0 g; 9.22 mmol; see Example 4(a) above) and (S)-(+)-phenylglycinol (1.26 g; 9.22 mmol; 1 eq.) and $CH_2Cl_2$ (160 mL). The reaction mixture was stirred overnight and then washed with saturated aqueous $KHSO_4$, saturated aqueous $Na_2CO_3$, brine, dried with $Na_2SO_4$, filtered and concentrated to dryness. The residue was triturated with ether to obtain 3.8 g of the sub-title compound as a white solid.

$R_f$ 0.48 ($CH_2Cl_2$:MeOH (80:20); silica gel TLC plate)

¹H NMR (DMSO-$d_6$) δ1.36(s, 9H), 1.80–1.37 (m, 4H), 2.95 (q, 2H), 3.55 (m, 2H), 3.95 (m, 1H), 4.81 (m, 2H), 5.0 (s, 2H), 6.79 (d, 1H), 7.41–721 (m, 10 H), 8.11 (d, 1H, NH)

(b) (R)-N⁵-(Cbz)-(S)-N-(2-hydroxy-1-phenylethyl)ornithine amide hydrochloride

Prepared according to the method described in Example 1(b) above from (R)-N²-(Boc)-N⁵-(Cbz)-(S)-N-(2-hydroxy-1-phenylethyl)ornithine amide (3.2 g; 6.6 mmol; from step (a) above), 25 mL of MeOH and 100 mL of HCl/EtOAc, yielding 2.0 g of the sub-title compound as white crystals.

(c) (R)-N⁵-(Cbz)-N²-(Diphenylacetyl)-(S)-N-(2-hydroxy-1-phenylethyl)-ornithine amide Prepared according to the method described in Example 1(d) above from (R)-N⁵-(Cbz)-(S)-N-(2-hydroxy-1-phenylethyl)ornithine amide hydrochloride (2.0 g, 4.74 mmol; from step (b) above), 2-nitrophenyl diphenyl acetate (1.67 g; 5.21 mmol; see Example 1(c) above) and triethylamine (0.726 mL; 5.21 mmol) in 150 mL of $CH_2Cl_2$. The reaction mixture was heated to reflux for 1 hour, followed by standard aqueous work up, yielding 1.78 g of the sub-title compound as a white solid.

¹H NMR (DMSO-$d_6$) δ1.71–1.2 (m, 4H), 2.91 (m, 2H), 3.52 (m, 2H), 4.42 (m, 1H), 4.82 (m, 2H), 5.0 (s, 2H), 5.15 (s, 1H), 7.5–7.1 (m, 15H), 8.35 (m, 2H, NH).

(d) (R)-N²-(Diphenylacetyl)-(S)-N-(2-hydroxy-1-phenylethyl)ornithine amide

Prepared according to the method described in Example 1(e) above from a batch of (R)-N⁵-(Cbz)-N²-(diphenylacetyl)-(S)-N-(2-hydroxy-1-phenyl-ethyl)ornithine amide (1.78 g; from step (c) above) and 10% Pd/C (200 mg) in 100 mL of MeOH and 1.0 mL of HCl (conc.), yielding 1.15 g of the sub-title compound as a white foam.

$R_f$ 0.44 (EtOAc:hexanes (4:1))

¹H NMR (DMSO-$d_6$) δ1.52 (m, 3H), 1.62 (m, 1H), 2.70 (m, 2H), 3.50 (m, 2H), 4.43 (m, 1H), 5.19 (s, 1H), 7.25 (m, 15H), 8.51 (d, 1H, NH), 8.61 (d, 1H, NH).

(e) (R)-N$^\omega$,N$^{\omega'}$-bis(Cbz)-N²-(Diphenylacetyl)-(S)-N-(2-hydroxy-1-phenyl-ethyl)arginine amide Prepared according to the method described in Example 4(f) above from (R)-N²-(diphenylacetyl)-(S)-N-(2-hydroxy-1-phenylethyl)ornithine amide (0.5 g; 1.12 mmol; from step (d) above), N,N'-bis(Cbz)-S-methyl-isothiourea (0.603 g; 1.68 mmol), DiPEA (0.2 mL) and DMF (15 mL), yielding 0.386 g of the sub-title compound.

(f) (R)-N²-(Diphenylacetyl)-(S)-N-(2-hydroxy-1-phenylethyl)arginine amide hydrochloride Prepared according to the method described in Example 1(g) above from (R)-N$^\omega$,N$^{\omega'}$-bis(Cbz)-N²-(diphenylacetyl)-(S)-N-(2-hydroxy-1-phenylethyl)-arginine amide (0.250 g; from step (e) above), 10% Pd/C (200 mg) and, instead of HOAc, 50 mL of MeOH with 1 mL of concentrated HCl, yielding 78 mg of the title compound.

¹H NMR (CD₃OD) δ1.57 (m, 2H), 1.71 (m, 1H), 1.86 (m, 1H), 3.14 (t, 2H), 3.70 (m, 2H), 4.53 (m, 1H), 5.08 (s, 1H), 7.35 (m, 15H)

Example 17

(R)-N²-(Diphenylacetyl)-(R)-N-(2-hydroxy-1-phenylethyl)arginine amide hydrochloride (a) (R)-N²-(Boc)-N⁵-(Cbz)-(R)-N-(2-Hydroxy-1-phenylethyl)ornithine amide Prepared according to the method described in Example 4(b) above from N$^\alpha$-Boc-N$^\delta$-Cbz-(R)-ornithine o-nitrophenyl ester (5.0 g; 11.5 mmol; see Example 4(a) above), (R)-(–)-phenylglycinol (1.58 g; 11.5 mmol) and 160 mL of $CH_2Cl_2$, yielding 3.9 g of the sub-title compound as a white solid.

$R_f$ 0.60 ($CH_2Cl_2$:MeOH (80:20); silica gel TLC plate)

¹H NMR (DMSO-$d_6$) δ1.66–1.25 (m, 4H), 1.40 (s, 9H), 2.95 (q, 2H), 3.56 (m, 2H), 3.96 (m, 1H), 4.82 (m, 2H), 5.05 (s, 2H), 6.85 (d, 1H, NH), 7.45–7.2 (m, 10H), 8.15 (d, 1H, NH).

(b) (R)-N⁵-(Cbz)-(R)-N-(2-hydroxy-1-phenylethyl)ornithine amide hydrochloride

Prepared according to the method described in Example 1(b) above from (R)-N²-(Boc)-N⁵-(Cbz)-(R)-N-(2-hydroxy-1-phenylethyl)ornithine amide (3.8 g; 7.82 mmol; from step (a) above), 50 mL of MeOH and 100 mL of HCl/EtOAc, isolating 2.68 g of the sub-title compound as white crystals.

(c) (R)-N⁵-(Cbz)-N²-(Diphenylacetyl)-(R)-N-(2-hydroxy-1-phenylethyl)-ornithine amide Prepared according to the method described in Example 1(d) above from (R)-N⁵-(Cbz)-(R)-N-(2-hydroxy-1-phenylethyl)ornithine amide hydrochloride (2.6 g; 6.16 mmol; from step (b) above), 2-nitrophenyl diphenyl acetate (2.37 g; 7.39 mmol; see Example 1(c) above) and triethylamine (1.28 mL; 9.24 mmol) in 150 mL of $CH_2Cl_2$, yielding 2.5 g of the sub-title compound as a white, crystalline material.

¹H NMR (DMSO-$d_6$) δ1.38 (m, 2H), 1.51 (m, 1H), 1.67 (m, 1H), 2.99 (m, 2H), 3.52 (m, 2H), 4.38 (m, 1H), 4.81 (m, 2H), 5.02 (s, 2H), 5.10 (s, 1H), 7.40–7.05 (m, 15H), 8.2 (d, 1H, NH), 8.45 (d, 1H, NH)

(d) (R)-N²-(Diphenylacetyl)-(R)-N-(2-hydroxy-1-phenylethyl)ornithine amide hydrochloride Prepared according to the method described in Example 1(e) above from a batch of (R)-N⁵-(Cbz)-N²-(diphenylacetyl)-(R)-N-(2-hydroxy-1-phenyl-ethyl)ornithine amide (2.5 g; from step (c) above), 10% Pd/C (200 mg), 100 mL of MeOH and 1.0 mL of concentrated HCl, yielding 1.8 g of the sub-title compound as a white foam.

$R_f$ 0.52 (EtOAc:hexanes (4:1))

¹H NMR (DMSO-$d_6$) δ1.52 (m, 3H), 1.72 (m, 1H), 2.73 (m, 2H), 3.52 (m, 2H), 4.41 (m, 1H), 4.75 (m, 2H), 4.85 (m, 1H), 5.11 (s, 1H), 7.25 (m, 15H), 8.45(d, 1H, NH), 8.55(d, 1H, NH)

(e) (R)-N$^\omega$,N$^{\omega'}$-bis(Cbz)-N²-(Diphenylacetyl)-(R)-N-(2-hydroxy-1-phenyl-ethylarginine amide Prepared according to the method described in Example 1(f) above from (R)-N²-(diphenylacetyl)-(R)-N-(2-hydroxy-1-phenylethyl)ornithine amide hydrochloride (0.5 g; 1.12 mmol), N,N'-bis(Cbz)-S-methylisothiourea (0.603 g; 1.68 mmol), DiPEA (0.2 mL) and DMF (15 mL) yielding 0.351 g of sub-title compound.

(f) (R)-N²-(Diphenylacetyl)-(R)-N-(2-hydroxy-1-phenylethyl)arginine amide hydrochloride Prepared according to the method described in Example 1(g) above from (R)-N$^\omega$,N$^{\omega'}$-bis(Cbz)-N²-(diphenylacetyl)-(R)-N-(2-hydroxy-1-phenyl-ethyl)-arginine amide (0.250 g;

from step (e) above), 10% Pd/C (200 mg) and, instead of HOAc, 50 mL of MeOH with 1 mL of concentrated HCl, yielding 69 mg of the title compound.

$^1$H NMR (CD$_3$OD) δ1.50 (m, 2H), 1.68 (m, 1H), 1.81 (m, 1R), 3.08 (m, 2H), 3.60 (m, 2H), 4.46 (m, 1H), 4.92 (m, 1H), 5.11 (s, 1H), 7.34 (m, 15H).

Example 18

(R)-N$^2$-(Diphenylacetyl-(S)-N-[2-hydroxy-1-(4-methoxyphenyl)ethyl]arginine amide hydrochloride (a) (R)-N$^2$-(Boc)-N$^5$-(Cbz)-(S)-N-[2-hydroxy-1-(4-methoxyphenyl)ethyl]ornithine amide Prepared according to the method described in Example 11(a) above from N$^α$-Boc-N$^δ$-Cbz-(R)-ornithine o-nitrophenyl ester (4.83 g; 9.91 mmol; see Example 4(a) above) with (S)-4-methoxy-α-hydroxymethylbenzylamine hydrochloride (2.22 g; 10.90 mmol) and triethylamine (1.50 g; 14.87 mmol; instead of DiPEA) in CH$_2$Cl$_2$ (150 mL), 18 hours reaction time. The reaction mixture was submitted to aqueous work up using water, 1N HCl and brine. The organic solution was dried, filtered and concentrated to give the sub-title compound as a yellow solid (4.0 g) which was used without purification.

R$_f$ 0.4 (CH$_2$Cl$_2$:MeOH (90:10); silica gel TLC plate)

(b) (R)-N$^5$-(Cbz)-(S)-N-[2-hydroxy-1-(4-methoxyphenyl) ethyl]-ornithine amide hydrochloride Prepared according to the method described in Example 1(b) above from crude (R)-N$^2$-(Boc)-N$^5$-(Cbz)-(S)-N-[2-hydroxy-l-(4-methoxyphenyl)ethyl]-ornithine amide (4.0 g; from step (a) above), EtOAc (100 mL) and HCl/EtOAc (100 mL), 18 hours reaction time. The hydrochloride salt was precipitated by the addition of diethyl ether, collected and dried to give the sub-title compound as a white solid (2.3 g).

$^1$H NMR (CD$_3$OD) δ1.45–1.57 (m, 2H), 1.78–1.92 (m, 2H), 3.10 (t, 2H), 3.72 (s, 3H), 3.68–3.82 (m, 2H), 3.98 (t, 1H), 4.98 (m, 1H), 5.03 (s, 2H), 6.88 (d, 2H), 7.25 (d, 2H), 7.25–7.40 (m, 5H).

(c) (R)-N$^5$-(Cbz)-N$^2$-(Diphenylacetyl)-(S)-N-[2-hydroxy-1-(4-methoxyphenyl)ethyl]ornithine amide Prepared according to the method described in Example 1(d) above from (R)-N$^5$-(Cbz)-(S)-N-[2-hydroxy-1-(4-methoxyphenyl)ethyl]ornithine amide hydrochloride (2.32 g, 5.13 mmol; from step (b) above), 2-nitrophenyl diphenyl acetate (1.81 g; 5.65 mmol; see Example 1(c) above), triethylamine (0.78 g, 7.70 mmol) and CH$_2$Cl$_2$ (150 mL), 60 hours reaction time. The reaction mixture was submitted to aqueous work up, dried, filtered and concentrated to give the crude product as an off-white solid (3.39 g). The crude product was chromatographed on silica gel eluting with CH$_2$C$_2$:MeOH (98:2). Concentration of the appropriate fractions gave pure sub-title compound as a white solid (2.85 g).

R$_f$ 0.4 (CH$_2$Cl$_2$:MeOH (95:5); silica gel TLC plate)

$^1$H NMR (CD$_3$OD) δ1.35–1.84 (m, 4H), 2.97–3.15 (m, 2H), 3.52–3.72 (m, 2H), 3.75 (s, 3H), 4.46 (m, 1H), 4.88 (m, 1H), 5.04 (s, 2H), 5.09 (s, 1H), 6.84 (d, 2H), 7.12–7.45 (m, 17H).

(d) (R)-N$^2$-(Diphenylacetyl)-(S)-N-[2-hydroxy-1-(4-methoxyphenyl)-ethyl]ornithine amide hydrochloride Prepared according to the method described in Example 1(e) above from (R)-N$^5$-(Cbz)-N$^2$-(diphenylacetyl)-(S)-N-[2-hydroxy-1 -(4-methoxyphenyl)-ethyl]ornithine amide (2.85 g; from step (c) above), 10% Pd/C (1.40 g), MeOH (200 mL) and concentrated HCl (2 mL) under hydrogen for 6 hours to give the crude product as a solid (2.6 g). Pure sub-title compound was obtained by crystallization from MeOH:diethyl ether to give a white solid (1.58 g).

mp 202–205° C.

R$_f$ 0.50 (MeOH:ammonium hydroxide (30:1); silica gel TLC plate)

$^1$H NMR (CD$_3$OD) δ1.52–1.95 (m, 4H), 2.86 (t, 2H), 3.62–3.75 (m, 2H), 3.78 (s, 3H), 4.47 (m, 1H), 4.88 (m, 1H), 5.15 (s, 1H), 6.86, (d, 2H), 7.18 (d, 2H), 7.15–7.43 (m, 10H).

(e) (R)-N$^ω$, N$^{ω'}$-bis(Cbz)-N$^2$-(Diphenylacetyl)-(R)-N-[2-hydroxy-1-(4-methoxyphenyl)ethyl]arginine amide Prepared according to the method described in Example 4(f) above from (R)-N$^2$-( diphenylacetyl)-(S)-N-[2-hydroxy-1-(4-methoxyphenyl)ethyl]ornithine amide hydrochloride (0.50 g; 0.98 mmol; from step (d) above), N,N'-bis (Cbz)-S-methylisothiourea (0.38 g; 1.07 mmol) and triethylamine (0.15 g; 1.46 mmol; instead of DiPEA) and dimethyl formamide (10 mL), 18 hours reaction time. Concentration under vacuum gave the crude product, which was chromatographed on silica gel eluting with CH$_2$C$_2$:EtOAc (3:1) to give pure sub-title compound as a solid (0.66 g).

R$_f$ 0.2 (CH$_2$Cl$_2$:EtOAc (3:1); silica gel TLC plate)

$^1$H NMR (CDCl$_3$) δ1.15–1.88 (m, 4H), 2.62 (t, 1H), 3.17–3.42 (m, 2H), 3.61–3.85 (m, 2H), 3.77 (s, 3H), 4.54 (m, 1H), 4.89–5.24 (m, 6H), 6.82 (d, 2H), 7.02–7.54 (m, 22H), 8.32 (m, 1H).

(f) (R)-N$^2$-(Diphenylacetyl)-(S)-N-[2-hydroxy-1-(4-methoxyphenyl)-ethyl]arginine amide hydrochloride Prepared according to the method described in Example 1(g) above from (R)-N$^ω$, N$^{ω'}$-bis(Cbz)-N$^2$-(diphenylacetyl)-(S)-N-[2-hydroxy-1-(4-methoxyphenyl)-ethyl]arginine amide (0.58 g; from step (e) above), 10% Pd/C (0.25 g) and HOAc (50 mL) under hydrogen, 5 hours reaction time. The crude product (0.42 g) was chromatographed on silica gel eluting with MeOH:CHCl$_3$:ammonium hydroxide (3:6:1) to afford the title compound as a solid (0.15 g).

mp 80–90° C.

R$_f$ 0.4 (System D)

$^1$H NMR (CD$_3$OD) δ1.42–1.93 (m, 4H), 3.01–3.18 (m, 2H), 3.66–3.72 (m, 2H), 3.78 (s, 3H), 4.46 (m, 1H), 4.87 (m, 1H), 5.17 (s, 1H), 6.84 (d, 2H), 7.17 (d, 2H), 7.20–7.38 (m, 10H).

Example 19

(R)-N$^2$-(Diphenylacetyl)-(R)-N-[2-hydroxy-1-(4-methoxyphenyl)ethyl]arginine amide hydrochloride (a) (R)-N$^2$-(Boc)-N$^5$-(Cbz)-(R)-N-[2-hydroxy-1-(4-methoxyphenyl)ethyl]ornithine amide Prepared according to the method described in Example 11(a) above from N$^α$-Boc-N$^δ$-Cbz-(R)-ornithine o-nitrophenyl ester (3.11 g; 6.38 mmol; see Example 4(a) above), (R)-4-methoxy-α-hydroxymethylbenzylamine hydrochloride (1.43 g; 7.02 mmol) and triethylamine (0.97 g; 9.57 mmol; instead of DiPEA) in CH$_2$Cl$_2$ (100 mL), 18 hours reaction time. The reaction mixture was submitted to aqueous work up using water, 1N HCl and brine, then dried, filtered and concentrated to give a yellow solid (3.69 g) which was used without purification.

R$_f$ 0.50 (System B)

(b) (R)-N$^5$-(Cbz)-(R)-N-[2-hydroxy-1-(4-methoxyphenyl) ethyl]ornithine amide hydrochloride Prepared according to the method described in Example 1(b) above from crude (R)-N$^2$-(Boc)-N$^5$-(Cbz)-(R)-N-[2-hydroxy-1-(4-methoxyphenyl)-ethyl]ornithine amide (3.7 g; from step (a) above), EtOAc (100 mL) and HCl/EtOAc (100 mL), 18 hours reaction time. The solution was concentrated to give the crude sub-title compound as a yellow crushable foam (3.3 g) which was used without purification.

(c) (R)-$N^5$-(Cbz)-$N^2$-(Diphenylacetyl)-(R)-N-[2-hydroxy-1-(4-methoxy-phenyl)ethyl]ornithine amide Prepared according to the method described in Example 1(d) above from (R)-$N^5$-(Cbz)-(R)-N-[2-hydroxy-1-(4-methoxyphenyl)ethyl]ornithine amide hydrochloride (3.33 g; 7.37 mmol; from step (b) above), 2-nitrophenyl diphenyl acetate (2.60 g; 8.10 mmol; see Example 1(c) above), triethylamine (2.23 g; 22.11 mmol) and $CH_2Cl_2$ (200 mL), reaction time 60 hours. The resulting yellow solution was submitted to aqueous work up, dried, filtered and concentrated to give the crude product as an off-white solid (4.76 g). The crude product was chromatographed twice on silica gel eluting with $CH_2Cl_2$:MeOH (98:2). Concentration of the product containing fractions gave the sub-title compound as a white solid (0.63 g).

$R_f$ 0.4 ($CH_2Cl_2$:MeOH (95:5); silica gel TLC plate)

$^1$H NMR ($CD_3OD$) δ1.44–1.90 (m, 4H), 3.02–3.18 (m, 2H), 3.55–3.70 (m, 2H), 3.68 (s, 3H), 4.48 (m, 1H), 4.92 (m, 1H), 5.03 (s, 1H), 5.07 (s, 2H), 6.78 (d, 2H), 7.06–7.45 (m, 17H)

(d) (R)-$N^2$-(Diphenylacetyl)-(R)-N-[2-hydroxy-1-(4-methoxyphenyl)ethyl]-ornithine amide hydrochloride Prepared according to the method described in Example 1(e) above from (R)-$N^5$-(Cbz)-$N^2$-(diphenylacetyl)-(R)-N-[2-hydroxy-1-(4-methoxyphenyl)-ethyl]ornithine amide (0.63 g; from step (c) above), 10% Pd/C (0.30 g), MeOH (100 mL) and concentrated HCl (1 mL) under hydrogen, 18 hours reaction time to give the crude sub-title compound as a solid (0.57 g) which was used without purification.

mp 208–212° C.

$R_f$ 0.5 (MeOH:ammonium hydroxide (30:1); silica gel TLC plate)

$^1$H NMR ($CD_3OD$) δ1.58–1.97 (m, 4H), 2.95 (t, 2H), 3.58–3.82 (m, 2H), 3.78 (s, 3H), 4.52 (m, 1H), 4.87 (m, 1H), 5.06 (s, 1H), 6.80, (d, 2H), 7.15 (d, 2H), 7.12–7.42 (m, 10H)

e) (R)-$N^ω$,$N^{ω'}$-bis(Cbz)-$N^2$-(Diphenylacetyl)-(S)-N-[2-hydroxy-1-(4methoxyphenyl)ethyl]arginine amide Prepared according to the method described in Example 4(f) above from (R)-$N^2$-(diphenylacetyl)-(R)-N-[2-hydroxy-1-(4-methoxyphenyl) ethyl]ornithine amide hydrochloride (0.57 g; 1.11 mmol; from step (d) above), N,N'-bis(Cbz)-S-methylisothiourea (0.44 g; 1.22 mmol), triethylamine (0.17 g; 1.67 mmol; instead of DiPEA) and dimethyl formamide (10 mL), 60 hours reaction time. Concentration under vacuum gave the crude product which was chromatographed on silica eluting with $CH_2Cl_2$:EtOAc (3:1), then $CH_2Cl_2$:EtOAc (1:1), to give pure sub-title compound as a solid (0.48 g).

$R_f$ 0.3 ($CH_2Cl_2$:EtOAc (3:1); silica gel TLC plate)

$^1$H NMR ($CDCl_3$) δ1.42–1.98 (m, 4H), 2.85–3.02 (m, 1H), 3.15–3.37 (m, 2H), 3.55–3.86 (m, 2H), 3.77 (s, 3H), 4.56 (m, 1H), 4.82–5.23 (m, 6H), 6.78 (d, 2H), 6.92–7.54 (m, 22H), 8.36 (m, 1H)

(f) (R)-$N^2$-(Diphenylacetyl)-(R)-N-[2-hydroxy-1-(4-methoxyphenyl)-ethyl]arginine amide hydrochloride Prepared according to the method described in Example 1(g) above from (R)-$N^ω$,$N^{ω'}$-bis(Cbz)-$N^2$-(diphenylacetyl)-(S)-N-[2-hydroxy-1-(4-methoxy-phenyl)ethyl]arginine amide (0.48 g; from step (e) above), 10% Pd/C (0.25 g) and HOAc (50 mL) under hydrogen, 18 hours reaction time. The crude product (0.37 g) was chromatographed on silica gel eluting with MeOH:$CHCl_3$:ammonium hydroxide (3:6:1), to afford the title compound as a solid (0.11 g).

mp 80–90° C.

$R_f$ 0.4 (System D)

$^1$H NMR ($CD_3OD$) δ1.50–1.95 (m, 4H), 3.16 (t, 2H), 3.58–3.77 (m, 2H), 3.76 (s, 3H), 4.50 (t, 1H), 4.87 (m, 1H), 5.08 (s, 1H), 6.81 (d, 2H), t0 7.17(d, 2H), 7.20–7.35(m, 10H)

Example 20

(R)-$N^2$-(Diphenylacetyl)-(S)-N-[1-(4-hydroxyphenyl)ethyl]arginine amide hydrochloride (a) (R)-$N^2$-(Boc)-$N^5$-(Cbz)-(S)-N-[1-(4-hydroxyphenyl) ethyl]ornithine amide Prepared according to the method described in Example 1(a) above from $N^α$-Boc-$N^δ$-Cbz-(R)-ornithine (5.34 g; 14.56 mmol), (S)-4-hydroxy-α-methylbenzylamine (2.0 g; 14.56 mmol), BOP reagent (9.67 g; 21.9 mmol), triethylamine (2.5 mL; instead of DiPEA) in acetonitrile (100 mL; instead of acetonitrile:$CH_2Cl_2$( 1:1)) to yield the sub-title compound (6.7g) as a white foam. The crude $^1$H NMR was consistent with the structure.

(b) (R)-$N^5$-(Cbz)-(S)-N-[1-(4-hydroxyphenyl)ethyl] ornithine amide hydrochloride Prepared according to the method described in Example 1(b) above from (R)-$N^2$-(Boc)-$N^5$-(Cbz)-(S)-N-[1-(4-hydroxyphenyl)ethyl]ornithine amide (5.1 g; from step (a) above), ethyl acetate (100 mL) and HCl/EtOAc (100 mL) yielding, after isolation, 3.3 g of the sub-title compound as a tan solid.

(c) (R)-$N^5$-(Cbz)-$N^2$-(Diphenylacetyl)-(S)-N-[1-(4-hydroxyphenyl)ethyl]ornithine amide Prepared according to the method described in Example 3(c) above from (R)-$N^5$-(Cbz)-(S)-N-[1-(4-hydroxyphenyl) ethyl]ornithine amide hydrochloride (3.3 g; 7.8 mmol; from step (b) above), diphenylacetic acid (1.82 g, 8.6 mmol), BOP (3.79 g; 8.58 mmol) and triethylamine (4.0 mL; 1.1 eq.) in 300 mL acetonitrile, yielding 895 mg of the sub-title compound.

$^1$H NMR ($CD_3OD$) δ1.38 (d, 3H), 1.45 (m, 2H), 1.61 (m, 1H), 1.78 (m, 1H), 3.08(m,2H), 4.40 (m, 1H), 4.89 (q, 1H), 5.03 (s, 1H), 5.04 (s, 2H), 6.68 (d, 2H), 7.05 (d, 2H), 7.4 (m, 15H), 8.08 (d, 1H, NH) (d) (R)-$N^2$-(Diphenylacetyl)-(S)-N-[1-(4-hydroxyphenyylethyl]ornithine amide hydrochloride Prepared according to the method described in Example 1(e) above from (R) -$N^5$-(Cbz)-$N^2$-(diphenylacetyl)-(S)-N-[1 -(4-hydroxyphenyl) ethyl]ornithine amide (895 mg; from step (c) above), 10% Pd/C (300 mg) in methanol (100 mL) with HCl (0.5 mL), yielding 65 mg of the sub-title compound.

$R_f$ 0.66 (EtOAc:MeOH:conc. ammonium hydroxide (47:47:6))

$^1$H NMR ($CD_3OD$) δ1.36 (d, 3H), 1.66 (m, 3H), 1.85 (m, 1H), 2.90 (m, 2H), 4.41 (m, 1H), 5.07 (s, 1H), 6.68 (d, 2H), 7.05 (d, 2H), 7.3 (m, 10H), 8.1 (d, 1H, NH), 8.40 (d, 1H, NH).

(e)(R)-$N^ω$,$N^{ω'}$-(bisCbz)-$N^2$-(Diphenylacetyl)-(S)-N-[1-(4-hydroxyphenyl)-ethyl]arginine amide Prepared according to the method in Example 4(f) above from (R)-$N^2$-(diphenylacetyl)-(S)-N-[1-(4-hydroxyphenyl) ethyl]ornithine amide hydrochloride (0.5 g; from step (d) above), N,N'-bis(Cbz)-S-methyisothiourea (0.4 g) and DiPEA (0.2 mL) in DMF (10 mL), yielding 526 g of the sub-title compound as a white foam.

$R_f$ 0.90 (EtOAc)

f) (R)-$N^2$-(Diphenylacetyl)-(S)-N-[1-(4-hydroxyphenyl) ethyl]arginine amide hydrochloride prepared according to the method described in Example 1(g) above from R)-$N^ω$,$N^{ω'}$-(bisCbz)-$N^2$-(diphenylacetyl)-(S)-N-[1-(4-hydroxyphenyl)ethyl]-arginine amide (250 mg; from step (e) above), HOAc (10 mL) and 10% Pd/C (0.2 g) treated with methanol and ethyl acetate saturated with HCl to give 125 mg of the title compound.

mp 146–148° C.

$R_f$ 0.18 (EtOAc:MeOH:concentrated ammonium hydroxide (47:47:6))

$^1$H NMR (CD$_3$OD) δ1.35 (d, 3H), 1.55 (m, 2H), 1.66 (m, 1H), 1.82 (m, 1H), 3.11(m, 2H), 4.41 (q, 1H), 4.90 (q, 1H), 5.07 (s, 1H), 6.58 (d, 2H), 7.05 (d, 2H)

Example 21

(R)-N$^2$-(Diphenylacetyl)-(R, S)-N-[1-(4-methoxyphenyl)ethyl]arginine amide hydrochloride (a) (R)-N$^2$-(Boc)-N$^5$-(Cbz)-(R,S)-N-[1-(4-methoxyphenyl)ethyl]ornithine amide Prepared according to the method described in Example 1(a) above from N$^\alpha$-Boc-N$^\delta$-Cbz-(R)-ornithine (2.5 g; 6.7 mmol), BOP reagent (3.3 g; 7.4 mmol), HOBT (1.1 g; 7.4 mmol), DiPEA (5.8 mL; 33 mmol) and 100 mL of acetonitrile:CH$_2$Cl$_2$ (1:1) followed by (R,S)-4-methoxy-δ-methylbenzylamine (1.0 g; 6.7 mmol; in 5 mL of acetonitrile). After work up the crude product was used without further purification. The yield of crude sub-title compound was 3.3 g (100%).

$^1$H NMR (CDCl$_3$) δ1.38–1.72 (m, 5H), 1.49+1.51 (s, 9H), 1.72–2.00 (m, 2H), 3.10–3.28+3.35–3.55(m, 2H), 3.28 +3.33 (s, 3H), 4.18–4.40 (m, 1H), 4.82–5.25 (m, 3H), 6.68–6.80 (m, 1H), 6.82–6.95 (m, 2H), 7.22–7.45 (m, 7H)

(b) (R)-N$^5$-(Cbz)-N$^2$-(Diphenylacetyl)-(R, S)-N-[1-(4-methoxyphenyl)-ethyl]ornithine amide Prepared analogously to the method described in Examples 2(b) and 2(c) above from (R)-N$^2$-(Boc)-N$^5$-(Cbz)-(R,S)-N-[1-(4-methoxyphenyl)ethyl]-ornithine amide (3.3 g; 6.7 mmol; from step (a) above), HCl/EtOAc (75 mL), 30 minutes reaction time for the deprotection, then THF (200 mL; instead of CH$_2$Cl$_2$), diphenylacetyl chloride (1.7 g; 7.4 mmol) followed by DiPEA (4.7 mL; 27 mmol) over 5 min, 1 hour reaction time. The solvent was evaporated at reduced pressure and the resultant residue dissolved in CH$_2$Cl$_2$ (300 mL) for the work up procedure. The crude material was purified to yield 2.0 g (51%) of the sub-title compound as a crushable foam.

(c) (R)-N$^2$-(Diphenylacetyl)-(R,S)-N-[1-(4-methoxyphenyl)ethyl]ornithine amide hydrochloride Prepared according to the method described in Example 1(e) above from (R)-N$^5$-(Cbz)-N$^2$-(diphenylacetyl)-(R,S)-N-[1-(4-methoxyphenyl)ethyl]-ornithine amide (2.0 g; 3.4 mmol; from step (b) above), 10% Pd/C (w/w; 500 mg), ethanol (150 mL; instead of methanol) and conc. HCl (1 mL), 2 hours reaction time, to yield the sub-title compound as a foam (1.5 g; 87%). A sample was crystallised from acetonitrile.

mp 198–201° C.

(d) (R)-N$^\omega$,N$^{\omega\prime}$-bis(Cbz)-N$^2$-(Diphenylacetyl)-(R,S)-N-[1-(4-methoxyphenyl)ethyl]arginine amide Prepared according to the method described in Example 4(f) from (R)-N$^2$-(diphenylacetyl)-(R,S)-N-[1-(4-methoxyphenyl)ethyl]ornithine amide hydrochloride (1.08 g; 2.17 mmol; from step (c) above), N,N'-bis(Cbz)-S-methylisothiourea (0.780 g; 2.17 mmol) and triethylamine (0.6 mL; 4.35 mmol) in THF (40 mL), yielding 720 mg of the sub-title compound as a white solid.

(e) (R)-N$^2$-(Diphenylacetyl)-(R,S)-N-[1-(4-methoxyphenyl)ethyl]arginine amide hydrochloride Prepared according to the method described in Example 1(g) from (R)-N$^\omega$,N$^{\omega\prime}$-bis(Cbz)-N$^2$-(diphenylacetyl)-(R,S)-N-[1-(4-methoxyphenyl)ethyl]arginine amide (440 mg; from step (d) above), 10% Pd/C (100 mg), ethanol (20 mL) and concentrated hydrochloric acid (0.2 mL) under hydrogen, 18 hours reaction time, yielding 174 mg of the title compound as a white solid.

[α]$_D^{20}$=+21.8° C. (c=2.0; methanol)
mp=84–88° C.

R$_f$ =0.47 (CH$_2$Cl$_2$:MeOH (80:20))

$^1$H NMR (CD$_3$OD) 1.62 (d, 3H), 1.62–2.20 (m, 3H), 3.42 (m, 2H), 4.05 (s, 3H), 4.48 (m, 1H), 5.20 (q, 1H), 5.38 (s, 0.5H), 5.41 (s, 0.5H), 7.10 (d, 2H), 7.13 (d, 2H), 7.48 (d, 2H), 7.51 (d, 2H), 7.68 to 7.51 (m, 10H)

Example 22

(R)-N$^2$-(Diphenylacetyl)-N-methyl-(R)-N-(1-phenylethyl)arginine amide hydrochloride (a) (R)-N$^2$-(Boc)-N$^5$-(Cbz)-N-methyl-(R)-N-(1-phenylethyl)ornithine amide Prepared according to the method described in Example 1(a) above from N$^\alpha$-Boc-N$^\delta$-Cbz-(R)-ornithine (5.0 g; 13 mmol), BOP reagent (6.0 g; 13 mmol), HOBT (1.8 g; 13 mmol), DiPEA (7.1 mL; 40 mmol) and acetonitrile:CH$_2$Cl$_2$ (1:1; 100 mL) followed by (R)-(+)-N,α-dimethylbenzylamine (2.0 mL; 13 mmol), then stirred overnight. After work up the crude product was purified by chromatography on silica gel with EtOAc to provide 6.0 g (91%) of the sub-title compound.

(b) (R)-N$^5$-(Cbz)-N$^2$-(Diphenylacetyl)-N-methyl-(R)-N-(1-phenylethyl)ornithine amide Prepared according to the method described in Examples 2(b) and 2(c) above from (R)-N$^2$-(Boc)-N$^5$-(Cbz)-N-methyl-(R)-N-(1-phenylethyl)ornithine amide (5.0 g; 10 mmol; from step (a) above) EtOAc (75 mL) then HCl/EtOAc (75 mL), 2 hours reaction time for the deprotection, then CH$_2$Cl$_2$ (50 mL), diphenylacetyl chloride (2.4 g; 10 mmol) followed by pyridine (3.0 mL; 37 mmol; instead of DiPEA) over 1 minute, overnight reaction time, diluted with CH$_2$Cl$_2$ (100 mL) for the work up procedure. The crude material was purified by chromatography on silica gel with EtOAc:hexanes (1:1) to provide 1.6 g (26%) of the sub-title compound.

(c) (R)-N$^2$-(Diphenylacetyl)-N-methyl-(R)-N-(1-phenylethyl)ornithine amide

Prepared according to the method described in Example 1(e) above from (R)-N$^5$-(Cbz)-N$^2$-(diphenylacetyl)-N-methyl-(R)-N-(1-phenylethyl)ornithine amide (1.6 g; 2.8 mmol; from step (b) above), 10% Pd/C (w/w; 100 mg), HOAc (75 mL), overnight reaction time. The crude acetate salt was purified by chromatography on silica gel with EtOAc, then CHCl$_3$:MeOH:concentrated ammonium hydroxide (6:3:1) to provide 1.2 g (98%) of the sub-title compound.

(d) (R)-N$^2$-(Diphenylacetyl)-(N$^\omega$,N$^{\omega\prime}$)-bis(Cbz)-N-methyl-(R)-N-(1-phenylethyl)arginine amide Prepared according to the method described in Example 1(f) above from (R)-N$^2$-(diphenylacetyl)-N-methyl-(R)-N-(1-phenylethyl)ornithine amide (0.50 g; 1.1 mmol; from step (c) above), N,N'-bis(Cbz)-S-methylisothiourea (0.40 g; 1.1 mmol), DiPEA (0.41 mL; 2.4 mmol) and THF (20 mL; instead of DMF). The crude product was purified by chromatography on silica gel with CH$_2$Cl$_2$, then EtOAc to provide 0.62 g (79%) of the subtitle compound as a solid.

(e) (R)-N$^2$-(Diphenylacetyl)-N-methyl-(R)-N-(1-phenylethyl)arginine amide hydrochloride Prepared according to the method described in Example 1(g) above from (R)-N$^2$-(diphenylacetyl)-(N$^\omega$,N$^{\omega\prime}$)-(bisCbz)-N-methyl-(R)-N-(1-phenylethyl)arginine amide (0.62 g; 0.89 mmol; from step (d) above), 10% Pd/C (w/w; 100 mg), HOAc (50 mL), overnight reaction time. The crude acetate salt was converted to the hydrochloride then triturated with methanol to provide 0.12 g (25%) of the title compound as a solid.

mp 233–235° C.
R$_f$ 0.50 (System D)
[α]$_D^{21}$=+109.7°(C=0.31, MeOH)

¹H NMR (CD₃OD) δ1.46 and 1.66 (2d, 3H), 1.50–1.90 (m, 4H), 2.59 and 2.73 (2s, 3H), 3.16 (m, 2H), 4.88 (m, 1H), 5.03 and 5.10 (2s, 1H), 5.38 and 5.88 (2m, 1H), 7.15–7.37 (m, 10H)

Example 23

(R)-N²-(Diphenylacetyl)-N-methyl-(S)-N-(1-phenylethyl)arginine amide hydrochloride (a) (R)-N²-(Boc)-N⁵-(Cbz)-N-methyl-(S)-N-(1-phenylethyl) ornithine amide Prepared according to the method described in Example 1(a) above from N^α-Boc-N^δ-Cbz-(R)-ornithine (5.0 g; 13 mmol), BOP reagent (6.0 g; 13 mmol), HOBT (1.8 g; 13 mmol), DiPEA (7.1 mL; 40 mmol) and 100 mL of acetonitrile:CH₂Cl₂ (1:1) followed by (S)-(−)-N,α-dimethylbenzylamine (2.0 mL; 13 mmol), then stirred overnight. After work up the crude product was purified by chromatography on silica gel with EtOAc to provide 5.5 g (83%) of the sub-title compound.

(b) (R)-N⁵-(Cbz)-N²-(Diphenylacetyl)-N-methyl-(S)-N-(1-phenylethyl)-ornithine amide Prepared according to the method described in Examples 2(b) and 2(c) above from (R)-N²-(Boc)-N⁵-(Cbz)-N-methyl-(S)-N-(1-phenylethyl)-ornithine amide (5.3 g; 11 mmol; from step (a) above), EtOAc (75 mL), then HCl/EtOAc (75 mL), 2.5 hours reaction time for the deprotection, then CH₂Cl² (50 mL), diphenylacetyl chloride (2.6 g; 11 mmol) followed by pyridine (3.0 mL; 37 mmol; instead of DiPEA) over 1 min, overnight reaction time, diluted with CH₂Cl₂ (100 mL) for the work-up procedure. The crude material was purified by chromatography on silica gel with EtOAc:hexane (1:1) to provide 1.9 g (30%) of the sub-title compound.

(c) (R)-N²-(Diphenylacetyl)-N-methyl-(S)-N-(1-phenylethyl)ornithine amide

Prepared according to the method described in Example 1(e) above from (R)-N⁵-(Cbz)-N²-(diphenylacetyl)-N-methyl-(S)-N-(1-phenylethyl)ornithine amide (1.9 g; 3.3 mmol; from step (b) above), 10% Pd/C (w/w; 100 mg), HOAc (75 mL), overnight reaction time. The crude acetate salt was purified by chromatography on silica gel with EtOAc, then CHCl₃:MeOH:concentrated ammonium hydroxide (6:3:1) to provide 1.4 g (96%) of the sub-title compound.

(d) (R)-(N^ω,N^ω'-(bisCbz)-N²-(Diphenylacetyl)-N-methyl-(S)-N-(1-phenylethyl)arginine amide Prepared according to the method described in Example 1(f) above from (R)-N²-(diphenylacetyl)-N-methyl-(S)-N-(1-phenylethyl)ornithine amide (0.50 g; 1.1 mmol; from step (c) above), N,N'-bis(Cbz)-S-methyliso-thiourea (0.40 g; 1.1 mmol), DiPEA (0.41 mL; 2.4 mmol) and THF (20 mL; instead of DMF). The crude product was purified by chromatography on silica gel with CH₂Cl₂, then EtOAc to provide 0.71 g (91%) of the sub-title compound as a solid.

(e) (R)-N²-(Diphenylacetyl)-N-methyl-(S)-N-(1-phenylethyl)arginine amide hydrochloride Prepared according to the method described in Example 1(g) above from (R)-(N^ω,N^ω')-bis(Cbz)-N²-(diphenylacetyl)-N-methyl-(S)-N-(1-phenylethyl)-arginine amide (0.70 g; 1.0 mmol; from step (d) above), 10% Pd/C (w/w; 100 mg), HOAc (50 mL), overnight reaction time. The crude acetate salt was converted to the hydrochloride then triturated with methanol to provide 0.15 g (28%) of the title compound as a solid.

mp 251–253° C.

R_f 0.50 (System D)

$[\alpha]_D^{21} = -21.2$ (C=0.34; MeOH)

¹H NMR (CD₃OD) δ1.40 and 1.51 (2d, 3H), 1.52–1.92 (m, 4H), 2.70 and 2.72 (2s, 3H), 3.03–3.24 (m, 2H), 4.90 (m, 1H), 5.05 and 5.08 (2s, 1H), 5.28 and 5.90 (2m, 1H), 7.17–7.39 (m, 10H)

Example 24

(R)-N²-(Diphenylacetyl)-(R,S)-N-[1-(4-cylopropylmethoxyphenyl)ethyl]-arginine amide hydrochloride (a) (R)-N²-(Boc)-N⁵-(Cbz)-(R,S)-N-[1-(4-Cyclopropylmethoxyphenyl)-ethyl]ornithine amide A solution of N^α-Boc-N^δ-Cbz-(R)-ornithine-o-nitrophenyl ester (0.9 g; 1.86 mmol; see Example 4a above), (R,S)-[1-(4-cyclopropylmethoxyphenyl)-ethylamine (0.48 g, 1.86 mmol), triethylamine (0.39 mL, 2.79 mmol) in CH₂Cl₂ (50 mL) was stirred for 5 h at room temperature. The resultant yellow solution was concentrated in vacuo and the residue chromatographed on silica eluting with CH₂Cl₂:CH₃OH (98:2). Fractions containing the desired product were combined and concentrated in vacuo to afford 0.67 g (67%) of the sub-title compound as a crushable foam.

R_f 0.5 (CH₂Cl₂:CH₃OH(95:5))

¹H NMR (CDCl₃) δ0.28–0.38 (m, 2H), 0.58–0.68 (m, 2H), 1.26 (m, 1H), 1.34–1.88 (m, 16H), 3.14 (m, 1H), 3.42 (m, 1H), 3.71 and 3.78 (d, 2H), 4.22 (m, 1H), 4.78–5.27 (m, 5H), 6.68 (m, 1H), 6.79–6.87 (m, 2H), 7.21 (d, 2H), 7.26–7.41 (m, 5H)

(b) (R)-N⁵-(Cbz)-(R,S)-N-[1-(4-Cyclopropylmethoxyphenyl)ethyl]-ornithine amide

A solution of (R)-N²-(Boc)-N⁵-(Cbz)-(R,S)-N-[1-(4-cyclopropylmethoxy-phenyl)ethyl]ornithine amide (0.67g, 1.30 mmol; from step (a) above) in EtOAc was treated with HCl/EtOAc (10 mL). After stirring for 5 h, the reaction was concentrated in vacuo to provide 0.62 g (100%) as a crushable foam.

R_f 0.3 and 0.4 (CHCl₃:CH₃OH:AcOH(9:1:0.1))

¹H NMR (CD₃OD) δ0.28–0.37 (m, 2H), 0.52–0.65 (m, 2H), 1.21 (m, 1H), 1.38–1.53 (m, 3H), 1.55–1.68 (m, 2H), 1.71–1.93 (m, 2H), 3.02–3.22 (m, 2H), 3.69–3.90 (m, 3H), 4.89–5.11 (m, 3H), 6.79–6.88 (m, 2H), 7.16-7.38 (m, 7H)

(c) (R)-N⁵-(Cbz)-N²-(Diphenylacetyl)-(R,S)-N-[1-(4-cyclopropylmethoxy-phenyl)ethyl]ornithine amide A solution of 2-nitrophenyl diphenyl acetate (0.42 g, 1.30 mmol; see Example 1(c) above), (R)-N⁵-(Cbz)-(R,S)-N-[1-(4-cyclopropylmethoxy-phenyl)ethyl]ornithine amide (0.62 g, 1.30 mmol; from step (b) above) and triethylamine (0.54 mL, 3.90 mmol) in CH₂Cl₂ (50 mL) was stirred at room temperature for 18 h. The resultant yellow solution was concentrated in vacuo and chromatographed on silica eluting with CH₂Cl₂:EtOAc (5:1). Fractions containing the desired product were combined and concentrated to afford 0.71 g (86%) of the sub-title compound.

R_f 0.5 (CH₂Cl₂:EtOAc (3:1))

¹H NMR (CDCl₃) δ0.27–0.39 (m, 2H), 0.57–0.68 (m, 2H), 1.24 (m, 1H), 1.32–1.90 (m, 7H), 3.08 (m, 1H), 3.37 (m, 1H), 3.70 and 3.76 (d, 2H), 4.63 (m, 1H), 4.79–5.12 (m, 5H), 6.53 (m, 1H), 6.79 (d, 2H), 6.88 (m, 1H) 7.13 (d, 2H), 7.14–7.41 (m, 15H)

(d) (R)-N²-(Diphenylacetyl)-(R,S)-N-[1-(4-cyclopropylmethoxyphenyl-ethyl]ornithine amide To a solution of (R)-N⁵-(Cbz)-N²-(diphenylacetyl)-(R,S)-N-[1-(4-cyclo-propylmethoxyphenyl)ethyl]ornithine amide (0.71 g, 1.12 mmol; from step (c) above) at 0° C. in acetonitrile (40 mL) was added TMSI (0.21 mL, 1.46 mmol). The resultant solution was stirred for 1 h in the cold, then quenched with H₂O. EtOAc and NaHCO₃ solution were then added. The EtOAc layer was separated, washed with 1M Na₂S₂O₃ (once) and brine (twice), dried over Na₂SO₄ and concentrated in vacuo. The residue was chromatographed on silica eluting with $CH_2Cl_2$:$CH_3OH$:$NH_4OH$ (88.5:10:1.5). Fractions containing the desired product were combined and concentrated in vacuo and converted to the hydrochloride salt, affording 0.17 g (30%) of the sub-title compound.

$R_f$ 0.60 (System C)

$^1H$ NMR ($CD_3OD$) δ0.29–0.38 (m, 2H), 0.55–0.66 (m, 2H), 1.23 (m, 1H), 1.30–1.85 (m, 7H), 2.57 and 2.62 (t, 2H), 3.73–3.82 (m, 2H), 4.38 (m, 1H), 4.88 (m, 1H), 5.05 and 5.08 (s, 1H), 6.78 and 6.83 (d, 2H), 7.08–7.37 (m, 12H)

(e) (R)-$N^2$-(Diphenylacetyl)-(R,S)-N-[1-(4-cyclopropylmethoxyphenyl)-ethyl]arginine amide hydrochloride A solution of(R)-$N^2$-(diphenylacetyl)-(R,S)-N-[1-(4-cyclopropylmethoxy-phenyl)ethyl]ornithine amide (0.17 g; 0.34 mmol; from step (d) above), 1H-pyrazole-1-carboxamidine hydrochloride (0.05 g; 0.34 mmol) and triethylamine (0.07 g; 0.68 mmol) in DMF (5 mL) was stirred for 24 h at room temperature. The solution was concentrated in vacuo and the residue chromatographed on silica eluting with $CHCl_3$:$CH_3OH$:$NH_4OH$ (6:3:1). Fractions containing the desired compound were combined and concentrated in vacuo and then converted to the hydrochloride salt to afford 0.12 g (61%) of the title compound as a solid.

$R_f$ 0.5 (System D)

$^1H$ NMR ($CD_3OD$) δ0.32–0.38 (m, 2H), 0.57–0.66 (m, 2H), 1.24 (m, 1H), 1.38 (d, 3H), 1.41–1.89 (m, 4H), 3.05–3.18 (m, 2H), 3.78 (d, 2H), 4.41 (m, 1H), 4.87 (m, 1H), 5.07 and 5.12 (s, 1H), 6.77 and 6.82 (d, 2H), 7.11–7.17 (m, 2H), 7.18–7.37 (m, 10H)

Example 25

(R)-$N^2$-(Diphenylacetyl)-(R)-N-[1-(4-benzyloxyphenyl)ethyl]arginine amide hydrochloride (a) (R)-$N^2$-(Boc)-$N^5$-(Cbz)-(R)-N-[1-(4-Benzyloxyphenyl)ethyl]ornithine amide Prepared according to the method described in Example 4(b) above from $N^\alpha$-Boc-$N^\delta$-Cbz-(R)-ornithine-o-nitrophenyl ester (3.11 g; 6.37 mmol), (R)-4-benzyloxy-α-methylbenzylamine hydrochloride (1.68 g; 6.37 mmol), TEA (1.94 g; 19.10 mmol) and $CH_2Cl_2$ (200 mL), 18 hours reaction time. The resultant yellow solution was concentrated to afford the crude sub-title compound which was used directly in the next step.

$R_f$ 0.70 (System B)

(b) (R)-$N^5$-(Cbz)-(R)-N-[1-(4-Benzyloxyphenyl)ethyl]ornithine amide hydrochloride Prepared according to the method described in Example 1(b) above from crude (R)-$N^2$-(Boc)-$N^5$-(Cbz)-(R)-N-[1-(4-benzyloxyphenyl)ethyl]-ornithine amide (6.37 mmol; from step (a) above), EtOAc (200 mL) and HCl/EtOAc (75 mL), 3 hours reaction time. The resultant heterogeneous solution was concentrated to 100 mL, slurried with $Et_2O$ and the solids collected and dried to afford the sub-title compound as a white solid (2.5 g; 75%).

$R_f$ 0.30 ($CHCl_3$, $CH_3OH$, AcOH (9:1:0.1))

$^1H$ NMR ($CD_3OD$) δ1.38–1.58 (m, 2H), 1.47 (d, 3H), 1.72–1.90 (m, 2H), 3.08 (t, 2H), 3.87 (t, 1H), 4.88–5.12 (m, 5H), 6.95 (d, 2H), 7.17–7.43 (m, 12H)

(c) (R)-$N^5$-(Cbz)-$N^2$-(Diphenylacetyl)-(R)-N-[1-(4-benzyloxyphenyl)-ethyl]ornithine amide Prepared according to the method described in Example 1(d) above from (R)-$N^5$-(Cbz)-(R)-N-[1-(4-benzyloxyphenyl)ethyl]ornithine amide hydrochloride (2.5 g; 4.88 mmol; from step (b) above), 2-nitrophenyl diphenyl acetate (1.6 g; 4.88 mmol; see Example 1(c) above), TEA (1.5 g; 14.64 mmol) and $CH_2Cl_2$ (200 mL) at room temperature, 18 hours reaction time, followed by additional 2-nitrophenyl diphenyl acetate (0.6 g) and TEA (0.7 g) at reflux, 18 hours reaction time. The resulting solution was concentrated and chromatographed on silica eluting with $CH_2Cl_2$:EtOAc (5:1) to afford the pure sub-title compound as a solid (2.9 g).

$R_f$ 0.60 ($CH_2Cl_2$, EtOAc (3:1))

$^1H$ NMR ($CDCl_3$) δ1.27–1.59 (m, 6H), 1.75 (m, 1H), 3.04 (m, 1H), 3.40 (m, 1H), 4.68 (m, 1H), 4.78–5.06 (m, 6H), 6.58 (d, 1H), 6.87 (d, 2H), 6.95 (d, 1H), 7.16 (d, 2H), 7.18–7.43 (m, 20H)

(d) (R)-$N^2$-(Diphenylacetyl)-(R)-N-[1-(4-benzyloxyphenyl)ethyl]ornithine amide Prepared according to the method described in Example 6(d) above from (R)-$N^5$-(Cbz)-$N^2$-(diphenylacetyl)-(R)-N-[1-(4-benzyloxyphenyl)ethyl]-ornithine amide (1.0 g; 1.49 mmol; from step (c) above), trimethylsilyliodide (0.33 g; 1.64 mmol) and $CH_3CN$ (35 mL) at 0° C., 2 hours reaction time. The resultant heterogeneous solution was submitted to aqueous work up and chromatographed on silica eluting with $CH_2Cl_2$:MeOH:conc. $NH_4OH$ (88.5:10:1.5) to afford the sub-title compound as a solid (0.7 g).

$R_f$ 0.40 (System C)

$^1H$ NMR ($CDCl_3$) δ1.22–1.43 (m, 2H), 1.36 (d, 3H), 1.62–1.83 (m, 2H), 2.50–2.67 (m, 2H), 4.49 (q, 1H), 4.93 (s, 1H), 4.97 (t, 1H), 5.04 (s, 2H), 6.88 (d, 2H), 7.09–7.45 (m, 17H)

(e) (R)-$N^2$-(Diphenylacetyl)-(R)-N-[1-(4-benzyloxyphenyl)ethyl]arginine amide hydrochloride Prepared according to the method described in Example 6(e) above from (R)-$N^2$-(diphenylacetyl)-(R)-N-[1-(4-benzyloxyphenyl)ethyl]ornithine amide (0.38 g; 0.71 mmol; from step (d) above), 1H-pyrazole-1-carboxamidine monohydrochloride (0.10 g; 0.71 mmol), TEA (0.14 g, 1.42 mmol) and DMF (5 mL), 18 hours reaction time. The resulting solution was concentrated and chromatographed on silica eluting with MeOH:$CHCl_3$:conc. $NH_4OH$ (3:6:1) and converted to the hydrochloride salt to afford the title compound as a white solid (0.32 g).

mp 148–152° C.

$R_f$ 0.50 (System D)

$^1H$ NMR ($CD_3OD$) δ1.38 (d, 3H), 1.41–1.87 (m, 4H), 3.02–3.18 (m, 2H), 4.41 (t, 1H), 4.92 (q, 1H), 5.06 (s, 2H), 5.11 (s, 1H), 6.92 (d, 2H), 7.17 (d, 2H), 7.18–7.46 (m, 15H)

Example 26

(R)-$N^2$-(Diphenylacetyl)-(R,S)-N-[1-(4-phenoxyphenyl)ethyl]arginine amide hydrochloride (a) (R)-$N^2$-(Boc)-$N^5$-(Cbz)-(R,S)-N-[1-(4-phenoxyphenyl)ethyl]ornithine amide Prepared according to the method described in Example 4(b) above from $N^\alpha$-Boc-$N^\delta$-Cbz-(R)-ornithine-o-nitrophenyl ester (3.0 g; 6.15 mmol; see Example 4(a) above), (R,S)-4-phenoxy-α-methylbenzylamine (1.3 g; 6.15 mmol) and $CH_2Cl_2$ (150 mL), 24 hours reaction time. The resultant yellow solution was concentrated and chromatographed on silica eluting with $CH_2Cl_2$:MeOH (98:2 then 95:5) to afford the sub-title compound as a crushable foam (2.6 g).

$R_f$ 0.60 ($CH_2Cl_2$, MeOH (95:5))

(b) (R)-$N^5$-(Cbz)-(R,S)-N-[1-(4-Phenoxyphenyl)ethyl]ornithine amide hydrochloride Prepared according to the method described in Example 1(b) above from (R)-$N^2$-(Boc)-$N^5$-(Cbz)-(R,S)-N-[1-(4-phenoxyphenyl)ethyl]ornithine amide (2.6 g; from step (a) above), EtOAc (100 mL) and HCl/EtOAc (50 mL), 22 hours reaction time. The resulting solution was concentrated to afford the crude sub-title compound as a crushable foam (2.4 g) which was used directly in the next step.

$R_f$ 0.30 and 0.40 (CHCl$_3$:MeOH:AcOH (9:1:0.1))

$^1$H NMR (CD$_3$OD) δ1.42–1.54 (m, 4H), 1.63 (m, 1H), 1.75–1.96 (m, 2H), 3.10 (t, 1H), 3.20 (t, 1H), 3.87 (m, 1H), 4.87–5.12 (m, 3H), 6.92–6.98 (m, 4H), 7.10 (m, 1H), 7.22–7.38 (m, 9H)

(c) (R)-N$^5$-(Cbz)-N$^2$-(Diphenylacetyl)-(R,S)-N-[1-(4-phenoxyphenyl)-ethyl]ornithine amide Prepared according to the method described in Example 1(d) above from (R)-N$^5$-(Cbz)-(R,S)-N-[1-(4-phenoxyphenyl)ethyl]ornithine amide hydrochloride (2.4 g; 4.82 mmol; step (b) above), 2-nitrophenyl diphenyl acetate (1.5 g; 4.82 mmol; see Example 1(c) above), TEA (0.7 g, 7.23 mmol) and CH$_2$Cl$_2$ (250 mL), 18 hours reaction time. The resultant yellow solution was concentrated and chromatographed on silica eluting with CH$_2$Cl$_2$:EtOAc (5:1 then 3:1) to afford the sub-title compound as a solid (2.4 g).

$R_f$ 0.50 (CH$_2$Cl$_2$:EtOAc (3:1))

$^1$H NMR (CDCl$_3$) δ1.12–1.63 (m, 6H), 1.78 (m, 1H), 3.07 (m, 1H), 3.31 (m, 1H), 4.65 (m, 1H), 4.78–5.13 (m, 4H), 6.67 (t, 1H), 6.82–7.43 (m, 24H)

(d) (R)-N$^2$-(Diphenylacetyl)-(R,S)-N-[1-(4-phenoxyphenyl)ethyl]ornithine amide hydrochloride Prepared according to the method described in Example 1(e) above from (R)-N$^5$-(Cbz)-N$^2$-(diphenyl acetyl)-(R,S)-N-[1-(4-phenoxyphenyl)ethyl]-ornithine amide (2.4 g; from step (c) above), concentrated HCl (2 mL), MeOH (200 mL) and 10% Pd/C (w/w, 0.5 g) under 1 atmosphere of hydrogen, 4 hours reaction time. The resulting solution was filtered and concentrated to afford the crude sub-title compound as a crushable foam (2.1 g) which was used directly in the next step.

mp 190–195° C.

$R_f$ 0.50 (System C)

$^1$H NMR (CD$_3$OD) δ1.35–1.45 (m, 3H), 1.54–1.95 (m, 4H), 2.82–2.97 (m, 2H), 4.44 (m, 1H), 4.93 (m, 1H), 5.08 and 5.15 (s, 1H), 6.78–6.98 (m, 4H), 7.02–7.41 (m, 15H)

(e) (R)-N$^2$-(Diphenylacetyl)-(R,S)-N-[1-(4-phenoxyphenyl) ethyl]arginine amide hydrochloride Prepared according to the method described in Example 6(e) above from (R)-N$^2$-(diphenylacetyl)-(R,S)-N-[1-(4-phenoxyphenyl)ethyl]ornithine amide hydrochloride (0.50 g; 0.90 mmol; from step (d) above), 1H-pyrazole-1-carboxamidine monohydrochloride (0.13 g; 0.90 mmol), TEA (0.36 g; 3.60 mmol) and DMF (7 mL), 18 hours reaction time. The resulting heterogeneous solution was concentrated and chromatographed on silica eluting with MeOH, CHCl$_3$, and concentrated NH$_4$OH (3:6:1) and converted to the hydrochloride salt to afford the title compound as a white solid (0.35 g).

mp 87–95° C.

$R_f$ 0.50 (System D)

$^1$H NMR (CD$_3$OD) δ1.41 (d, 3H), 1.47–1.90 (m, 4H), 3.08–3.19 (m, 2H), 4.42 (m, 1H), 4.94 (m, 1H), 5.10 and 5.17 (s, 1H), 6.82–6.98 (m, 4H), 7.04–7.38 (m, 15H)

Example 27

(R)-N$^2$-(Diphenylacetyl)-(R,S)-N-[1-(4-phenylphenyl)ethyl]arginine amide hydrochloride (a) (R)-N$^2$-(Boc)-N$^5$-(Cbz)-(R,S)-N-[1-(4-Phenylphenyl)ethyl]ornithine amide Prepared according to the method described in Example 4(b) above from N$^α$-Boc-N$^δ$-Cbz-(R)-ornithine-o-nitrophenyl ester (3.0 g; 6.15 mmol), (R,S)-4-phenyl-a-methylbenzylamine (1.3 g; 6.77 mmol) and CH$_2$Cl$_2$ (150 mL), 18 hours reaction time. The resultant yellow solution was concentrated and chromatographed on silica eluting with CH$_2$Cl$_2$:MeOH (95:5) to afford the sub-title compound as a crushable foam (3.4 g).

$R_f$ 0.50 (CH$_2$Cl$_2$, MeOH (95:5))

(b) (R)-N$^5$-(Cbz)-(R,S)-N-[1-(4-Phenylphenyl)ethyl] ornithine amide hydrochloride Prepared according to the method described in Example 1(b) above from (R)-N$^2$-(Boc)-N$^5$-(Cbz)-(R,S)-N-[1-(4-phenylphenyl)ethyl]ornithine amide (3.4 g; from step (a) above), EtOAc (100 mL) and HCl/EtOAc (75 mL), 18 hours reaction time. The resultant solution was concentrated to afford the crude sub-title compound as a crushable foam (3.2 g) which was used directly in the next step.

$R_f$ 0.30 and 0.40 (CHCl$_3$:MeOH:AcOH (9:1:0.1))

$^1$H NMR (CH$_3$OD) δ1.43–1.57 (m, 4H), 1.65 (m, 1H), 1.77–1.98 (m, 2H), 3.11 (m, 1H), 3.20 (t, 1H), 3.88 (m, 1H), 4.99 (s, 1H), 5.03–5.14 (m, 2H), 7.23–7.48 (m, 10H), 7.54–7.62 (m, 4H)

(c) (R)-N$^5$-(Cbz)-N$^2$-(Diphenylacetyl)-(R,S)-N-[1-(4-phenylphenyl)ethyl]-ornithine amide Prepared according to the method described in Example 1(d) above from (R)-N$^5$-(Cbz)-(R,S)-N-[1-(4-phenylphenyl) ethyl]ornithine amide hydrochloride (3.2 g; 6.53 mmol; from step (b) above), 2-nitrophenyl diphenyl acetate (2.1 g; 6.53 mmol; see Example 1(c) above), TEA (1.7 g; 16.33 mmol) and CH$_2$Cl$_2$ (250 mL), 60 hours reaction time. The resultant yellow solution was concentrated to give a solid. Digestion of the crude solids with hot CH$_2$Cl$_2$, EtOAc and MeOH afforded the sub-title compound as a solid (1.2 g). Additional material was available by concentration of the resultant filtrate followed by chromatography on silica eluting with CH$_2$Cl$_2$:EtOAc (5:1 then 3:1) to afford additional sub-title compound as a solid (2.3 g).

$R_f$ 0.50 (CH$_2$Cl$_2$, EtOAc (3:1))

$^1$H NMR (CDCl$_3$) δ1.33–1.68 (m, 6H), 1.78 (m, 1H), 3.02–3.23 (m, 2H), 4.48 (m, 1H), 4.93–5.11 (m, 4H), 7.18–7.49 (m, 24H)

(d) (R)-N$^2$-(Diphenylacetyl)-(R,S)-N-[1-(4-phenylphenyl) ethyl]ornithine amide hydrochloride Prepared according to the method described in Example 1(e) above from (R)-N$^5$-(Cbz)-N$^2$-(diphenylacetyl)-(R,S)-N-[1-(4-phenylphenyl) ethyl]-ornithine amide (1.2 g; from step (c) above), concentrated HCl (1 mL), MeOH (100 mL) and 10% Pd/C (w/w; 0.3 g) under 1 atmosphere of hydrogen, 18 hours reaction time. The resultant solution was filtered and concentrated to afford the crude sub-title compound as a crushable foam (1.0 g) which was used directly in the next step.

mp 205–210° C.

$R_f$ 0.50 (System C)

$^1$H NMR (CH$_3$OD) δ1.44 (d, 3H), 1.58–1.97 (m, 4H), 2.84–2.98 (m, 2H), 4.48 (m, 1H), 4.98 (m, 1H), 5.13 and 5.19 (s, 1H), 7.12–7.61 (m, 19H)

(e) (R)-N$^2$-(Diphenylacetyl)-(R,S)-N-[1-(4-phenylphenyl) ethyl]arginine amide hydrochloride Prepared according to the method described in Example 6(e) above from (R)-N$^2$-(diphenylacetyl)-(R,S)-N-[1-(4-phenylphenyl)ethyl]ornithine amide hydrochloride (0.50 g; 0.92 mmol; from step (d) above), 1H-pyrazole-1-carboxamidine monohydrochloride (0.13 g; 0.92 mmol), TEA (0.37 g; 3.68 mmol) and DMF (7 mL), 18 hours reaction time. The resulting heterogeneous solution was concentrated and chromatographed on silica eluting with MeOH:CHCl$_3$: conc. NH$_4$OH (3:6:1) and converted to the hydrochloride salt to afford the title compound as a white solid (0.22 g).

mp 100–105° C.
R$_f$ 0.50 (System D)
$^1$H NMR (CH$_3$OD) δ1.45 (d, 3H), 1.46–1.93 (m, 4H), 3.04–3.20 (m, 2H), 4.45 (m, 1H), 4.98 (m, 1H), 5.09 and 5.14 (s, 1H), 7.12–7.61 (m, 19H)

Example 28

(R)-N$^2$-(Diphenylacetyl)-(R,S)-N-[1-(2-naphthyl) ethyl]arginine amide hydrochloride (a) (R)-N$^2$-(Boc)-N$^5$-(Cbz)-(R,S)-N-[1-(2-naphthyl)ethyl] ornithine amide Prepared according to the method described in Example 4(b) above from N$^α$-Boc-N$^δ$-Cbz-(R)-ornithine-o-nitrophenyl ester (3.0 g; 6.15 mmol; see Example 4(a) above), (R,S)-1-(2-naphthyl)ethylamine (1.2 g; 6.77 mmol) and CH$_2$Cl$_2$ (150 mL), 18 hours reaction time. The resultant yellow solution was concentrated and chromatographed on silica eluting with CH$_2$Cl$_2$:MeOH (95:5) to afford the sub-title compound as an oil (4.1 g).

R$_f$ 0.40 (CH$_2$Cl$_2$:MeOH (95:5))

(b) (R)-N$^5$-(Cbz)-(R,S)-N-[1 -(2-Naphthyl)ethyl]ornithine amide hydrochloride

Prepared according to the method described in Example 1(b) above from (R)-N$^2$-(Boc)-N$^5$-(Cbz)-(R,S)-N-[1-(2-naphthyl)ethyl]ornithine amide (4.1 g; from step (a) above), EtOAc (100 mL) and HCl/EtOAc (75 mL), 18 hours reaction time. The resultant solution was concentrated to afford the crude sub-title compound as a crushable foam (3.6 g) which was used directly in the next step.

R$_f$ 0.30 and 0.40 (CHCl$_3$:MeOH:AcOH (9:1:0.1))

(c) (R)-N$^5$-(Cbz)-N$^2$-(Diphenylacetyl)-(R,S)-N-[1-(2-naphthyl)ethyl]-ornithine amide Prepared according to the method described in Example 1(d) above from crude (R)-N$^5$-(Cbz)-(R,S)-N-[1-(2-naphthyl)ethyl]ornithine amide hydrochloride (3.6 g; 7.81 mmol; from step (b) above), 2-nitrophenyl diphenyl acetate (2.5 g; 7.81 mmol; see Example 1(c) above), TEA (2.0 g, 19.53 mmol) and CH$_2$Cl$_2$ (250 mL), 60 hours reaction time. The resultant yellow solution was concentrated and chromatographed on silica eluting with CH$_2$Cl$_2$ and EtOAc (5:1 then 3:1) to afford the sub-title compound as a solid (3.8 g).

R$_f$ 0.50 (CH$_2$Cl$_2$:EtOAc (3:1))

$^1$H NMR (CDCl$_3$) δ1.32–1.92 (m, 4H), 1.49 (d, 3H), 3.06 (m, 1H), 3.38 (m, 1H), 4.62–5.22 (m, 5H), 6.59 (m, 1H), 7.04–7.37 (m, 16H), 7.38–7.49 (m, 2H), 7.54–7.83 (m, 4H)

(d) (R)-N$^2$-(Diphenylacetyl)-(R,S)-N-[1-(2-naphthyl)ethyl] ornithine amide hydrochloride Prepared according to the method described in Example 1(e) above from (R)-N$^5$-(Cbz)-N$^2$-(diphenylacetyl)-(R,S)-N-[1-(2-naphthyl)ethyl]ornithine amide (3.8 g; from step (c) above), concentrated HCl (2 mL), MeOH (200 mL) and 10% Pd/C (w/w; 0.8 g) under 1 atmosphere of hydrogen, 18 hours reaction time. The resultant solution was filtered and concentrated to afford the crude sub-title compound as a crushable foam (3.3 g), which was used without further purification.

mp 65–75° C.
R$_f$ 0.50 (System C)
$^1$H NMR (CH$_3$OD) δ1.47–1.53 (m, 3H), 1.54–1.96 (m, 4H), 2.82–2.97 (m, 2H), 4.48 (m, 1H), 5.03–5.18 (m, 2H), 7.08–7.49 (m, 13H), 7.68–7.85 (m, 4H)

(e) (R)-N$^2$-(Diphenylacetyl)-(R,S)-N-[1-(2-naphthyl)ethyl] arginine amide hydrochloride Prepared according to the method described in Example 6(e) above from (R)-N$^2$-(diphenylacetyl)-(R,S)-N-[1-(2-naphthyl)ethyl]ornithine amide hydrochloride (0.50 g; 0.97 mmol; from step (d) above), 1H-pyrazole-1-carboxamidine monohydrochloride (0.14 g, 0.97 mmol), TEA (0.39 g; 3.88 mmol) and DMF (7 mL), 18 hours reaction time. The resulting heterogeneous solution was concentrated and chromatographed on silica eluting with MeOH:CHCl$_3$: conc. NH$_4$OH (3:6:1) and converted to the hydrochloride salt to afford the title compound as a white solid (0.31 g).

mp 85–95° C.
R$_f$ 0.50 (System D)
$^1$H NMR (CH$_3$OD) δ1.32–1.93 (m, 7H), 2.98–3.17 (m, 2H), 4.43 (m, 1H), 5.04–5.18 (m, 2H), 7.07–7.49 (m, 13H), 7.68–7.84 (m, 4H)

Example 29

(R)-N$^2$-(Diphenylacetyl)-(R)-N-[1-( 1-naphthyl) ethyl]arginine amide hydrochloride (a) (R)-N$^2$-(Boc)-N$^5$-(Cbz)-(R)-N-[1-(1-Naphthyl)ethyl] ornithine amide Prepared according to the method described in Example 4(b) above from N$^α$-Boc-N$^δ$-Cbz-(R)-ornithine-o-nitrophenyl ester (5.2 g; 10.6 mmol; see Example 4(a) above), (R)-1-(1-naphthyl)ethylamine hydrochloride (2.0 g; 11.7 mmol), and CH$_2$Cl$_2$ (150 mL), 48 hours reaction time. The resultant yellow solution was concentrated to afford the crude sub-title compound as a solid (7.5 g) which was used directly in the next step.

R$_f$ 0.40 (CH$_2$Cl$_2$:MeOH (95:5))

(b) (R)-N$^5$-(Cbz)-(R)-N-[1-(1-Naphthyl)ethyl]ornithine amide hydrochloride

Prepared according to the method described in Example 1(b) above from crude (R)-N$^2$-(Boc)-N$^5$-(Cbz)-(R)-N-[1-(1-naphthyl)ethyl]ornithine amide (7.5 g; from step (a) above), EtOAc (150 mL) and HCl/EtOAc (75 mL), 6 hours reaction time. The resulting heterogeneous solution was diluted with Et$_2$O and the solids collected and dried to afford the sub-title compound as a white solid (4.8 g).

R$_f$ 0.40 (CHCl$_3$:MeOH:AcOH (9:1:0.1))

$^1$H NMR (CH$_3$OD) δ1.36–1.52 (m, 2H), 1.58–1.90 (m, 5H), 2.92–3.10 (m, 2H), 3.91 (m, 1H), 4.74–5.02 (m, 3H), 5.88 (m, 1H), 7.18–7.37 (m, 4H), 7.38–7.61 (m, 5H), 7.76 (d, 1H), 7.87 (d, 1H), 8.08 (d, 1H)

(c) (R)-N$^5$-(Cbz)-N$^2$-(Diphenylacetyl)-(R)-N-[1-(1-naphthyl)ethyl]-ornithine amide Prepared according to the method described in Example 1(d) above from (R)-N$^5$-(Cbz)-(R)-N-[1-(1-naphthyl)ethyl] ornithine amide hydrochloride (4.8 g; 10.46 mmol; from step (b) above), 2-nitrophenyl diphenyl acetate (3.4 g; 10.46 mmol; see Example 1(c) above), TEA (2.7 g; 26.15 mmol) and CH$_2$Cl$_2$ (200 mL), 60 hours reaction time. The resultant heterogeneous solution was filtered. The filter cake was washed with Et$_2$O and dried to afford the sub-title compound as a white solid (3.4 g).

R$_f$ 0.70 (CH$_2$Cl$_2$:EtOAc (3:1))

$^1$H NMR (CDCl$_3$) δ1.22–1.78 (m, 7H), 2.96 (m, 1H), 3.32 (m, 1H), 4.52–4.97 (m, 4H), 5.82 (m, 1H), 6.59 (d, 1H), 7.03 (d, 1H), 7.08–7.52 (m, 19H), 7.69 (d, 1H), 7.80 (d, 1H), 7.98 (d, 1H)

(d) (R)-N$^2$-(Diphenylacetyl)-(R)-N-[1-(1-naphthyl)ethyl] ornithine amide

Prepared according to the method described in Example 6(d) above from (R)-N$^5$-(Cbz)-N$^2$-(diphenylacetyl)-(R)-N-[1-(1-naphthyl)ethyl]ornithine amide (1.0 g; 1.63 mmol; from step (c) above), trimethylsilyliodide (0.36 g, 1.79 mmol) and CH$_3$CN (60 mL) at 0° C., 3.5 hours reaction time. The resultant heterogeneous solution was submitted to aqueous work up and chromatographed on silica eluting with CH$_2$Cl$_2$:MeOH:conc. NH$_4$OH (88.5:10:1.5) to afford the sub-title compound as a solid (0.5 g).

$R_f$ 0.50 (System C)

¹H NMR (CH₃OD) δ1.25–1.43 (m, 2H), 1.52–1.81 (m, 2H), 1.58 (d, 3H), 2.47 (t, 2H), 4.42 (m, 1H), 5.08 (s, 1H), 5.78 (q, 1H), 7.17–7.33 (m, 10H), 7.40–7.54 (m, 4H), 7.78 (d, 1H), 7.88 (d, 1H), 8.06 (d, 1H)

(e) (R)-N²-(Diphenylacetyl)-(R)-N-[1-(1-naphthyl)ethyl]arginine amide hydrochloride Prepared according to the method described in Example 6(e) above from (R)-N²-(diphenylacetyl)-(R)-N-[1-(1-naphthyl)ethyl]ornithine amide (0.42 g; 0.88 mmol; step (d) above), 1H-pyrazole-1-carboxamidine mono-hydrochloride (0.14 g; 0.88 mmol), TEA (0.18 g; 1.76 mmol) and DMF (8 mL), 18 hours reaction time. The resultant solution was concentrated and chromatographed on silica eluting with MeOH:CHCl₃:conc. NH₄OH (3:6:1) to afford the title compound as a white solid (0.38 g).

mp 128–135° C.

$R_f$ 0.50 (System D)

¹H NMR (CH₃OD) δ1.37–1.85 (m, 4H), 1.58 (d, 3H), 2.94–3.14 (m, 2H), 4.43 (t, 1H), 5.11 (s, 1H), 5.81 (q, 1H), 7.15–7.33 (m, 10H), 7.38–7.56 (m, 4H), 7.78 (d,1H), 7.88 (d, 1H), 8.06 (d, 1H)

Example 30

(R)-N²-[(R,S)-2-(4-Methoxyphenyl)phenylacetyl-(R) -N-[1-(4-hydroxy-phenyl)ethyl]arginine amide acetate (a) (R)-N²-(Boc)-(R)-N-[1-(4-hydroxyphenyl)ethyl] ornithine amide To a solution of (R)-N²-(Boc)-N⁵-(Cbz)-(R)-N-[1-(4-hydroxyphenyl)-ethyl]ornithine amide (66.26 g; 139 mmol; see Example 4(b) above) in methanol (400 mL) was added 10% Pd/C (w/w; 3.53 g). After stirring for 18 h under 1 atmosphere of hydrogen the reaction was filtered through Celite to remove the catalyst and the filtrate was concentrated under reduced pressure to afford the sub-title compound as a white foam (43.2 g, 123 mmol).

$R_f$ 0.2 (System B)

(b) (R)-N^ω,N^ω'-bis(Cbz)-N²-(Boc)-(R)-N-[1-(4-Hydroxyphenyl)ethyl]-arginine amide To a solution of (R)-N²-(Boc)-(R)-N-[1-(4-hydroxyphenyl)ethyl]ornithine amide (11.47 g; 0.33 mmol; from step (a) above) in DMF (50 mL) was added N,N'-bis(Cbz)-S-methylisothiourea (11.8 g; 0.33 mmol). The solution was stirred overnight at room temperature followed by removal of the solvent under reduced pressure. The resultant oil was chromatographed on a plug of silica gel (7.5 cm×12.5 cm) eluting first with CH₂Cl₂ (800 mL) to remove the higher $R_f$ impurities. The eluent was switched to EtOAc (600 mL) to elute the sub-title compound as a white foam (14.67 g).

$R_f$ 0.45 (EtOAc:hexanes (1:1))

(c) (R)-N^ω,N^ω'-bis(Cbz)-(R)-N-[1-(4-Hydroxyphenyl) ethyl]arginine amide hydrochloride A solution of (R)-N^ω,N^ω'-bis(Cbz)-N²-(Boc)-(R)-N-[1-(4-hydroxyphenyl)-ethyl]arginine amide (11.2 g; 16.4 mmol, from step (b) above) in EtOAc (300 mL) was treated with HCl/EtOAc (300 mL) and stirred overnight at room temperature. The product precipitated as a white residue from which the solvents were decanted. To the residue was added methanol (100 mL) followed by diethyl ether (50 mL). This mixture was slurried and then concentrated at reduced pressure to afford the sub-title compound as a white crushable foam (10.2 g; 100%).

$R_f$ 0.89 (EtOAc, CH₃OH, conc. NH₄OH (47:47:6))

(d) (R)-N^ω,N^ω'-bis(Cbz)-N²-[(R,S)-2-(4-Methoxyphenyl) phenylacetyl]-(R)-N-[1-(4-hydroxyphenyl)ethyl]arginine amide (R)-N^ω,N^ω'-bis(Cbz)-(R)-N-[1-(4-Hydroxyphenyl)ethyl] arginine amide x hydrochloride (0.5 g; 0.848 mmol; from step (c) above) was treated with (R,S)-2-(4-methoxyphenyl)-phenylacetylchloride (0.933 mmol; 1.1 eq.) in EtOAc (25 mL) and saturated bicarbonate solution (25 mL). The reaction was stirred for 1.5 h at room temperature. The organic layer was separated and washed with KHSO₄ solution (25 mL) and brine (50 mL). The organics were then dried with Na₂SO₄ and concentrated to afford the sub-title compound as a white foam (650 mg).

$R_f$ 0.65 (EtOAc:hexanes (1:1))

(e) (R)-N²-[(R,S)-2-(4-Methoxyphenyl)phenylacetyl]-(R)-N-[1-(4-hydroxyphenyl)ethyl]arginine amide acetate To a solution of (R)-N^ω,N^ω'-bis(Cbz)-N²-[(R,S)-2-(4-methoxyphenyl) -phenylacetyl]-(R)-N-[1-(4-hydroxyphenyl)ethyl]arginine amide (700 mg; 0.99 mmol; from step (d) above) in AcOH (50 mL) was added 10% Pd/C (w/w; 100 mg). The reaction was stirred for 18 h under 1 atmosphere of hydrogen, and then filtered through Celite to remove the catalyst. The filtrate was concentrated under vacuum. The title compound was isolated as an off white solid (560 mg, 0.97 mmol) after milling in EtOAc:Et₂O (100 mL; 3:1).

$R_f$ 0.52 (EtOAc:CH₃OH:conc. NH₄OH (47:47:6))

mp 136–142° C.

¹H NMR (CH₃OD) δ1.38 (d, 3H), 1.41–1.89 (m, 4H), 1.90 (s, 3H), 3.09 (m, 2H), 3.80 (s, 3H), 4.39 (m, 1H), 4.87 (m, 1H), 5.05 (s, 1H), 6.69 (d, 2H), 6.82 (m, 2H), 7.15 (m, 2H), 7.18–7.37 (m, 7H)

Example 31

(R)-N² -(R,S)-2-(4-Methylphenyl)phenylacetyl]-(R)-N-[1-(4-hydroxy-phenyl)ethyl]arginine amide acetate (a) (R)-N⁵-(Cbz)-N²-[(R,S)-2-(4-Methylphenyl) phenylacetyl]-(R)-N-[1-(4-hydroxyphenyl)ethyl]ornithine amide A biphasic solution of (R)-N⁵-(Cbz)-(R)-N-[1-(4-hydroxyphenyl)ethyl]-ornithine amide hydrochloride (371 mg ; 0.880 mmol; from Example 1(b) above) in EtOAc (10 mL) and saturated bicarbonate solution (10 mL) was treated with (R,S)-2-(4-methylphenyl)phenylacetyl chloride (0.880 mmol; 1.0 eq.) and stirred for 2 h at room temperature. The organics were then separated and washed with KHSO₄ solution and brine. The organic layer was dried with Na₂SO₄ and concentrated. The residue was crystallized from hot ethyl acetate to give the sub-title compound as a white solid (163 mg).

$R_f$ 0.48 (EtOAc:hexanes (1:1))

¹H NMR (CH₃OD) δ1.33 (d, 3H), 1.41–1.81 (m, 4H), 2.25 (s, 3H), 3.01 (m, 2H), 4.40 (m, 1H), 4.87 (m, 1H), 5.05 (s, 1H), 6.71 (d, 2H), 6.9–7.37 (m, 12H)

(b) (R)-N²-[(R,S)-2-(4-Methylphenyl)phenylacetyl]-(R)-N-[1-(4-hydroxy-phenyl)ethyl]ornithine amide hydrochloride Prepared in a similar fashion to Example 1(e) above. To a solution of (R)-N⁵-(Cbz)-N²-[(R,S)-2-(4-methylphenyl) phenylacetyl]-(R)-N-[1-(4-hydroxyphenyl)ethyl]ornithine amide (160 mg; 0.262 mmol; from step (a) above) in methanol (100 mL) was added 2N HCl (5 mL) and 10% Pd/C (w/w, 100 mg). The reaction was stirred under 1 atmosphere of hydrogen for 18 h. The reaction mixture was filtered through Celite and the filtrate concentrated to afford the sub-title compound as a white foam (120 mg; 0.262 mmol).

$R_f$ 0.20 (System B)

(c) (R)-N$^\omega$,N$^{\omega'}$-bis(Cbz)-N$^2$-[(R,S)-2-(4-Methylphenyl)phenylacetyl]-(R)-N-[-1-(4-hydroxyphenyl)ethyl]arginine amide Prepared in a similar fashion to Example 1(f) above. A solution of (R)-N$^2$-[(R,S)-2-(4-methylphenyl)phenylacetyl]-(R)-N-[1-(4-hydroxyphenyl)-ethyl]ornithine amide hydrochloride (120 mg; 0.262 mmol; from step (b) above) in DMF (15 mL) was treated with N,N'-bis(Cbz)-S-methylisothiourea (0.120 g; 0.335 mmol) and DiPEA (2 mL). The reaction was stirred for 18 h at room temperature. The solvents were removed at reduced pressure and the resulting residue was chromatographed on silica gel. Eluting first with CH$_2$Cl$_2$ and then EtOAc afforded the sub-title compound as a white foam (160 mg).

$R_f$ 0.65 (EtOAc:hexanes (1:1))

(d) (R)-N$^2$-[(R,S)-2-(4-Methylphenyl)phenylacetyl]-(R)-N-[1-(4-hydroxy-phenyl)ethyl]arginine amide acetate To a solution of (R)-N$^\omega$,N$^{\omega'}$-bis(Cbz)-N$^2$-[(R,S)-2-(4-methylphenyl) -phenylacetyl]-(R)-N-[1-(4-hydroxyphenyl) ethyl]arginine amide (122 mg; 0.183 mmol; from step (c) above) in AcOH (50 mL) was added 10% Pd/C (w/w; 100 mg). The reaction was stirred for 18 h under 1 atmosphere of hydrogen, the reaction mixture was filtered through-Celite and the filtrate concentrated to afford the title compound as a white foam (101 mg).

$R_f$ 0.50 (EtOAc:CH$_3$OH:conc. NH$_4$OH (47:47:6))

mp 110–116° C.

$^1$H NMR (CH$_3$OD) δ1.33 (d, 3H), 1.41–1.89 (m, 4H), 1.90 (s, 3H), 2.26 (s, 3H), 3.09 (m, 2H), 4.38 (m, 1H), 4.87 (m, 1H), 5.02 (s, 1H), 6.69 (d, 2 H), 6.9–7.37 (m, 11H)

Example 32

(R)-N$^2$ -[(R,S)-2-(4-Chlorophenyl)phenylacetyl]-(R)-N-[1-(4-hydroxy-phenyl)ethyl]arginine amide hydrochloride (a) (R)-N$^\omega$,N$^{\omega'}$-bis(Cbz)-N$^2$-[(R,S)-2-(4-Chlorophenyl)phenylacetyl]-(R)-N-[1-(4-hydroxyphenyl)ethyl]arginine amide (R)-N$^\omega$, N$^{\omega'}$-bis(Cbz)-(R)-N-[1-(4-Hydroxyphenyl)ethyl] arginine amide x hydrochloride (0.5 g; 0.848 mmol; see Example 30(c) above) was treated with (R,S)-2-(4-chlorophenyl)phenylacetylchloride (1.27 mmol; 1.5 eq.) in ethyl acetate (25 mL) and saturated bicarbonate solution (25 mL). The reaction was stirred for 1.5 h at room temperature. The organic layer was separated and washed with KHSO$_4$ (25 mL) and brine (50 mL). The organics were then dried with Na$_2$SO$_4$ and concentrated to afford the sub-title compound as a white foam (674 mg; 100%).

$R_f$ 0.80 (System B)

(b) (R)-N$^2$-[(R,S)-2-(4-Chlorophenyl)phenylacetyl]-(R)-N-[1-(4-hydroxyphenyl)ethyl]arginine amide hydrochloride To a solution of(R)-N$^\omega$,N$^{\omega'}$-bis(Cbz)-N$^2$-[(R,S)-2-(4-Chlorophenyl)phenyl-acetyl]-(R)-N-[1-(4-hydroxyphenyl) ethyl]arginine amide (670 mg; 0.84 mmol; from step (a) above) in CH$_3$OH (50 mL) was added 2N HCl (1.0 mL) and 10% Pd/C (w/w; 100 mg). The reaction was stirred for 18 h under 1 atmosphere of hydrogen, and then filtered through Celite to remove the catalyst and the filtrate was concentrated under vacuum. The title compound was isolated as a off white solid (400 mg, 0.72 mmol) after lo milling in EtOAc:Et$_2$O (100 mL; 3:1).

$R_f$ 0.51 (EtOAc, CH$_3$OH, conc. NH$_4$OH (47:47:6)

mp 120–125° C.

$^1$H NMR (CD$_3$OD) δ 1.33 (d, 3H), 1.41–1.89 (m, 4H), 3.08 (m, 2H), 4.39 (m, 1H), 4.90 (m, 1H), 5.08 (s, 1H), 6.70 (d, 2H), 7.05 (d, 2H), 7.1–7.4 (m, 9H)

Example 33

(R)-N$^2$-(4,4 1'-Dichlorodiphenylacetyl)-(R)-N-[1-(4-hydroxyphenyl)ethyl]-arginine amide hydrochloride (a) (R)-N$^\omega$,N$^{\omega'}$-bis(Cbz)-N$^2$-(4,4'-Dichlorodiphenylacetyl)-(R)-N-[1-(4-hydroxyphenyl)ethyl]arginine amide To a biphasic solution of(R)-N$^\omega$,N$^{\omega'}$-bis(Cbz)-(R)-N-[1-(4-hydroxyphenyl)ethyl]arginine amide hydrochloride (1.26 g; 2.1 mmol; from Example 30(c) above) in EtOAc and saturated NaHCO$_3$ solution was added 4,4'-dichlorodiphenylacetyl chloride. The reaction mixture was stirred for 3.5 h at room temperature. The organics were separated, washed with KHSO$_4$ solution (100 mL) and brine (150 mL), dried with Na$_2$SO$_4$, filtered and concentrated to afford the sub-title compound as a white foam (920 mg; 1.15 mmol).

$R_f$ 0.80 (System B)

(b) (R)-N$^2$-(4,4'-Dichlorodiphenylacetyl)-(R)-N-[1-(4-hydroxyphenyl)ethyl]arginine amide hydrochloride To a solution of (R)-N$^\omega$,N$^{\omega'}$-bis(Cbz)-N$^2$-(4,4'-dichlorodiphenylacetyl)-(R)-N-[1-(4-hydroxyphenyl)ethyl] arginine amide (800 mg; 1.00 mmol; from step (a) above) in CH$_3$OH (40 mL) was added 2N HCl (1 mL) and 10% Pd/C (w/w; 100 mg). The reaction was stirred for 18 h under 1 atmosphere of hydrogen. The reaction was filtered through Celite and the filtrate concentrated to afford the title compound as an off white solid (436 mg; 0.735 mmol) after milling in EtOAc:Et$_2$O (100 mL; 3:1).

$R_f$ 0.22 (EtOAc:CH$_3$OH:conc. NH$_4$OH (47:47:6))

mp 141–146° C.

$^1$H NMR (CH$_3$OD) δ 1.32 (d, 3H), 1.41–1.89 (m, 4H), 3.08 (m, 2H), 4.35 (m, 1H), 4.90 (m, 1H), 5.11 (s, 1H), 6.71 (d, 2H), 7.1 (d, 2H), 7.15–7.4 (m, 8H).

Example 34

(R)-N$^2$-[(R,S)-2-(4-Hydroxyphenyl)phenylacetyl]-(R)-N-[1-(4-hydroxyphenyl)ethyl]arginine amide hydrochloride (a) N$^\omega$,N$^{\omega'}$-bis(Cbz)-N$^2$-[(R,S)-2-(4-Hydroxyphenyl)phenylacetyl]-(R)-N-[1-(4-hydroxyphenyl)ethyl]arginine amide To a solution of (R)-N$^\omega$,N$^{\omega'}$-bis(Cbz)-(R)-N-[1-(4-hydroxyphenyl)ethyl]arginine amide hydrochloride (0.821 g; 1.39 mmol; see Example 30(c) above) in THF (40 mL) was added (R,S)-2-(4-hydroxyphenyl)phenylacetic acid (0.188 g; 1.39 mmol), BOP (0.62 g; 1.39 mmol), HOBT (0.188 g; 1.39 mmol) and DiPEA (0.48 mL; 2.78 mmol). The reaction was stirred overnight at room temperature, followed by removal of the THF under vacuum. The residues were taken up in ethyl acetate (100 mL) and washed with KESO$_4$ solution (100 mL) and brine (150 mL). The organics ere dried with Na$_2$SO$_4$, filtered and concentrated to give the sub-title compound as a white foam (480 mg; 0.566 mmol).

$R_f$ 0.60 (EtOAc:hexanes (1:1))

b) (R)-N$^2$-[(R,S)-2-(4-hydroxyphenyl)phenylacetyl]-(R)-N-[1-(4-hydroxyphenyl)ethyl]arginine amide hydrochloride To a solution of (R)-N$^\omega$,N$^{\omega'}$-bis(Cbz)-N$^2$-[(R,S)-2-(4-hydroxyphenyl)phenylacetyl]-(R)-N-[1-(4-hydroxyphenyl) ethyl]arginine amide (480 mg; 0.566 mmol; from step (a) above) in methanol (50 mL) was added conc. HCl (5 drops) and 10% Pd/C (w/w; 40 mg). The reaction was stirred for 20 h under 1 atmosphere of hydrogen. The reaction mixture was then filtered through Celite and the filtrate concentrated to afford the title compound as an off white solid (305 mg; 0.565 mmol) after milling in EtOAc:Et$_2$O (70 mL; 3:1).

$R_f$ 0.35 (EtOAc:CH$_3$OH:conc. NH$_4$OH (6:3:1))

mp 129–136° C.

$^1$H NMR (CH$_3$OD) δ 1.34 (d, 3H), 1.41–1.85 (m, 4H), 3.08 (m, 2H), 4.38 (m, 1H), 4.85 (m, 1H), 5.11 (s, 1H), 6.71 (d, 2H), 7.05 (d, 2H), 7.15–7.4 (m, 9H)

Example 35

(R)-N$^ω$-(Ethyl)-N$^2$-(diphenylacetyl)-(R)-N-[1-(4-methoxyphenyl)ethyl]arginine amide hydrochloride (a) (R)-N$^5$-(Benzoylaminothiocarbonyl)-N$^2$-(diphenylacetyl)-(R)-N-[1-(4-methoxyphenyl)ethyl] ornithine amide To a solution of (R)-N$^2$-(diphenylacetyl)-(R)-N-[1-(4-hydroxyphenyl)ethyl]ornithine amide (2.0 g; 4.35 mmol; see Example 4(e) above) in CH$_2$Cl$_2$ (50 mL) was added benzoylisothiocyanate (0.59 mL; 4.35 mmol). The reaction mixture was stirred for 24 h at room temperature. The reaction was then concentrated in vacuo and the residue dissolved in EtOAc. The precipitated product, produced by addition of Et$_2$O to the EtOAc solution, was collected and dried to afford 2.25 g (83%) of the sub-title compound as a white solid. The resultant material was used without further characterization.

R$_f$=0.80 (System B)

(b) (R)-N$^5$-(Aminothiocarbonyl)-N$^2$-(diphenylacetyl)-(R)-N-[1-(4-methoxyphenyl)ethyl]ornithine amide (R)-N$^5$-(Benzoylaminothiocarbonyl)-N$^2$-(diphenylacetyl)-(R)-N-[1-(4-methoxyphenyl)ethyl] ornithine amide (2.25 g; 3.6 mmol; from step (a) above), methanol (250 mL), water (250 mL) and K$_2$CO$_3$ (1.49 g; 10.8 mmol) were combined and stirred for 24 h at room temperature. The reaction mixture was then partitioned between EtOAc (250 mL) and brine (250 mL). The EtOAc layer was separated and washed with brine, dried over Na$_2$SO$_4$ and concentrated in vacuo to afford 1.86 g (99%) of the sub-title compound as a white foam.

R$_f$ 0.55 (System B)

$^1$H NMR (CH$_3$OD) δ 1.38 (d, 3H), 1.47 (m, 2H), 1.52 (m, 1H), 1.77 (m, 1H), 3.4 (m, 2H), 3.76 (s, 3H), 4.42 (m, 1H), 4.90 (q, 1H), 5.07 (s, 1H), 6.85 (d, 2H), 7.18 (d, 2H), 7.19–7.4 (m, 10H)

(c) (R)-N$^5$-[Methylthio(iminomethyl)]-N$^2$-(diphenylacetyl)-(R)-N-[1-(4-methoxyphenyl)ethyl]ornithine amide hydroiodide A solution of (R)-N$^5$-(aminothiocarbonyl)-N$^2$-(diphenylacetyl)-(R)-N-[1-(4-methoxyphenyl)ethyl] ornithine amide (1.46g; 2.81 mmol; from step (b) above) and iodomethane (0.21 mL; 3.38 mmol) in CH$_2$Cl$_2$ (40 mL) and CH$_3$OH (40 mL) was stirred for 18 h at room temperature. The reaction was concentrated in vacuo and the residue was dissolved in a minimal amount of CH$_3$OH. To this solution was added EtOAc to initiate crystallization. 1.38 g (75%) of the sub-title compound was collected, which was used in the next step without further characterization.

R$_f$ 0.15 (System B)

(d) (R)-N$^5$-(Cbz)-N$^5$-[Methylthio(Cbz-iminomethyl)]-N$^2$-(diphenylacetyl)-(R)-N-[1-(4-methoxyphenyl)ethyl] ornithine amide (R)-N$^5$-[Methylthio(iminomethyl)]-N$^2$-(diphenylacetyl)-(R)-N-[1-(4-methoxyphenyl)ethyl]ornithine amide hydroiodide (1.38 g; 2.09 mmol; from step (c) above), CH$_2$Cl$_2$ (100 mL), Cbz-Cl (0.75 mL; 5.22 mmol), water (100 mL) and K$_2$CO$_3$ (1.16 g; 8.36 mmol) were combined and stirred for 18 h at room temperature. The organic layer was separated and washed with KHSO$_4$ solution (twice), NaHCO$_3$ solution (twice) and brine (twice), dried over Na$_2$SO$_4$ and concentrated in vacuo. The residue was chromatographed on silica column eluting with hexanes:EtOAc (3:1). Fractions containing the desired product were combined and concentrated in vacuo to afford 0.65 g (39%) of the sub-title compound. The material was used without farther characterization.

R$_f$ 0.85 (CH$_2$Cl$_2$:CH$_3$OH (9:1))

(e) (R)-N$^5$-(Cbz)-N$^5$-[Ethylamino(Cbz-iminomethyl)]-N$^2$-(diphenylacetyl)-(R)-N-[1-(4-methoxyphenyl)ethyl] ornithine amide A solution of (R)-N$^5$-(Cbz)-N$^5$-[methylthio(Cbz-iminomethyl)]-N$^2$-(diphenylacetyl)-(R)-N-[1-(4-methoxyphenyl)ethyl]ornithine amide(0.5g; 0.63 mmol; from step (d) above) and ethylamine (70% wt. in water; 0.08 mL; 0.94 mmol) in DMF (10 mL) was stirred for 1 h at room temperature. The DMF was removed in vacuo and the residue dissolved in EtOAc. The EtOAc solution was washed with KHSO$_4$ solution, then 0.5 N NaOH solution and then brine, dried over Na$_2$SO$_4$ and concentrated in vacuo to afford 0.33 g of the sub-title compound. The material was used directly in the next step.

(f) (R)-N$^ω$-(Ethyl)-N$^2$-(diphenylacetyl)-(R)-N-[1-(4-methoxyphenyl)ethyl]arginine amide hydrochloride To a solution of (R)-N$^5$-(Cbz)-N$^5$-[ethylamino(Cbz-imino)]-N$^2$-(diphenylacetyl)-(R)-N-[1 -(4-methoxyphenyl) ethyl]ornithine amide (0.21 g; 0.30 mmol; from step (e) above) in CH$_3$OH (30 mL) was added concentrated HCl (2 drops) and 10% Pd/C (w/w; 0.050 g). The reaction mixture was stirred for 18 h under 1 atmosphere of hydrogen at room temperature and filtered through celite. The filtrate was concentrated in vacuo to afford 0.15 g (90%) of the title compound.

R$_f$ 0.52 (EtOAc:CH$_3$OH:NH$_4$OH (47:47:6))

$^1$H NMR (CD$_3$OD) δ 5 1.17 (t, 3H), 1.38 (d, 2H), 1.50 (m, 2H), 1.59 (m, 1H), 1.80 (m, 1H), 3.11 (m, 2H), 3.17 (q, 2H), 3.75 (s, 3H), 4.40 (m, 1H 4.85 (q, 1H), 5.13 (s, 1H), 6.81 (d, 2H), 7.19 (d, 2H), 7.22–7.38 (m, 10H)

Example 36

(R)-N$^ω$-(Benzyl)-N$^2$-(diphenylacetyl)-(R)-N-[1-(4-methoxyphenyl)ethyl]arginine amide hydrochloride (a) (R)-N$^5$-(Cbz)-N$^5$-[Benzylamino(Cbz-iminomethyl)]-N$^2$-(diphenylacetyl)-(R)-N-[1-(4-methoxyphenyl)ethyl] ornithine amide A solution of (R)-N$^5$-(Cbz)-N$^5$-[methylthio(Cbz-iminomethyl)]-N$^2$-(diphenylacetyl)-(R)-N-[1-(4-methoxyphenyl)ethyl]ornithine amide (0.25 g, 0.312 mmol; see Example 35(d) above) and benzylamine (0.05 mL; 0.476 mmol) in DMF (5 mL) was stirred overnight at room temperature. The DMF was removed in vacuo and the residue dissolved in EtOAc. The EtOAc solution was washed with KHSO$_4$ solution, 0.5 N NaOH solution and brine, dried over Na$_2$SO$_4$ and concentrated in vacuo to afford 0.25 g of the sub-title compound. The material was used directly in the next step.

R$_f$ 0.74 (EtOAc:hexanes (1: 1))

$^1$H NMR (CH$_3$OD) δ 1.35 (d, 3H), 1.45–1.79 (m, 4H), 3.42 (m, 2H), 3.64 (m, 3H), 4.29 (s, 2H), 4.38 (m, 1H), 4.85 (m, 1H), 5.01 (s, 4H), 5.08 (s, 1H), 6.79 (d, 2H), 7.05 (d, 2H), 7.15–7.4 (m, 27H)

(b) (R)-N$^ω$-(Benzyl)-N$^2$-(diphenylacetyl)-(R)-N-[1-(4-methoxyphenyl)ethyl]arginine amide hydrochloride To a solution of (R)-N$^5$-(Cbz)-N$^5$-[benzylamino(Cbz-iminomethyl)]-N$^2$-(diphenylacetyl)-(R)-N-[1-(4-methoxyphenyl)ethyl]ornithine amide (0.248 g, 0.288 mmol; from step (a) above) in CH$_3$OH (50 mL) was added concentrated HCl (2 drops) and 10% Pd/C (w/w; 0.080 g). The reaction mixture was stirred overnight under 1 atmosphere of hydrogen at room temperature, filtered through Celite and the filtrate concentrated in vacuo to afford the title compound (0.168 g, 98%).

$R_f$ 0.23 (EtOAc:CH$_3$OH:conc. NH$_4$OH (47:47:6))

mp 126–130° C.

$^1$H NMR (CD$_3$OD) δ 1.32 (d, 3H), 1.41–1.89 (m, 4H), 3.11 (m, 2H), 3.71 (s, 3H), 4.31 (s, 2H), 4.35 (m, 1H), 4.90 (m, 1H), 5.10 (s, 1H), 6.81 (d, 2H), 7.15–7.4 (m, 17H)

Example 37

(R)-N$^ω$-(1-(4-hydroxyphenyl)ethyl)-N$^2$-(diphenylacetyl)-(R)-N-[1-(4-hydroxyphenyl)ethyl] arginine amide Hydrochloric acid (1 mL) and 10% Pd/C (w/w; 1.1 g) were added to a solution of (R)-N$^ω$,N$^{ω'}$-bis(Cbz)-N$^2$-(diphenylacetyl)-(R)-N-[1-(4-hydroxyphenyl)ethyl]arginine amide (6.6 g; 8.7 mmol; see Example 4(f) above) in methanol. The reaction was stirred for 18 h under one atmosphere of hydrogen, filtered through Celite and the fitrate concentrated to afford an off-white foam. The material was applied to a column of silica (5 cm×20 cm ht) and eluted with a mixture of CHCl$_3$:CH$_3$OH:conc. NH$_4$OH (6:3:1). Fractions (5 mL each) were taken and analyzed by HPLC. Fractions containing the title compound were combined and concentrated to afford a white foam (12 mg). The HPLC method used above was conducted on a Microsorb MV Cyano column (25 cm×4.6 mm) eluting with water:CH$_3$CN:TFA (65:35:0.1) at a flow rate of 1 mL/min. While monitoring the eluent at 254 nm. The title compound was found to have a retention time of 9.16 min.

$R_f$ 0.53 (System D)

mp 128–135° C.

FAB MS m/z =608

$^1$H NMR (CD$_3$OD) δ 1.35 (d, 3H), 1.45 (d, 3H), 1.51 (m, 2H), 1.60 (m, 1H), 1.72 (m, 1H), 3.10 (m, 2H), 4.38 (m, 1H), 4.62 (m, 1H), 4.90 (m, 1H), 5.12 (s, 1H), 6.71 (d, 2H), 6.78 (d, 2H), 7.08 (d, 2H), 7.12 (d, 2H), 7.2–7.4 (m, 18H)

Example 38

(R)-N$^2$-(Diphenylacetyl)-(R,S)-N-[1-(4-(aminocarbonylmethyl)phenyl)ethyl]arginine amide hydrochloride (a) (R)-N$^5$-(Cbz)-N$^2$-(diphenylacetyl)-ornithine 1 N NaOH (75 mL) was added to a stirred suspension of (R)-N$^5$-(Cbz)-ornithine hydrochloride (7.5 g; 25 mmol) in THF (114 mL). Once the starting material had dissolved, diphenylacetyl chloride (6.7 g; 26.3 mmol) was added. The reaction was stirred for 3 h at room temperature, then made acidic with cold 1 N HCl and extracted with EtOAc (3×75 mL). The EtOAc extract was washed with brine, dried with Na$_2$SO$_4$, and concentrated to afford the crude product. Purification by flash chromatography on silica eluting with EtOAc:hexanes (1:1) afforded the sub-title compound (10.5 g; 91%).

$R_f$ 0.22 (EtOAc:hexanes (1:1))

$^1$H NMR (CH$_3$OD) δ 1.53 (m, 2H), 1.71 (m, 1H), 1.79 (m, 1H), 3.09 (t, 2H), 4.40 (m, 1H), 5.05 (s, 2H), 5.09 (s, 1H), 7.12–7.45 (m, 15H).

(b) (R)-N$^5$-(Cbz)-N$^2$-(diphenylacetyl)-(R,S)-N-[1-(4-(aminocarbonylmethyl)phenyl)ethyl]ornithine amide (R,S)-1-[4-(Aminocarbonylmethyl)phenyl]ethylamine (0.72 g; 4.04 mmol), BOP reagent (1.79 g; 4.04 mmol), HOBT (0.55 g; 4.04 mmol) and DiPEA (1.4 mL; 8.08 mmol) were added to a solution of (R)-N$^2$-(diphenylacetyl)-N$^5$-(Cbz)-ornithine (1.86 g; 4.04 mmol, from step (a) above) in THF (200 mL). The reaction was stirred overnight at room temperature and then concentrated in vacuo. The residue was dissolved in EtOAc (100 mL) and washed with KHSO$_4$ solution (100 mL), 0.5 N NaOH (100 mL) and brine (100 mL). The organics were separated dried with Na$_2$SO$_4$ and concentrated. The resulting crude product was crystallized from EtOAc to afford the sub-title compound as a white crystalline solid (0.560 g; 0.90 mmol; 22%).

$R_f$ 0.69 (System B)

(c) (R)-N$^2$-(Diphenylacetyl)-(R,S)-N-[1-(4-(aminocarbonylmethyl)phenyl)ethyl]ornithine amide acetate Acetic acid (3.2 mL; 56.6 mmol) and 10% Pd/C (w/w; 70 mg) were added to a stirred solution of (R)-N$^5$-(Cbz)-N$^2$-(diphenylacetyl)-(R,S)-N-[1-(4-(aminocarbonylmethyl)phenyl)ethyl]ornithine amide (0.56 g; 0.90 mmol; from step (b) above) in methanol (20 mL). The reaction was stirred for 4 h under one atmosphere of hydrogen, filtered through Celite to remove the catalyst and the filtrate was concentrated to afford the sub-title compound as a white solid (0.48 g; 0.84 mmol; 39%).

$R_f$ 0.10 (System B)

(d) (R)-N$^2$-(Diphenylacetyl)-(R,S)-N-[1-(4-(aminocarbonylmethyl)phenyl)ethyl]arginine amide hydrochloride A solution of (R)-N$^2$-(diphenylacetyl)-(R,S)-N-[1-(4-(aminocarbonylmethyl)phenyl)ethyl]ornithine amide acetate (0.48 g; 0.88 mmol; from step (c) above), 1H-pyrazole-1-carboxamidine×HCl (0.14 g; 0.97 mmol) and triethylamine (0.50 mL; 3.52 mmol) in DMF (15 mL) was stirred for 24 hours at room temperature. The reaction was concentrated in vacuo and the residue chromatographed on silica eluting with CHCl$_3$:methanol:conc. NH$_4$OH (6:3:1). Fractions containing the desired compound were combined and concentrated to afford the title compound as a white solid (0.34 g; 0.60 mmol; 68%).

$R_f$ 0.36 (System D)

$^1$H NMR (CD$_3$OD) δ 1.39 (m, 3H), 1.55–1.74 (m, 4H), 3.05 (m, 1H), 3.11 (m, 1H), 3.55 (m, 2H), 4.42 (q, 1H), 5.01 (s, 0.5H), 5.11 (s, 0.5), 7.15–7.45 (m, 14H)

Example 39

(R)-N$^2$-(Diphenylacetyl)-(R,S)-N-[1-(4-(aminocarbonylaminomethyl)phenyl)ethyl]arginine amide hydrochloride (a) (R)-N$^5$-(Cbz)-N$^2$-(diphenylacetyl)-(R,S)-N-[1-(4-(aminocarbonylaminomethyl)phenyl)ethyl]ornithine amide (R,S)-1-[4-(Aminocarbonylaminomethyl)phenyl] ethylamine (0.73 g; 3.77 mmol), BOP reagent (1.67 g; 3.77 mmol), HOBT (0.51 g; 3.77 mmol), DiPEA (1.3 mL; 67.54 mmol) and DMF (15 mL) were added to a solution of (R)-N$^2$-(diphenylacetyl)-N$^5$-(Cbz)-ornithine (1.74 g; 3.77 mmol; see Example 38(a) above) in THF (200 mL). The reaction was stirred overnight at room temperature and then concentrated in vacuo. The residues were dissolved in EtOAc (100 mL) and washed with KHSO$_4$ solution (100 mL), 0.5 N NaOH (100 mL) and brine (100 mL). The organics were separated, dried with Na$_2$SO$_4$ and concentrated to afford the sub-title compound as a pale yellow solid (1.24 g; 1.95 mmol; 52%).

$R_f$ 0.59 (System B)

$^1$H NMR (CD$_3$OD) δ 1.45 (dd, 3H), 1.57 (m, 2H), 1.71 (m, 2H), 2.64 (m, 1H), 3.08 (m, 2H), 4.25 (s, 2H), 4.90 (q, 1H), 5.11 (s, 1H), 5.45 (s, 2H), 7.0–7.4 (m, 19H)

(b) (R)-N$^2$-(Diphenylacetyl)-(R,S)-N-[1-(4-(aminocarbonylaminomethyl)phenyl)ethyl]ornithine amide hydrochloride TMSI (0.36 mL; 2.54 mmol) was added to a stirred solution of (R)-N$^5$-(Cbz)-N$^2$-(diphenylacetyl)-(R,S)-N-[1-

(4-(aminocarbonylaminomethyl)phenyl)ethyl]ornithine amide (1.24 g; 1.95 mmol; from step (a) above) in CH$_3$CN (20 mL) and CH$_2$Cl$_2$ (20 mL). The resultant solution was stirred at room temperature for 1.5 h and then quenched with 1 N HCl (10 mL). The sub-title compound crystallized from the solution as a white solid (0.52 g; 1.04 mmol; 53%).

R$_f$ 0.10 (System B)

(c) (R)-N$^2$-(Diphenylacetyl)-(R,S)-N-[1-(4-(aminocarbonylaminomethyl)phenyl)ethyl]arginine amide hydrochloride A solution of (R)-N$^2$-(diphenylacetyl)-(R,S)-N-[1-(4-(aminocarbonylaminomethyl)phenyl)ethyl]ornithine amide hydrochloride (0.52 g; 1.04 mmol; from step (b) above), 1H-pyrazole-1-carboxamidine×HCl (0.152 g; 1.04 mmol) and triethylamine (0.58 mL; 4.15 mmol) in DMF (8 mL) was stirred for 24 hours at room temperature. The reaction was concentrated in vacuo and the residue chromatographed on silica eluting with CHCl$_3$:CH$_3$OH:conc. NH$_4$OH (6:3:1). Fractions containing the desired compound were combined and concentrated to afford the title compound as a white solid (0.17 g; 0.30 mmol; 29%).

R$_f$ 0.44 (System D)

$^1$H NMR (CD$_3$OD) δ 1.37 (m, 3H), 1.55–1.74 (m, 4H), 3.05 (m, 1H), 3.15 (m, 1H), 4.25 (s, 2H), 4.39 (q, 1H), 5.05 (s, 0.5H), 5.09 (s, 0.5), 7.0–7.4 (m, 14H)

Example 40

(R)-N$^2$-(4,4'-Dichlorodiphenylacetyl)-(R,S)-N-[1-(4-(aminocarbonylmethyl)phenyl)ethyl]arginine amide hydrochloride (a) (R)-N$^5$-(Cbz)-N$^2$-(4,4'-Dichlorobiphenyl)-ornithine 2 N NaOH (200 mL) and 4,4'-dichlorodiphenylacetyl chloride (14.2 mmol) were added to a stirred solution of (R)-N$^5$-(Cbz)-ornithine hydrochloride (4.73 g; 15.6 mmol) in THF (250 mL). After stirring for 18 h, the organic layer was separated and concentrated. The resultant residue was dissolved in EtOAc and washed with 1 N HCl (125 mL) and brine (125 mL). The organics were separated, dried with Na$_2$SO$_4$ and concentrated to afford the sub-title compound as a yellow foam (4.79 g; 9.05 mmol; 64%).

R$_f$ 0.10 (System B)

(b) (R)-N$^5$-(Cbz)-N$^2$-(4,4'-dichlorodiphenylacetyl)-(R,S)-N-[1-(4-(aminocarbonylmethyl)phenyl)ethyl]ornithine amide (R,S)-1-[4-(aminocarbonylmethyl)phenyl]ethylamine (0.72 g; 4.04 mmol), BOP reagent (1.79 g; 4.04 mmol), HOBT (0.55 g; 4.04 mmol) and DiPEA (1.4 mL; 8.08 mmol) were added to a solution of (R)-N$^2$-(4,4'-dichlorodiphenylacetyl)-N$^5$-(Cbz)-ornithine (2.14 g; 4.04 mmol; from step (a) above) in THF (200 mL). The reaction was stirred overnight at room temperature and then concentrated in vacuo. The residue was dissolved in EtOAc (100 mL) and washed with KHSO$_4$ solution (100 mL), 0.5 N NaOH (100 mL) and brine (100 mL). The organics were separated, dried with Na$_2$SO$_4$, and concentrated. The crude product was crystallized from EtOAc to afford the sub-title as a white crystalline solid (0.88 g; 1.27 mmol, 34%).

R$_f$ 0.69 (System B)

(c) (R)-N$^2$-(4,4'-Dichlorodiphenylacetyl)-(R,S)-N-[1-(4-(aminocarbonylmethyl)phenyl)ethyl]ornithine amide acetate Acetic acid (3.2 mL; 56.6 mmol) and 10% Pd/C (w/w; 70 mg) were added to a stirred solution of(R)-N$^5$-(Cbz)-N$^2$-(4,4'-dichlorodiphenylacetyl)-(R,S)-N-[1-(4-(aminocarbonylmethyl)phenyl)ethyl]ornithine amide (0.88 g; 1.27 mmol; from step (b) above) in methanol (20 mL). The reaction mixture was stirred for 4 h under one atmosphere of hydrogen, filtered through Celite to remove the catalyst and the filtrate was concentrated in vacuo to afford the sub-title compound as a white solid (0.56 g; 0.98 mmol; 44%).

R$_f$ 0.10 (System B)

(d) (R)-N$^2$-(4,4'-Dichlorodiphenylacetyl)-(R,S)-N-[1-(4-(aminocarbonylmethyl)phenyl)ethyl]arginine amide hydrochloride A solution of (R)-N$^2$-(4,4'-dichlorodiphenylacetyl)-(R,S)-N-[1-(4-(aminocarbonylmethyl)phenyl)ethyl]ornithine amide acetate (0.55 g; 0.89 mmol; from step (c) above), 1H-pyrazole-1-carboxamidine×HCl (0.14 g; 0.98 mmol) and triethylamine (0.50 mL; 3.56 mmol) in DMF (15 mL) was stirred for 24 hours at room temperature. The reaction was concentrated in vacuo and the residue chromatographed on silica eluting with CHCl$_3$: methanol:conc. NH$_4$OH (6:3:1). Fractions containing the desired compound were combined and concentrated to afford the title compound as a white solid (0.31 g; 0.49 mmol; 55%).

R$_f$ 0.30 (System D)

$^1$H NMR (CD$_3$OD) δ 1.39 (m, 3H), 1.49–1.74 (m, 4H), 3.06 (m, 1H), 3.15 (m, 1H), 3.50 (m, 2H), 4.41 (q, 1H), 5.08 (s, 0.5H), 5.12 (s, 0.5), 7.20–7.37 (m, 12H)

Example 41

(R)-N$^2$-(4,4'-Dichlorodiphenylacetyl)-(R,S)-N-[1-(4-(aminocarbonylaminomethyl)phenyl)ethyl]arginine amide hydrochloride (a) (R)-N$^5$-(Cbz)-N$^2$-(4,4'-dichlorodiphenylacetyl)-(R,S)-[1-(4-(aminocarbonylaminomethyl)phenyl)ethyl]ornithine amide (R,S)-1-[4-(Aminocarbonylaminomethyl)phenyl]ethylamine (0.73 g; 3.77 mmol), BOP reagent (1.67 g; 3.77 mmol), HOBT (0.51 g; 3.77 mmol), DiPEA (1.3 mL, 67.54 mmol) and DMF (20 mL) were added to a solution of (R)-N$^2$-(4,4'-dichlorodiphenylacetyl)-N$^5$-(Cbz)-ornithine (1.99 g; 3.77 mmol; see Example 40(a) above) in THF (200 mL). The reaction was stirred for 18 h at room temperature and then concentrated in vacuo. The residues were dissolved in EtOAc (100 mL) and washed with KHSO$_4$ solution (100 mL), 0.5 N NaOH (100 mL) and brine (100 mL). The organics were separated, dried with Na$_2$SO$_4$ and concentrated to give the sub-title compound as a pale yellow solid (1.60 g; 2.27 mmol; 60%).

R$_f$ 0.55 (System B)

$^1$H NMR (CD$_3$OD) δ 1.45 (dd, 3H), 1.55 (m, 2H), 1.74 (m, 2H), 2.6 (mn, 1H), 3.04 (mn, 2H), 4.22 (s, 2H), 4.90 (q, 1H), 5.01 (s, 1H), 5.50 (s, 2H), 7.0–7.4 (m, 17H)

(b) (R)-N$^2$-(4,4'-Dichlorodiphenylacetyl)-(R,S)-N-[1-(4-(aminocarbonylaminomethyl)phenyl)ethyl]ornithine amide hydrochloride TMSI (0.42 mL; 2.95 mmol) was added to a stirred solution of (R)-N$^5$-(Cbz)-N$^2$-(4,4'-dichlorodiphenylacetyl)-(R,S)-N-[1-(4-(aminocarbonylaminomethyl)phenyl)ethyl] ornithine amide (1.6 g; 2.27 mmol; from step (a) above) in CH$_3$CN (20 mL) and CH$_2$Cl$_2$ (20 mL). The reaction was stirred at room temperature for 1.5 h. and then quenched with 1 N HCl (10 mL). The sub-title compound crystallized from the solution as a white solid (0.52 g, 0.91 mmol, 41%).

R$_f$ 0.10 (System B)

c) (R)-N$^2$-(4,4'-Dichlorodiphenylacetyl)-(R,S)-N-[1-(4-(aminocarbonylaminomethyl)phenyl)ethyl]arginine amide hydrochloride A solution of (R)-N$^2$-(4,4'-dichlorodiphenylacetyl)-(R,S)-N-[1-(4-(aminocarbonylaminomethyl)phenyl)ethyl] ornithine amide×HCl (0.52 g; 0.91 mmol; from step (b) above), 1H-pyrazole-1-carboxamidine x HCl (0.134 g; 0.91 mmol) and triethylamine (0.51 mL; 3.64 mmol) in DMF (8 mL) was stirred for 24 h at room temperature. The reaction was concentrated in vacuo and the residue chromatographed on silica eluting with $CHCl_3$: methanol:conc. $NH_4OH$ (6:3:1). Fractions containing the desired compound were combined and concentrated to afford the title compound as a white solid (0.142 g; 0.218 mmol; 24%).

$R_f$ 0.43 (System D)

$^1H$ NMR ($CD_3OD$) δ 1.39 (m, 3H), 1.50–1.77 (m, 4H), 3.05 (m, 1H), 3.15 (m, 1H), 4.26 (s, 2H), 4.41 (q, 1H), 4.90 (q, 1H), 5.01 (s, 0.5H), 5.11 (s, 0.5), 7.0–7.4 (m, 12H)

Example 42

The title compounds of Examples 1 to 41 were tested in Test A above and were all found to exhibit an $IC_{50}$ value of less than 5.0 μM ($Y_1$ receptors).

| Abbreviations | |
|---|---|
| ACE = | angiotensin-converting enzyme |
| Boc = | t-butoxycarbonyl |
| BOP | 1-benzotriazolyloxytris(dimethylamino)phosphonium hexafluorophosphate |
| Cbz = | benzyloxycarbonyl |
| dec. = | decomposed |
| DiPEA = | diisopropylethylamine |
| DMF = | N,N-dimethylformamide |
| DMSO = | dimethylsulphoxide |
| EDC = | 1-(3-dimethylaminopropyl)-3-ethylcarbodiimide |
| $Et_2O$ = | diethyl ether |
| EtOAc = | ethyl acetate |
| HCl = | hydrochloric acid |
| xHCl = | hydrochloride salt |
| HCl/EtOAc = | EtOAc saturated with hydrogen chloride |
| HCl/MeOH = | MeOH saturated with hydrogen chloride |
| HOAc = | acetic acid |
| HOBT = | N-hydroxybenzotriazole |
| MeOH = | methanol |
| NMR = | nuclear magnetic resonance |
| NPY = | neuropeptide Y |
| Pd/C = | palladium on carbon |
| PE = | polyethylene |
| TEA = | triethylamine |
| TLC = | thin layer chromatography |
| THF = | tetrahydrofuran |
| TMSI = | trimethylsilyl iodide |

What is claimed is:

1. A compound of formula I,

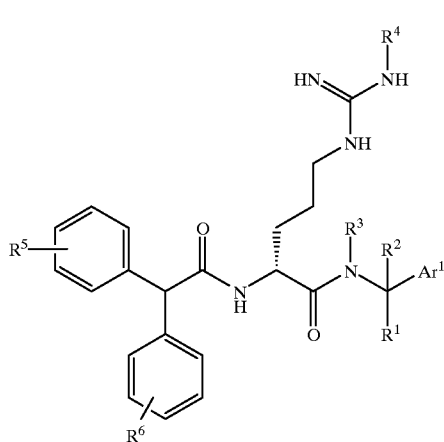

wherein $Ar^1$ represents a structural fragment of the formula

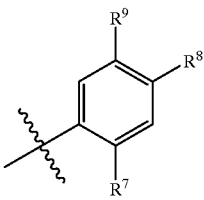

or represents 1- or 2-naphthyl, which latter group is optionally substituted by one or more substituents selected from OH, halo or $C_{1-7}$ alkoxy;

$R^1$ represents $C(O)NH_2$, $C_{1-4}$ alkyl (optionally substituted or terminated by one or more substituents selected from hydroxy or amino), or, together with $R^7$ (in $Ar^1$), forms $C_{2-3}$ alkylene;

$R^4$ represents H, $C_{1-7}$ alkyl or $C_{1-4}$ alkylenephenyl (in which latter group, the phenyl group is optionally substituted by one or more substituent selected from OH or $C_{1-4}$ alkoxy);

$R^5$ and $R^6$ independently represent H, OH, $C_{1-4}$ alkyl, $C_{1-4}$ alkoxy or halo;

$R^7$ represents H, OH or, together with $R^1$, forms $C_{2-3}$ alkylene;

$R^8$ represents H, halo, OH, $C_{1-7}$ alkoxy, phenyl, phenoxy, benzyloxy, $—CH_2)_nC(O)N(R^{10})R^{11}$, $—(CH_2)_nN(H)C(O)N(R^{10})R^{11}$ or $—O(CH_2)_nC(O)OR^{10}$;

$R^9$ represents H, halo, OH or $C_{1-7}$ alkoxy;

$R^2$, $R^3$, $R^{10}$ and $R^{11}$ independently represent H or $C_{1-7}$ alkyl; and n represents 1, 2, 3 or 4;

or a pharmaceutically acceptable derivative thereof.

2. A compound of formula I as claimed in claim 1, wherein $R^1$ represents $C(O)NH_2$, $CH_2OH$, ethyl or methyl.

3. A compound of formula I as claimed in claim 2, wherein $R^1$ represents methyl.

4. A compound of formula I as claimed in claim 1, wherein $R^2$ represents H.

5. A compound of formula I as claimed in claim 1, wherein $R^3$ represents H or methyl.

6. A compound of formula I as claimed in claim 1, wherein $R^4$ represents H.

7. A compound of formula I as claimed in claim 1, wherein $R^5$ represents H, OH, halo, methyl or methoxy.

8. A compound of formula I as claimed in claim 7, wherein $R^5$ represents H.

9. A compound of formula I as claimed in claim 1, wherein $R^6$ represents H, OH, halo, methyl or methoxy.

10. A compound of formula I as claimed in claim 9, wherein $R^6$ represents H.

11. A compound of formula I as claimed in claim 1, wherein $R^7$ represents H.

12. A compound of formula I as claimed in claim 1, wherein $R^8$ represents $OCH_3$, bromo, $—CH_2C(O)NH_2$, $—CH_2N(H)C(O)NH_2$ or OH.

13. A compound of formula I as claimed in claim 12, wherein $R^8$ represents OH.

14. A compound of formula I as claimed in claim 1, wherein $R^9$ represents H.

15. A compound of formula I as claimed in claim 1, wherein $R^{10}$ represents H.

16. A compound of formula I as claimed in claim 1, wherein $R^{11}$ represents H.

17. A compound of formula I as claimed in claim 1, wherein the carbon atom which is in the α-position relative to Ar¹ in the fragment

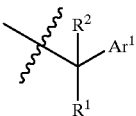

is in the R-configuration when R¹ represents $C_{1-4}$ alkyl.

18. A compound of formula I as claimed in claim 1, wherein the carbon atom which is in the α-position relative to Ar¹ in the fragment

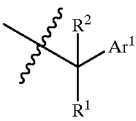

is in the S-configuration when R¹ represents $C(O)NH_2$ or $CH_2OH$.

19. A compound as claimed in claim 1 which is:
(R)-N²-(diphenylacetyl)-(R)-N-[1-(4-methoxyphenyl) ethyl]arginine amide;
(R)-N²-(diphenylacetyl)-(R,S)-N-(1-phenylpropyl) arginine amide;
(R)-N²-(diphenylacetyl)-(R,S)-N-[1-(4-hydroxyphenyl) ethyl]arginine amide;
(R)-N²-(diphenylacetyl)-(R)-N-[1-(4-hydroxyphenyl) ethyl]arginine amide;
(R)-N²-(diphenylacetyl)-(S)-N-[1-(4-methoxyphenyl) ethyl]arginine amide;
(R)-N²-(diphenylacetyl)-(S)-N-[1-(4-bromophenyl)ethyl] arginine amide;
(R)-N²-(diphenylacetyl)-(R)-N-[1-(4-bromophenyl) ethyl]arginine amide;
(R)-N²-(diphenylacetyl)-(R,S)-N-[1-(3-methoxyphenyl) ethyl]arginine amide;
(R)-N²-(diphenylacetyl)-(R)-N-(1-phenylethyl)arginine amide;
(R)-N²-(diphenylacetyl)-(S)-N-(1-phenylethyl)arginine amide;
(R)-N²-(diphenylacetyl)-(R,S)-N-[1-cyclopropyl-1-(4-methoxyphenyl)methyl]arginine amide;
(R)-N²-(diphenylacetyl)-N-(1-methyl-1-phenylethyl) arginine amide;
(R)-N²-(diphenylacetyl)-(R,S)-N-(1-indanyl)arginine amide;
(R)-N²-(diphenylacetyl)-(S or R)-N-(1-carbamoyl-phenylmethyl)arginine amide;
(R)-N²-(diphenylacetyl)-(R or S)-N-[1-carbamoyl-(4-methoxyphenyl)-methyl]arginine amide;
(R)-N²-(diphenylacetyl)-(S)-N-(2-hydroxy-1-phenylethyl)arginine amide;
(R)-N²-(diphenylacetyl)-(R)-N-(2-hydroxy-1-phenylethyl)arginine amide;
(R)-N²-(diphenylacetyl)-(R)-N-[2-hydroxy-1-(4-methoxyphenyl)ethyl]arginine amide;
(R)-N²-(diphenylacetyl)-(S)-N-[2-hydroxy-1-(4-methoxyphenyl)ethyl]arginine amide;
(R)-N²-(diphenylacetyl)-(S)-N-[1-(4-hydroxyphenyl) ethyl]arginine amide;
(R)-N²-(diphenylacetyl)-(R,S)-N-[1-(4-methoxyphenyl) ethyl]arginine amide;
(R)-N²-(diphenylacetyl)-N-methyl-(R)-N-(1-phenylethyl)arginine amide;
(R)-N²-(diphenylacetyl)-N-methyl-(S)-N-(1-phenylethyl) arginine amide;
(R)-N²-(diphenylacetyl)-(R,S)-N-[1-(4-cyclopropylmethoxyphenyl)ethyl]-arginine amide;
(R)-N²-(diphenylacetyl)-(R)-N-[1-(4-benzyloxyphenyl) ethyl]arginine amide;
(R)-N²-(diphenylacetyl)-(R,S)-N-[1-(4-phenoxyphenyl) ethyl]arginine amide;
(R)-N²-(diphenylacetyl)-(R,S)-N-[1-(4-phenylphenyl) ethyl]arginine amide;
(R)-N²-(diphenylacetyl)-(R,S)-N-[1-(2-naphthyl)ethyl] arginine amide;
(R)-N²-(diphenylacetyl)-(R)-N-[1-(1-naphthyl)ethyl] arginine amide;
(R)-N²-[(R,S)-2-(4-methoxyphenyl)phenylacetyl]-(R)-N-[1-(4-hydroxyphenyl)ethyl]arginine amide;
(R)-N²-[(R,S)-2-(4-methylphenyl)phenylacetyl]-(R)-N-[1-(4-hydroxyphenyl)ethyl]arginine amide;
(R)-N²-[(R,S)-2-(4-chlorophenyl)phenylacetyl]-(R)-N-[1-(4-hydroxyphenyl)ethyl]arginine amide;
(R)-N²-(4,4'-dichlorodiphenylacetyl)-(R)-N-[1-(4-hydroxyphenyl)ethyl]arginine amide;
(R)-N²-[(R,S)-2-(4-hydroxyphenyl)phenylacetyl]-(R)-N-[1-(4-hydroxyphenyl)ethyl]arginine amide;
(R)-N^ω-(ethyl)-N²-(diphenylacetyl)-(R)-N-[1-(4-methoxyphenyl)ethyl]arginine amide;
(R)-N^ω-(benzyl)-N²-(diphenylacetyl)-(R)-N-[1-(4-methoxyphenyl)ethyl]arginine amide;
(R)-N^ω-(1-(4-hydroxyphenyl)ethyl)-N²-(diphenylacetyl)-(R)-N-[1-(4-hydroxyphenyl)ethyl]arginine amide;
(R)-N²-(diphenylacetyl)-(R,S)-N-[1-(4-(aminocarbonylmethyl)phenyl)ethyl]arginine amide;
(R)-N²-(diphenylacetyl)-(R,S)-N-[1-(4-(aminocarbonylaminomethyl)phenyl)ethyl]arginine amide;
(R)-N²-(4,4'-dichlorodiphenylacetyl)-(R,S)-N-[1-(4-(aminocarbonylmethyl)phenyl)ethyl]arginine amide; or
(R)-N²-(4,4'-dichlorodiphenylacetyl)-(R,S)-N-[1-(4-(aminocarbonylaminomethyl)phenyl)ethyl]arginine amide.

20. A compound as claimed in claim 1 which is:
(R)-N²-(diphenylacetyl)-(R)-N-[1-(4-methoxyphenyl) ethyl]arginine amide;
(R)-N²-(diphenylacetyl)-(R)-N-[1-(4-hydroxyphenyl) ethyl]arginineamide;
(R)-N²-[(R,S)-2-(4-chlorophenyl)phenylacetyl]-(R)-N-[1-(4-hydroxyphenyl)ethyl]arginine amide;
(R)-N²-(4,4'-dichlorodiphenylacetyl)-(R)-N-[1-(4-hydroxyphenyl)ethyl]arginine amide; or
(R)-N²-[(R,S)-2-(4-hydroxyphenyl)phenylacetyl]-(R)-N-[1-(4-hydroxyphenyl)ethyl]arginine amide.

21. A pharmaceutical formulation including a compound as defined in claim 1, or a pharmaceutically acceptable derivative thereof, in admixture with a pharmaceutically acceptable adjuvant, diluent or carrier.

22. A method of treatment of a cardiovascular disease, which method comprises administration of a therapeutically effective amount of a compound as defined in claim 1, or a pharmaceutically acceptable derivative thereof, to a person suffering from, or susceptible to, such a condition.

23. A method of treatment of a vasoconstriction, which method comprises administration of a therapeutically effective amount of a compound as defined in claim 1, or a pharmaceutically acceptable derivative thereof, to a person suffering from, or susceptible to, such a condition.

24. A process for the preparation of compounds of formula I which comprises:

(a) reaction of a compound of formula II,

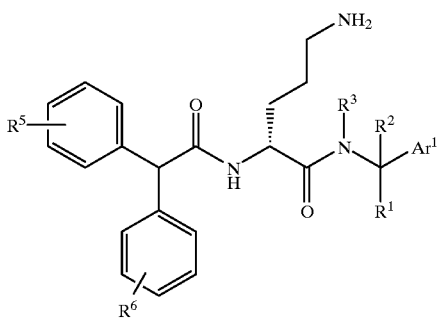

wherein $Ar^1$, $R^1$, $R^2$, $R^3$, $R^5$ and $R^6$ are as defined in claim 1 with a compound of formula III,

or a hydrogen sulphate salt thereof, wherein $R^a$ represents $C_{1-4}$ alkyl and $R^4$ is as defined in claim 1;

(b) for compounds of formula I in which $R^4$ represents H, reaction of a compound of formula II as defined above with 1H-pyrazole-1-carboxamidine, or a hydrohalide salt thereof;

(c) reaction of a compound of formula II as defined above with a compound of formula IV,

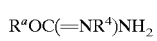

or a hydrogen sulphate salt thereof, wherein $R^a$ is as defined above and $R^4$ is as defined in claim 1;

(d) for compounds of formula I in which $R^4$ represents H, reaction of a compound of formula II as defined above with a compound of formula V,

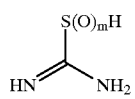

wherein m represents 2 or 3;

(e) reaction of a compound of formula VI,

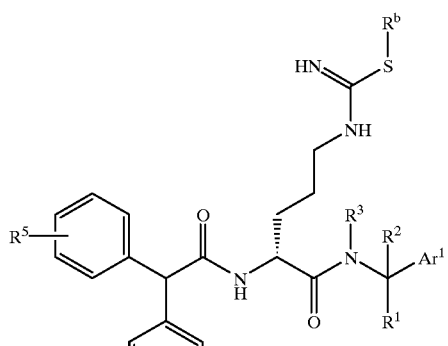

wherein $R^b$ represents $C_{1-4}$ alkyl and $Ar^1$, $R^1$, $R^2$, $R^3$, $R^5$ and $R^6$ are as defined in claim 1 with a compound of formula VII,

wherein $R^4$ is as defined in claim 1;

(f) reaction of a compound of formula VIII,

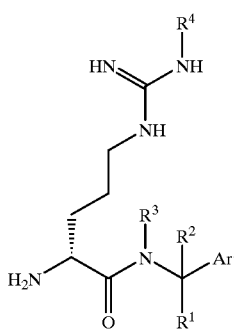

wherein $Ar^1$, $R^1$, $R^2$, $R^3$ and $R^4$ are as defined in claim 1 with a compound of formula IX,

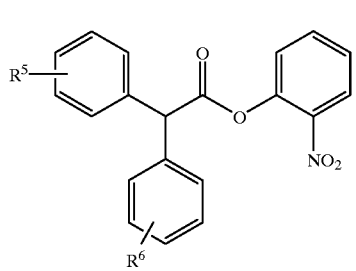

wherein $R^5$ and $R^6$ are as defined in claim 1;

(g) reaction of a compound of formula VIII, as defined above, with a compound of formula X,

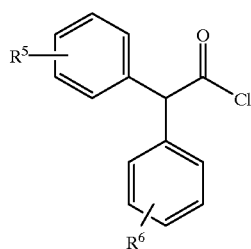
X
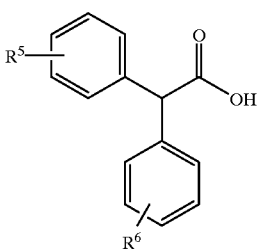
XI
wherein $R^5$ and $R^6$ are as defined in claim 1; or
(h) reaction of a compound of formula VIII, as defined above, with a compound of formula XI,
wherein $R^5$ and $R^6$ are as defined in claim 1.
* * * * *